US012735700B2

(12) United States Patent
Bui

(10) Patent No.: US 12,735,700 B2
(45) Date of Patent: Sep. 15, 2026

(54) COMPOUNDS AND METHODS FOR REDUCING FUS EXPRESSION

(71) Applicant: Ionis Pharmaceuticals, Inc., Carlsbad, CA (US)

(72) Inventor: Huynh-Hoa Bui, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 1139 days.

(21) Appl. No.: 17/613,183

(22) PCT Filed: May 28, 2020

(86) PCT No.: PCT/US2020/034907

§ 371 (c)(1),
(2) Date: Nov. 22, 2021

(87) PCT Pub. No.: WO2020/243292

PCT Pub. Date: Dec. 3, 2020

(65) Prior Publication Data

US 2022/0243203 A1 Aug. 4, 2022

Related U.S. Application Data

(60) Provisional application No. 62/853,616, filed on May 28, 2019.

(51) Int. Cl.
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/3341* (2013.01); *C12N 2310/341* (2013.01)

(58) Field of Classification Search
CPC .............. C12N 15/113; C12N 2310/11; C12N 2310/315; C12N 2310/3341; C12N 2310/341
See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |

(Continued)

FOREIGN PATENT DOCUMENTS

| | | | |
|---|---|---|---|
| EP | 2655621 B1 * | 5/2018 | ........... C12N 15/113 |
| WO | 2004/091515 A2 | 10/2004 | |

(Continued)

OTHER PUBLICATIONS

Wan WB,et al Synthesis, biophysical properties and biological activity of second generation antisense oligonucleotides containing chiral phosphorothioate linkages. Nucleic Acids Res. Dec. 16, 2014;42(22): 13456-68. doi: 10.1093/nar/gku1115. Epub Nov. 14, 2014. PMID: 25398895; PMCID: PMC4267618. (Year: 2014).*

(Continued)

*Primary Examiner* — Tracy Vivlemore

(74) *Attorney, Agent, or Firm* — Sughrue Mion, PLLC

(57) ABSTRACT

Provided are compounds, methods, and pharmaceutical compositions for reducing the amount or activity of FUS RNA in a cell or subject, and in certain instances reducing the amount of FUS protein in a cell or subject. These compounds, methods, and pharmaceutical compositions are useful to ameliorate at least one symptom or hallmark of a neurodegenerative condition. Such symptoms and hallmarks include muscle weakness and fatigue, protein aggregates in the central nervous system, and speech difficulties and behavioral abnormalities. Non-limiting examples of neurodegenerative conditions that benefit from these compounds, methods, and pharmaceutical compositions are amyotrophic lateral sclerosis (ALS) and frontotemporal lobar degeneration (FTLD).

25 Claims, No Drawings

Specification includes a Sequence Listing.

(56) References Cited

U.S. PATENT DOCUMENTS

| | | | | |
|---|---|---|---|---|
| 5,264,564 | A | 11/1993 | Matteucci | |
| 5,276,019 | A | 1/1994 | Cohen et al. | |
| 5,286,717 | A | 2/1994 | Cohen et al. | |
| 5,319,080 | A | 6/1994 | Leumann | |
| 5,321,131 | A | 6/1994 | Agrawal et al. | |
| 5,359,044 | A | 10/1994 | Cook et al. | |
| 5,366,878 | A | 11/1994 | Pederson et al. | |
| 5,367,066 | A | 11/1994 | Urdea et al. | |
| 5,378,825 | A | 1/1995 | Cook et al. | |
| 5,386,023 | A | 1/1995 | Sanghvi et al. | |
| 5,393,878 | A | 2/1995 | Leumann | |
| 5,399,676 | A | 3/1995 | Froehler | |
| 5,403,711 | A | 4/1995 | Walder et al. | |
| 5,405,938 | A | 4/1995 | Sumerton et al. | |
| 5,405,939 | A | 4/1995 | Suhadolnik et al. | |
| 5,432,272 | A | 7/1995 | Benner | |
| 5,434,257 | A | 7/1995 | Matteucci | |
| 5,446,137 | A | 8/1995 | Maag et al. | |
| 5,453,496 | A | 9/1995 | Caruthers et al. | |
| 5,455,233 | A | 10/1995 | Spielvogel et al. | |
| 5,457,187 | A | 10/1995 | Gmelner et al. | |
| 5,457,191 | A | 10/1995 | Cook et al. | |
| 5,459,255 | A | 10/1995 | Cook et al. | |
| 5,466,677 | A | 11/1995 | Baxter et al. | |
| 5,466,786 | A | 11/1995 | Burh et al. | |
| 5,470,967 | A | 11/1995 | Huie et al. | |
| 5,476,925 | A | 12/1995 | Letsinger et al. | |
| 5,484,908 | A | 1/1996 | Froehler et al. | |
| 5,489,677 | A | 2/1996 | Sanghvi et al. | |
| 5,491,133 | A | 2/1996 | Walder et al. | |
| 5,502,177 | A | 3/1996 | Matteucci et al. | |
| 5,508,270 | A | 4/1996 | Baxter et al. | |
| 5,514,785 | A | 5/1996 | Van Ness et al. | |
| 5,519,126 | A | 5/1996 | Hecht | |
| 5,519,134 | A | 5/1996 | Acevedo et al. | |
| 5,525,711 | A | 6/1996 | Hawkins et al. | |
| 5,527,899 | A | 6/1996 | Froehler | |
| 5,536,821 | A | 7/1996 | Agrawal et al. | |
| 5,541,306 | A | 7/1996 | Agrawal et al. | |
| 5,541,307 | A | 7/1996 | Cook et al. | |
| 5,550,111 | A | 8/1996 | Suhadolnik et al. | |
| 5,552,540 | A | 9/1996 | Haralambidis | |
| 5,561,225 | A | 10/1996 | Maddry et al. | |
| 5,563,253 | A | 10/1996 | Agrawal et al. | |
| 5,565,350 | A | 10/1996 | Kmiec | |
| 5,565,555 | A | 10/1996 | Froehler et al. | |
| 5,567,811 | A | 10/1996 | Mistura et al. | |
| 5,571,799 | A | 11/1996 | Tkachuk et al. | |
| 5,576,427 | A | 11/1996 | Cook et al. | |
| 5,587,361 | A | 12/1996 | Cook et al. | |
| 5,587,469 | A | 12/1996 | Cook et al. | |
| 5,587,470 | A | 12/1996 | Cook et al. | |
| 5,591,722 | A | 1/1997 | Montgomery et al. | |
| 5,594,121 | A | 1/1997 | Froehler et al. | |
| 5,596,086 | A | 1/1997 | Matteucci | |
| 5,596,091 | A | 1/1997 | Switzer | |
| 5,597,909 | A | 1/1997 | Urdea et al. | |
| 5,602,240 | A | 2/1997 | De Mesmaeker et al. | |
| 5,608,046 | A | 3/1997 | Cook et al. | |
| 5,610,289 | A | 3/1997 | Cook et al. | |
| 5,610,300 | A | 3/1997 | Altmann et al. | |
| 5,614,617 | A | 3/1997 | Cook et al. | |
| 5,618,704 | A | 4/1997 | Sanghvi et al. | |
| 5,623,065 | A | 4/1997 | Cook et al. | |
| 5,623,070 | A | 4/1997 | Cook et al. | |
| 5,625,050 | A | 4/1997 | Beaton et al. | |
| 5,627,053 | A | 5/1997 | Usman et al. | |
| 5,633,360 | A | 5/1997 | Bishofberger et al. | |
| 5,639,873 | A | 6/1997 | Barascut et al. | |
| 5,645,985 | A | 7/1997 | Froehler et al. | |
| 5,646,265 | A | 7/1997 | McGee | |
| 5,646,269 | A | 7/1997 | Matteucci | |
| 5,652,355 | A | 7/1997 | Metelev et al. | |
| 5,652,356 | A | 7/1997 | Agrawal | |
| 5,663,312 | A | 9/1997 | Chaturvedula | |
| 5,670,633 | A | 9/1997 | Cook et al. | |
| 5,672,697 | A | 9/1997 | Buhr et al. | |
| 5,677,437 | A | 10/1997 | Teng et al. | |
| 5,677,439 | A | 10/1997 | Weis et al. | |
| 5,681,941 | A | 10/1997 | Cook et al. | |
| 5,698,685 | A | 12/1997 | Summerton et al. | |
| 5,700,920 | A | 12/1997 | Altmann et al. | |
| 5,700,922 | A | 12/1997 | Cook | |
| 5,721,218 | A | 2/1998 | Froehler | |
| 5,750,692 | A | 5/1998 | Cook et al. | |
| 5,763,588 | A | 6/1998 | Matteucci et al. | |
| 5,792,608 | A | 8/1998 | Swaminathan et al. | |
| 5,792,847 | A | 8/1998 | Burh et al. | |
| 5,801,154 | A | 9/1998 | Baracchini et al. | |
| 5,808,027 | A | 9/1998 | Cook et al. | |
| 5,830,653 | A | 11/1998 | Froehler et al. | |
| 5,859,221 | A | 1/1999 | Cook et al. | |
| 5,948,903 | A | 9/1999 | Cook et al. | |
| 5,994,517 | A | 11/1999 | Ts'O | |
| 6,005,087 | A | 12/1999 | Cook et al. | |
| 6,005,096 | A | 12/1999 | Matteucci et al. | |
| 6,166,199 | A | 12/2000 | Cook et al. | |
| 6,300,319 | B1 | 10/2001 | Manoharan | |
| 6,426,220 | B1 | 7/2002 | Bennett et al. | |
| 6,525,191 | B1 | 2/2003 | Ramasamy | |
| 6,531,584 | B1 | 3/2003 | Cook et al. | |
| 6,582,908 | B2 | 6/2003 | Fodor et al. | |
| 6,600,032 | B1 | 7/2003 | Manoharan et al. | |
| 6,660,720 | B2 | 12/2003 | Manoharan | |
| 6,770,748 | B2 | 8/2004 | Imanishi et al. | |
| 7,015,315 | B1 | 3/2006 | Cook et al. | |
| 7,053,207 | B2 | 5/2006 | Wengel et al. | |
| 7,101,993 | B1 | 9/2006 | Cook et al. | |
| 7,250,289 | B2 | 7/2007 | Zhou | |
| 7,250,496 | B2 | 7/2007 | Bentwich | |
| 7,262,177 | B2 | 8/2007 | Ts'o et al. | |
| 7,399,845 | B2 | 7/2008 | Seth et al. | |
| 7,427,672 | B2 | 9/2008 | Imanishi et al. | |
| 7,491,805 | B2 | 2/2009 | Vargeese et al. | |
| 7,547,684 | B2 | 6/2009 | Seth et al. | |
| 7,569,686 | B1 | 8/2009 | Bhat et al. | |
| 7,666,854 | B2 | 2/2010 | Seth et al. | |
| 7,696,345 | B2 | 4/2010 | Allerson et al. | |
| 7,723,509 | B2 | 5/2010 | Manoharan et al. | |
| 7,741,457 | B2 | 6/2010 | Swayze et al. | |
| 7,750,131 | B2 | 7/2010 | Seth et al. | |
| 7,875,733 | B2 | 1/2011 | Bhat et al. | |
| 7,939,677 | B2 | 5/2011 | Bhat et al. | |
| 8,022,193 | B2 | 9/2011 | Swayze et al. | |
| 8,030,467 | B2 | 10/2011 | Seth et al. | |
| 8,080,644 | B2 | 12/2011 | Wengel et al. | |
| 8,088,746 | B2 | 1/2012 | Seth et al. | |
| 8,088,904 | B2 | 1/2012 | Swayze et al. | |
| 8,106,022 | B2 | 1/2012 | Manoharan et al. | |
| 8,124,745 | B2 | 2/2012 | Allerson et al. | |
| 8,153,365 | B2 | 4/2012 | Wengel et al. | |
| 8,268,980 | B2 | 9/2012 | Seth et al. | |
| 8,278,283 | B2 | 10/2012 | Seth et al. | |
| 8,278,425 | B2 | 10/2012 | Prakash et al. | |
| 8,278,426 | B2 | 10/2012 | Seth et al. | |
| 8,440,803 | B2 | 5/2013 | Swayze et al. | |
| 8,501,805 | B2 | 8/2013 | Seth et al. | |
| 8,530,640 | B2 | 9/2013 | Seth et al. | |
| 8,546,556 | B2 | 10/2013 | Seth et al. | |
| RE44,779 | E | 2/2014 | Imanishi et al. | |
| 8,828,956 | B2 | 9/2014 | Manoharan et al. | |
| 9,005,906 | B2 | 4/2015 | Swayze et al. | |
| 9,012,421 | B2 | 4/2015 | Migawa et al. | |
| 9,127,276 | B2 | 9/2015 | Prakash et al. | |
| 9,150,860 | B2 | 10/2015 | Kwiatkowski et al. | |
| 9,290,760 | B2 | 3/2016 | Rajeev et al. | |
| 9,926,559 | B2 * | 3/2018 | Bennett | A61K 31/185 |
| 2001/0053519 | A1 | 12/2001 | Fodor et al. | |
| 2003/0158403 | A1 | 8/2003 | Manoharan et al. | |
| 2003/0175906 | A1 | 9/2003 | Manoharan et al. | |
| 2003/0228597 | A1 | 12/2003 | Cowsert et al. | |
| 2004/0171570 | A1 | 9/2004 | Allerson et al. | |
| 2005/0130923 | A1 | 6/2005 | Bhat et al. | |
| 2006/0148740 | A1 | 7/2006 | Platenburg | |

(56) References Cited

U.S. PATENT DOCUMENTS

2007/0031844 A1 2/2007 Khvorova et al.
2008/0039618 A1 2/2008 Allerson et al.
2010/0190837 A1 7/2010 Migawa et al.
2010/0197762 A1 8/2010 Swayze et al.
2013/0130378 A1 5/2013 Manoharan et al.
2014/0107330 A1 4/2014 Freier et al.
2015/0018540 A1 1/2015 Prakash et al.
2015/0184153 A1 7/2015 Freier et al.
2015/0191727 A1 7/2015 Migawa et al.
2015/0267195 A1 9/2015 Seth et al.
2015/0275212 A1 10/2015 Albaek et al.
2016/0177389 A1 6/2016 Kwiatkowski et al.
2017/0022504 A1 1/2017 Lee et al.
2017/0037410 A1* 2/2017 Swayze .................. A61P 43/00
2019/0309291 A1* 10/2019 Lee ..................... C12N 15/113

FOREIGN PATENT DOCUMENTS

WO WO 2005/116204 12/2005
WO WO 2006/006948 1/2006
WO WO 2010/011283 1/2010
WO 2012/177639 A2 12/2012
WO WO 2013/173637 11/2013
WO WO 2019/032613 2/2019
WO WO 2020/243292 12/2020

OTHER PUBLICATIONS

Bennett CF, Krainer AR, Cleveland DW. Antisense Oligonucleotide Therapies for Neurodegenerative Diseases. Annu Rev Neurosci. Jul. 8, 2019;42:385-406. doi: 10.1146/annurev-neuro-070918-050501. PMID: 31283897; PMCID: PMC7427431. (Year: 2019).*
Evers MM, Toonen LJ, van Roon-Mom WM. Antisense oligonucleotides in therapy for neurodegenerative disorders. Adv Drug Deliv Rev. Jun. 29, 2015;87:90-103. doi: 10.1016/j.addr.2015.03.008. Epub Mar. 20, 2015. PMID: 25797014. (Year: 2015).*
Armstrong et al., "Loss and gain of FUS function impair neuromuscular synaptic transmission in a genetic model of ALS" Hum Mol Genet (2013) 22(21): 4282-4292.
Bailey et al., "Nucleic acid binding proteins affect the subcellular distribution of phosphorothioate antisense oligonucleotides" Nucleic Acids Res (2017) 45(18): 10649-10671.
Branch et al., "A good antisense molecule is hard to find," TIBS (1998) 23:45-50.
Bronisz et al. "The Multifunctional Protein Fused in Sarcoma (FUS) Is a Coactivator of Microphthalmia-associated Transcription Factor (MITF)" J Biol Biochem (2014) 289: 326-334.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Crooke, ST., et al., "Antisense Drug Technology" Second Edition, CRC Press (2008) Chapters 1-28.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Gautschi et al., "Activity of a novel bcl-2/bcl-xLbispecific antisense oligonucleotide against tumors of diverse histologic origins" J. Natl. Cancer Inst. (2001) 93:463-471.
GenBank Accession No. NM_004960.3 downloaded Feb. 11, 2022.
International Search Report for PCT/US2020/034907 dated Oct. 19, 2020.
Kabashi et al., "FUS and TARDBP but not SOD1 interact in genetic models of amyotrophic lateral sclerosis" PLoS Genet (2011) 7(8): e1002214.
Kapeli et al., "Distinct and shared functions of ALS-associated proteins TDP-43, FUS and TAF15 revealed by multisystem analysis" Nature Comm (2016) 7: 1-14.
Korobeynikov et al., "Antisense oligonucleotide silencing of FUS expression as a therapeutic approach in amyotrophic lateral sclerosis" Nature Med (2022) 28: 104-116.
Kwiatkowski et al., "Mutations in the FUS/TLS gene on chromosome 16 cause familial amyotrophic lateral sclerosis" Science (2009) 323(5918): 1205-1208.
Lagier-Tourenne et al., "Divergent roles of ALS-linked proteins FUS/TLS and TDP-43 intersect in processing long pre-mRNAs" Nat Neurosci (2012) 15(11): 1488-1497.
Ling et al., "Overriding FUS autoregulation in mice triggers gain-of-toxic dysfunctions in RNA metabolism and autophagy-lysosome axis" eLIFE (2019) 8:1-38.
Lopez-Erauskin et al., "ALS/FTD-Linked Mutation in FUS Suppresses Intra-axonal Protein Synthesis and Drives Disease Without Nuclear Loss-of-Function of FUS" Neuron (2018) 100: 816-830.
Maher et al., "Comparative hybrid arrest by tandem antisense oligodeoxyribonucleotides or oligodeoxyribonucleoside methylphosphonates in a cell-free system" Nucl. Acid. Res. (1988) 16(8):3341-3358.
Nakaya et al., "FUS regulates genes coding for RNA-binding proteins in neurons by binding to their highly conserved introns" RNA (2013) 19(4): 498-509.
New England Biolabs 1998/99 Catalog (cover page and pp. 121 and 284).
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Sharma et al., "ALS-associated mutant FUS induces selective motor neuron degeneration through toxic gain of function" Nature Comm (2016) 1-14.
Vance et al., "Mutations in FUS, an RNA processing protein, cause familial amyotrophic lateral sclerosis type 6" Science (2009) 323(5918): 1208-1211.
Wang et al., "Mutant FUS causes DNA ligation defects to inhibit oxidative damage repair in Amyotrophic Lateral Sclerosis" Nat Commun (2018) 9: 3683.
Woolf et al., "Specificity of antisense oligonucleotides in vivo" PNAS (1992) 89: 7305-7309.
Extended EP Search Report for 20815459.1 dated Sep. 8, 2023.
Lagier-Tourenne et al., "Divergent roles of ALS-linked proteins FUS/TLS and TDP-43 intersect in processing long pre-mRNAs" Nat Neurosci (2012) Supplemental Info 1-86.
Zhou et al., "ALS-associated FUS mutations result in compromised FUS alternative splicing and autoregulation" PLoS Genet (2013) 9: e1003895.
Partial European Search Report dated Apr. 16, 2026 in European Application No. 25162118.1.

* cited by examiner

COMPOUNDS AND METHODS FOR REDUCING FUS EXPRESSION

SEQUENCE LISTING

The present application is being filed along with a Sequence Listing in electronic format. The Sequence Listing is provided as a file entitled BIOL0360USAEQ_ST25.txt, created on Nov. 9, 2021, which is 136 kb in size. The information in the electronic format of the sequence listing is incorporated herein by reference in its entirety.

FIELD

Mutations in the Fused in Sarcoma gene (FUS) are associated with several neurodegenerative conditions, such as amyotrophic lateral sclerosis (ALS) and frontotemporal lobar degeneration (FTLD). Provided are compounds, methods, and pharmaceutical compositions for reducing an amount of FUS RNA in a cell or subject. In certain instances, compounds, methods, and pharmaceutical compositions reduce an amount of a FUS protein in a cell or a subject. Such compounds, methods, and pharmaceutical compositions are useful to ameliorate at least one symptom or hallmark of a neurodegenerative condition.

BACKGROUND

ALS, also known as Lou Gehrig's disease, is a neurodegenerative disease that causes motor neuron death. ALS patients suffer from muscle stiffness, muscle twitching, muscle weakness, and decreased muscle mass. ALS progresses until patients are unable to walk, speak, swallow or breathe. There are several types of ALS and they are generally classified as familial ALS or sporadic ALS. A significant percentage of familial ALS cases are associated with a mutation in the FUS gene, a gene encoding RNA-binding protein FUS/TLS (Fused in Sarcoma/Translocated in Sarcoma). In healthy patients, the majority of FUS protein localizes to the nucleus of neurons where they function to process RNA. However, in ALS patients, a mutation in FUS causes a FUS protein to aggregate in the cytoplasm, leading to protein misfolding and aggregation. Although the age of onset for ALS is typically greater than 40, there are some instances in which patients develop ALS symptoms before the age of 25. ALS that develops in patients under the age of 25 is referred to as "juvenile ALS." The most common mutations in juvenile ALS include mutations in FUS.

FTLD, also known as Pick's disease, is a term used to describe several disorders including frontotemporal dementia as behavioral variant, primary nonfluent aphasia, semantic dementia as language variants, amyotrophic lateral sclerosis with frontotemporal dementia (ALS+FTLD), corticobasal syndrome and progressive supranuclear palsy. FTLD is characterized by frontal lobe and temporal lobe atrophy. In some instances, accumulation of tau proteins (Pick-bodies) and TAR DNA binding protein 43 are observed in the brain of FTLD patients. These cases are classified as FTLD-tau or FTLD-TDP. In other instances, FUS positive cytoplasmic inclusions, intranuclear inclusions and neuritic threads are observed in the cortex, medulla, hippocampus and motor cells of the spinal cord are observed in FTLD patients, referred to as FTLD-FUS.

SUMMARY OF THE INVENTION

Currently there remains a need for therapies to treat ALS and FTLDs. It is therefore an object herein to provide compounds, methods, and pharmaceutical compositions for the treatment of such diseases.

Provided herein are compounds, methods and pharmaceutical compositions for reducing an amount of FUS RNA, and in certain embodiments reducing the amount or activity of FUS protein in a cell or a subject. In certain embodiments, the subject has a neurodegenerative condition. In certain embodiments, the subject has a neurodegenerative condition. In certain embodiments, the subject has ALS. In certain embodiments, the subject has an FTLD. In certain embodiments, the subject has a mutation in FUS. In certain embodiments, compounds useful for reducing the amount of FUS RNA and/or FUS protein are oligomeric compounds. In certain embodiments, oligomeric compounds comprise modified oligonucleotides.

Also provided herein are methods useful for ameliorating a symptom or hallmark of a neurodegenerative condition. Exemplary symptoms and hallmarks of ALS include, but are not limited to, muscle weakness and fatigue, slurred speech, twitching, cramping, and protein aggregates in the CNS. Exemplary symptoms and hallmarks of FTLD include, but are not limited to, speech difficulties and behavioral abnormalities.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyribosyl sugar moiety. In certain embodiments, a 2'-deoxynucleoside is a 2'-β-D-deoxynucleoside and comprises a 2'-β-D-deoxyribosyl sugar moiety, which has the β-D configuration as found in naturally occurring deoxyribonucleic acids (DNA). In certain embodiments, a 2'-deoxynucleoside or nucleoside comprising an unmodified 2'-deoxyribosyl sugar moiety may comprise a modified nucleobase or may comprise an RNA nucleobase (uracil).

As used herein, "2'-MOE" or "2'-MOE sugar moiety" means a 2'-$OCH_2CH_2OCH_3$ group in place of the 2'—OH group of a ribosyl sugar moiety. "MOE" means methoxyethyl.

As used herein, "2'-MOE nucleoside" means a nucleoside comprising a 2'-MOE sugar moiety.

As used herein, "2'-OMe" or "2'-O-methyl sugar moiety" means a 2'-$OCH_3$ group in place of the 2'—OH group of a ribosyl sugar moiety.

As used herein, "2'-OMe nucleoside" means a nucleoside comprising a 2'-OMe sugar moiety.

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to a subject.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cleavable moiety" means a bond or group of atoms that is cleaved under physiological conditions, for example, inside a cell or a subject.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. As used herein, "complementary nucleobases" means nucleobases that are capable of forming hydrogen bonds with one another. Complementary nucleobase pairs include adenine (A) with thymine (T), adenine (A) with uracil (U), cytosine (C) with guanine (G), and 5-methyl cytosine (mC) with guanine (G). Complementary oligonucleotides and/or nucleic acids need not have nucleobase complementarity at each nucleoside. Rather, some mismatches are tolerated. As used herein, "fully complementary" or "100% complementary" in reference to an oligonucleotide, or portion thereof, means that oligonucleotide, or portion thereof, is complementary to another oligonucleotide or nucleic acid at each nucleobase of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "constrained ethyl" or "cEt" or "cEt modified sugar" means a β-D ribosyl bicyclic sugar moiety wherein the second ring of the bicyclic sugar is formed via a bridge connecting the 4'-carbon and the 2'-carbon of the β-D ribosyl sugar moiety, wherein the bridge has the formula 4'-$CH(CH_3)$—O-2', and wherein the methyl group of the bridge is in the S configuration.

As used herein, "cEt nucleoside" means a nucleoside comprising cEt modified sugar moiety.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif Unless otherwise indicated, the sugar moiety of each nucleoside of the gap is a 2'-β-D-deoxyribosyl sugar moiety. Thus, the term "MOE gapmer" indicates a gapmer having a gap comprising 2'-β-D-deoxynucleosides and wings comprising 2'-MOE nucleosides. Unless otherwise indicated, a MOE gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid that is amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "internucleoside linkage" means the covalent linkage between contiguous nucleosides in an oligonucleotide. As used herein "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "motif" means the pattern of unmodified and/or modified sugar moieties, nucleobases, and/or internucleoside linkages, in an oligonucleotide.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside is a modified oligonucleoside or at least one internucleoside linkage is a modified internucleoside linkage. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to a subject. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in a free uptake assay in certain cell lines.

As used herein "prodrug" means a therapeutic agent in a form outside the body that is converted to a different form within a subject or cells thereof. Typically, conversion of a prodrug within the subject is facilitated by the action of an enzymes (e.g., endogenous or viral enzyme) or chemicals present in cells or tissues and/or by physiologic conditions.

As used herein, "reducing or inhibiting the amount or activity" refers to a reduction or blockade of the transcriptional expression or activity relative to the transcriptional expression or activity in an untreated or control sample and does not necessarily indicate a total elimination of transcriptional expression or activity.

As used herein, "RNA" means an RNA transcript and includes pre-mRNA and mature mRNA unless otherwise specified.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard cell assay" means the assay described in Example 1 and reasonable variations thereof.

As used herein, "stereorandom" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "subject" means a human or non-human animal. In certain embodiments, the subject is a human. In certain embodiments, the subject has been diagnosed with ALS. In certain embodiments, the subject has been diagnosed with FTLD. In certain embodiments, the subject is at risk for ALS or FTLD. In certain embodiments, the subject at risk for ALS or FTL has a mutation in FUS. In certain embodiments, the mutation in FUS is associated with ALS or FTLD. In certain embodiments, the mutation in FUS is causative of ALS or FTLD.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "symptom or hallmark" means any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to a subject. For example, a therapeutically effective amount improves a symptom or hallmark of a disease.

Certain Embodiments

The present disclosure provides the following non-limiting numbered embodiments:

Embodiment 1. An oligomeric compound comprising a modified oligonucleotide consisting of 12 to 50 linked nucleosides wherein the nucleobase sequence of the modified oligonucleotide is at least 90% complementary to an equal length portion of a FUS nucleic acid, and wherein the modified oligonucleotide comprises at least one modification selected from a modified sugar moiety and a modified internucleoside linkage.

Embodiment 2. An oligomeric compound comprising a modified oligonucleotide consisting of 12 to 50 linked nucleosides and having a nucleobase sequence comprising at least 8, 9, 10, 11, 12, 13, 14, 15, 16, 17, 18, 19, or 20 contiguous nucleobases of any of SEQ ID NOS: 12-480.

Embodiment 3. An oligomeric compound comprising a modified oligonucleotide consisting of 12 to 50 linked nucleosides and having a nucleobase sequence comprising at least 8, at least 9, at least 10, at least 11, at least 12, at least 13, at least 14, at least 15, at least 16, at least 17, at least 18, at least 19, or at least 20 contiguous nucleobases identical to SEQ ID NO: 12 or SEQ ID NO: 13.

Embodiment 4. An oligomeric compound comprising a modified oligonucleotide consisting of 20 linked nucleosides having a nucleobase sequence of SEQ ID NO: 12.

Embodiment 5. An oligomeric compound comprising a modified oligonucleotide consisting of 20 linked nucleosides having a nucleobase sequence of SEQ ID NO: 13.

Embodiment 6. An oligomeric compound comprising a modified oligonucleotide consisting of 12 to 50 linked nucleosides and having a nucleobase sequence comprising at least 8, at least 9, at least 10, at least 11, at least 12, at least 13, at least 14, at least 15, at least 16, at least 17, at least 18, at least 19, or at least 20 contiguous nucleobases complementary to an equal length portion of nucleobases 1,786 to 1,841 of SEQ ID NO: 1.

Embodiment 7. An oligomeric compound comprising a modified oligonucleotide consisting of 12 to 50 linked nucleosides and having a nucleobase sequence comprising at least 8, at least 9, at least 10, at least 11, at least 12, at least 13, at least 14, at least 15, at least 16, at least 17, at least 18, at least 19, or at least 20 contiguous nucleobases of any one of SEQ ID NOS: 34, 35, 111, 112, 188, 265, 342, and 418.

Embodiment 8. The oligomeric compound of any one of embodiments 1-7, wherein the modified oligonucleotide comprises a modified sugar moiety.

Embodiment 9. The oligomeric compound of any one of embodiments 1-7, wherein the modified oligonucleotide comprises a bicyclic sugar moiety.

Embodiment 10. The oligomeric compound of embodiment 9, wherein the bicyclic sugar moiety comprises a 2'-4' bridge selected from —O—$CH_2$—; and —O—CH($CH_3$)—.

Embodiment 11. The oligomeric compound of any one of embodiments 1-10, wherein the modified oligonucleotide comprises a non-bicyclic modified sugar moiety.

Embodiment 12. The oligomeric compound of embodiment 11, wherein the non-bicyclic modified sugar moiety comprises a 2'-MOE sugar moiety or 2'-OMe sugar moiety.

Embodiment 13. The oligomeric compound of any one of embodiments 1-12, wherein the modified oligonucleotide comprises a sugar surrogate.

Embodiment 14. The oligomeric compound of embodiment 13, wherein the sugar surrogate is selected from morpholino and PNA.

Embodiment 15. The oligomeric compound of any of embodiments 1-14, wherein the modified oligonucleotide has a sugar motif comprising: (a) a 5'-region consisting of 1-5 linked 5'-region nucleosides; (b) a central region consisting of 6-10 linked central region nucleosides; and (c) a 3'-region consisting of 1-5 linked 3'-region nucleosides, wherein each of the 5'-region nucleosides and each of the 3'-region nucleosides comprises a modified sugar moiety and each of the central region nucleosides comprises an unmodified 2'-deoxyribosyl sugar moiety.

Embodiment 16. The oligomeric compound of any one of embodiments 1-15, wherein the modified oligonucleotide comprises at least one modified internucleoside linkage.

Embodiment 17. The oligomeric compound of embodiment 16, wherein each internucleoside linkage of the modified oligonucleotide is a modified internucleoside linkage.

Embodiment 18. The oligomeric compound of embodiment 16 or 17, wherein the at least one modified internucleoside linkage is a phosphorothioate internucleoside linkage.

Embodiment 19. The oligomeric compound of any one of embodiments 16-18, wherein the modified oligonucleotide comprises at least one phosphodiester internucleoside linkage.

Embodiment 20. The oligomeric compound of embodiment 18 or 19, wherein each internucleoside linkage of the modified oligonucleotide is independently selected from a phosphodiester internucleoside linkage and a phosphorothioate internucleoside linkage.

Embodiment 21. The oligomeric compound of any one of embodiments 1-16, wherein the modified oligonucleotide consists essentially of 20 linked nucleosides and has an internucleoside linkage motif sooossssssssssooss, wherein "s" represents a phosphorothioate internucleoside linkage and "o" represents a phosphodiester internucleoside linkage.

Embodiment 22. The oligomeric compound of any one of embodiments 1-21, wherein the modified oligonucleotide comprises at least one modified nucleobase.

Embodiment 23. The oligomeric compound of embodiment 22, wherein the modified nucleobase is a 5-methyl cytosine.

Embodiment 24. An oligomeric compound comprising a modified oligonucleotide, wherein the modified oligonucleotide is a gapmer consisting of a 5' wing segment, a central gap segment, and a 3' wing segment, wherein: the 5' wing segment consists of five 2'-O-methoxyethyl nucleosides, the central gap segment consists of ten β-D-deoxyribonucleosides, and the 3' wing segment consists of five 2'-O-methoxyethyl nucleosides, wherein the modified oligonucleotide has the nucleobase sequence 5'-GTTTATCTGAATTCGCCATA-3' (SEQ ID NO. 12), wherein each cytosine is a 5-methylcytosine, wherein the internucleoside linkages of the modified oligonucleotide are soooossssssssssooss from 5' to 3', and wherein each s is a phosphorothioate linkage and each o is a phosphodiester linkage.

Embodiment 25. An oligomeric compound comprising a modified oligonucleotide, wherein the modified oligonucleotide is a gapmer consisting of a 5' wing segment, a central gap segment, and a 3' wing segment, wherein: the 5' wing segment consists of five 2'-O-methoxyethyl nucleosides, the central gap segment consists of ten β-D-deoxyribonucleosides, and the 3' wing segment consists of five 2'-O-methoxyethyl nucleosides, wherein the modified oligonucleotide has the nucleobase sequence 5'-GCAATGTCACCTTTCATACC-3' (SEQ ID NO. 13), wherein each cytosine is a 5-methylcytosine, wherein the internucleoside linkages of the modified oligonucleotide are soooossssssssssooss from 5' to 3', and wherein each s is a phosphorothioate linkage and each o is a phosphodiester linkage.

Embodiment 26. The oligomeric compound of any of embodiments 1-25, consisting essentially of the modified oligonucleotide.

Embodiment 27. The oligomeric compound of any of embodiments 1-25, consisting of the modified oligonucleotide.

Embodiment 28. The oligomeric compound of any of embodiments 1-25, comprising a conjugate group, wherein the conjugate group consists essentially of a conjugate moiety and a conjugate linker.

Embodiment 29. The oligomeric compound of embodiment 28, wherein the conjugate linker consists of a single bond.

Embodiment 30. The oligomeric compound of embodiment 28 or 29, wherein the conjugate linker is cleavable.

Embodiment 31. The oligomeric compound of any one of embodiments 28-30, wherein the conjugate linker comprises 1-3 linker-nucleosides.

Embodiment 32. The oligomeric compound of any one of embodiments 28-30, wherein the conjugate group does not comprise a nucleoside.

Embodiment 33. The oligomeric compound of any one of embodiments 28-32, wherein the conjugate group is attached to the modified oligonucleotide at the 5'-end of the modified oligonucleotide.

Embodiment 34. The oligomeric compound of any one of embodiments 28-32, wherein the conjugate group is attached to the modified oligonucleotide at the 3'-end of the modified oligonucleotide.

Embodiment 35. The oligomeric compound of any of embodiments 1-34 comprising a terminal group.

Embodiment 36. The oligomeric compound of any of embodiments 1-35, wherein the modified oligonucleotide is a singled-stranded modified oligonucleotide.

Embodiment 37. An oligomeric duplex comprising an oligomeric compound of any of embodiments 1-35.

Embodiment 38. An antisense compound comprising or consisting of an oligomeric compound of any of embodiments 1-36 or an oligomeric duplex of embodiment 37.

Embodiment 39. A modified oligonucleotide according to the following formula: Ges Teo Teo Teo Aeo Tds mCds Tds Gds Ads Ads Tds Tds mCds Gds mCeo mCeo Aes Tes Ae (SEQ ID NO: 12); wherein A=an adenine, mC=a 5'-methylcytosine, G=a guanine, T=a thymine, e=a 2'-O-methoxyethylribose modified sugar, d=a 2'-deoxyribose sugar, s=a phosphorothioate internucleoside linkage, and o=a phosphodiester internucleoside linkage.

Embodiment 40. A modified oligonucleotide according to the following formula: Ges Ceo Aeo Aeo Teo Gds Tds mCds Adsd mCds mCds Tds Tds Tds mCds Aeo Teo Aes mCes mCe (SEQ ID NO: 13); wherein, A=an adenine, mC=a 5'-methylcytosine, G=a guanine, T=a thymine, e=a 2'-O-methoxyethylribose modified sugar, d=a 2'-deoxyribose sugar, s=a phosphorothioate internucleoside linkage, and o=a phosphodiester internucleoside linkage.

Embodiment 41. A modified oligonucleotide according to the following chemical structure:

(SEQ ID NO. 12)

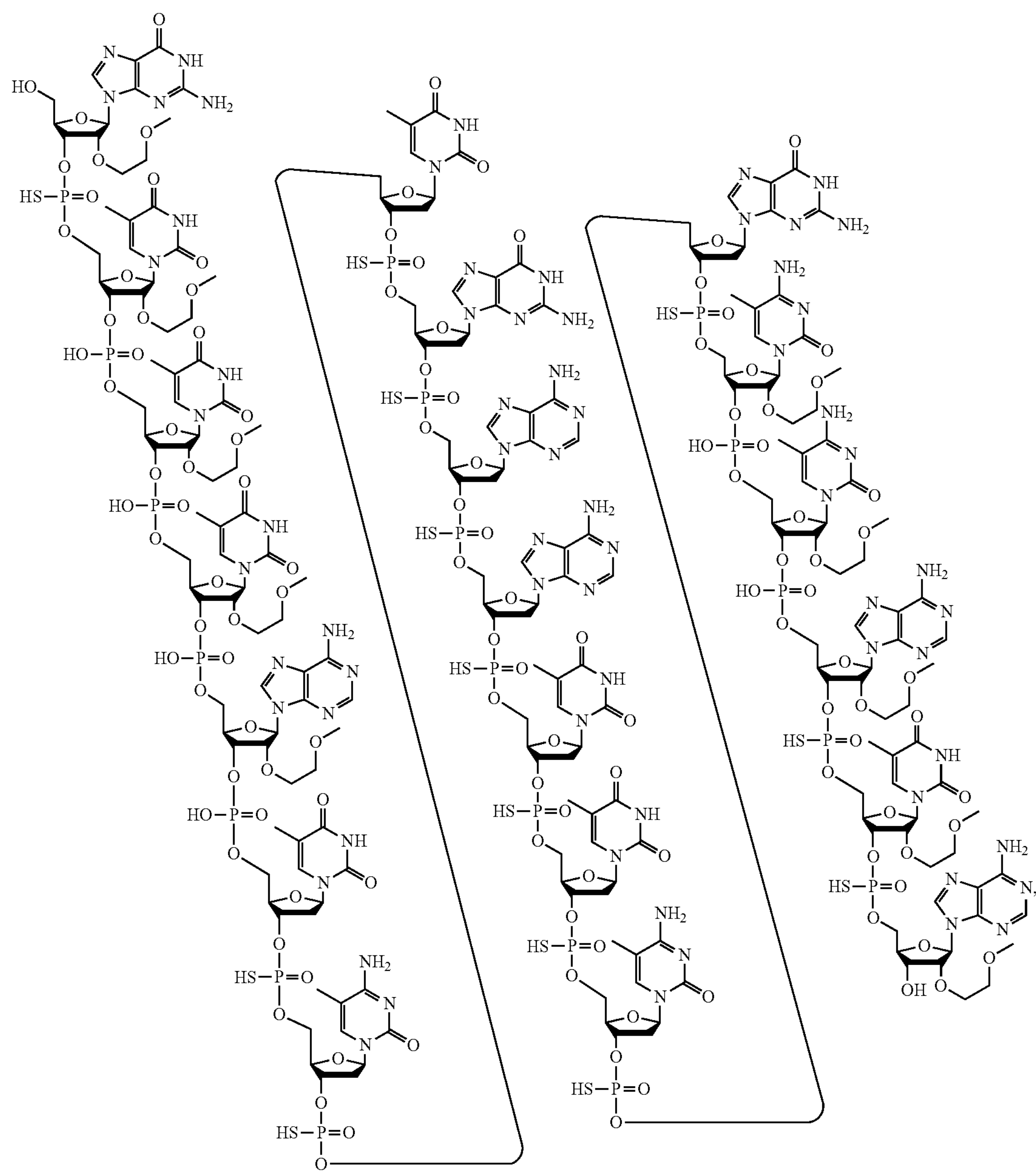

or a salt thereof.

Embodiment 42. The modified oligonucleotide of embodiment 41, which is the sodium salt or the potassium salt.

Embodiment 43. A modified oligonucleotide according to the following chemical structure:

(SEQ ID NO. 13)

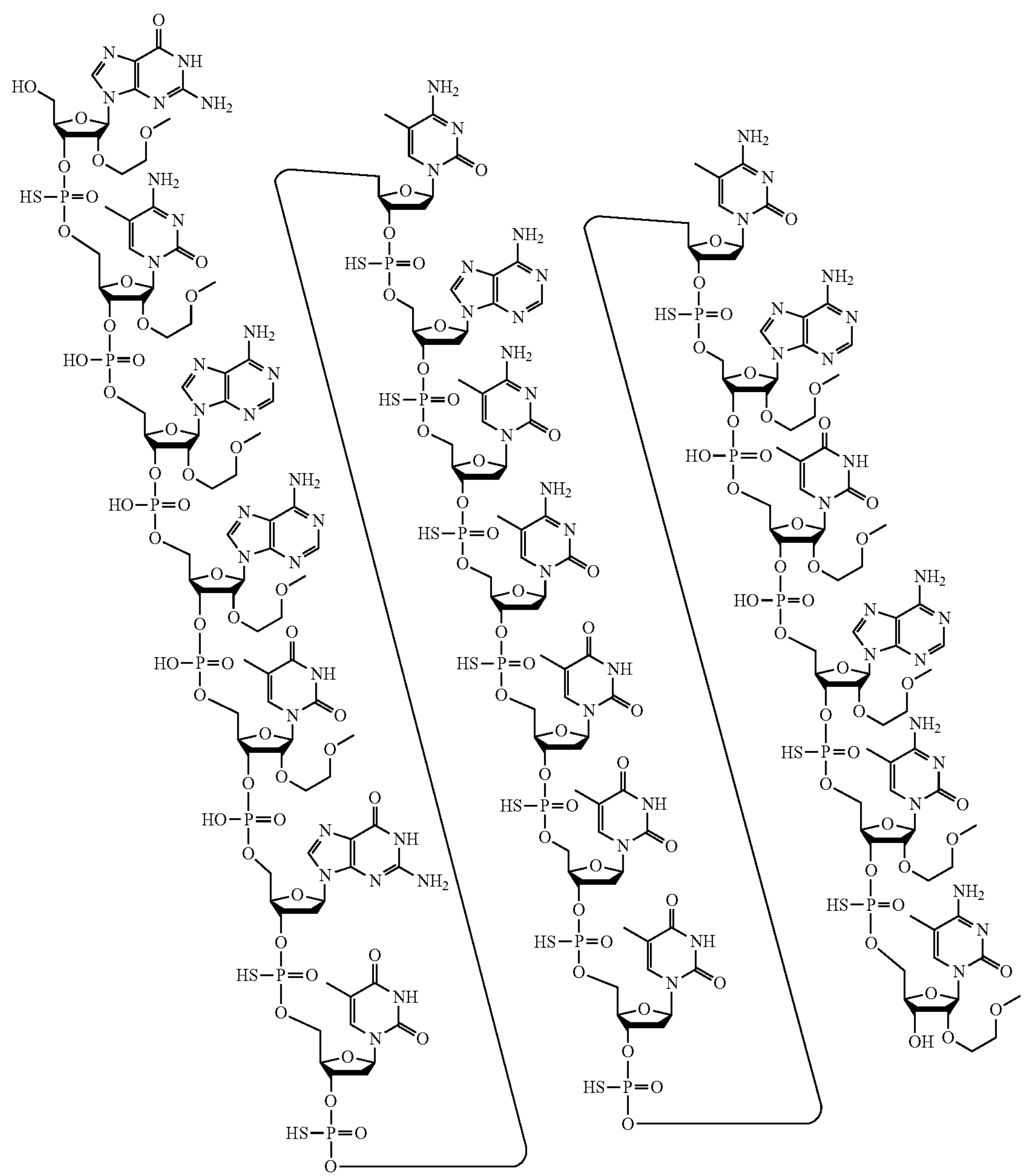

or a salt thereof.

Embodiment 44. The modified oligonucleotide of embodiment 43, which is the sodium salt or the potassium salt.

Embodiment 45. A modified oligonucleotide according to the following chemical structure:

(SEQ ID NO: 12)
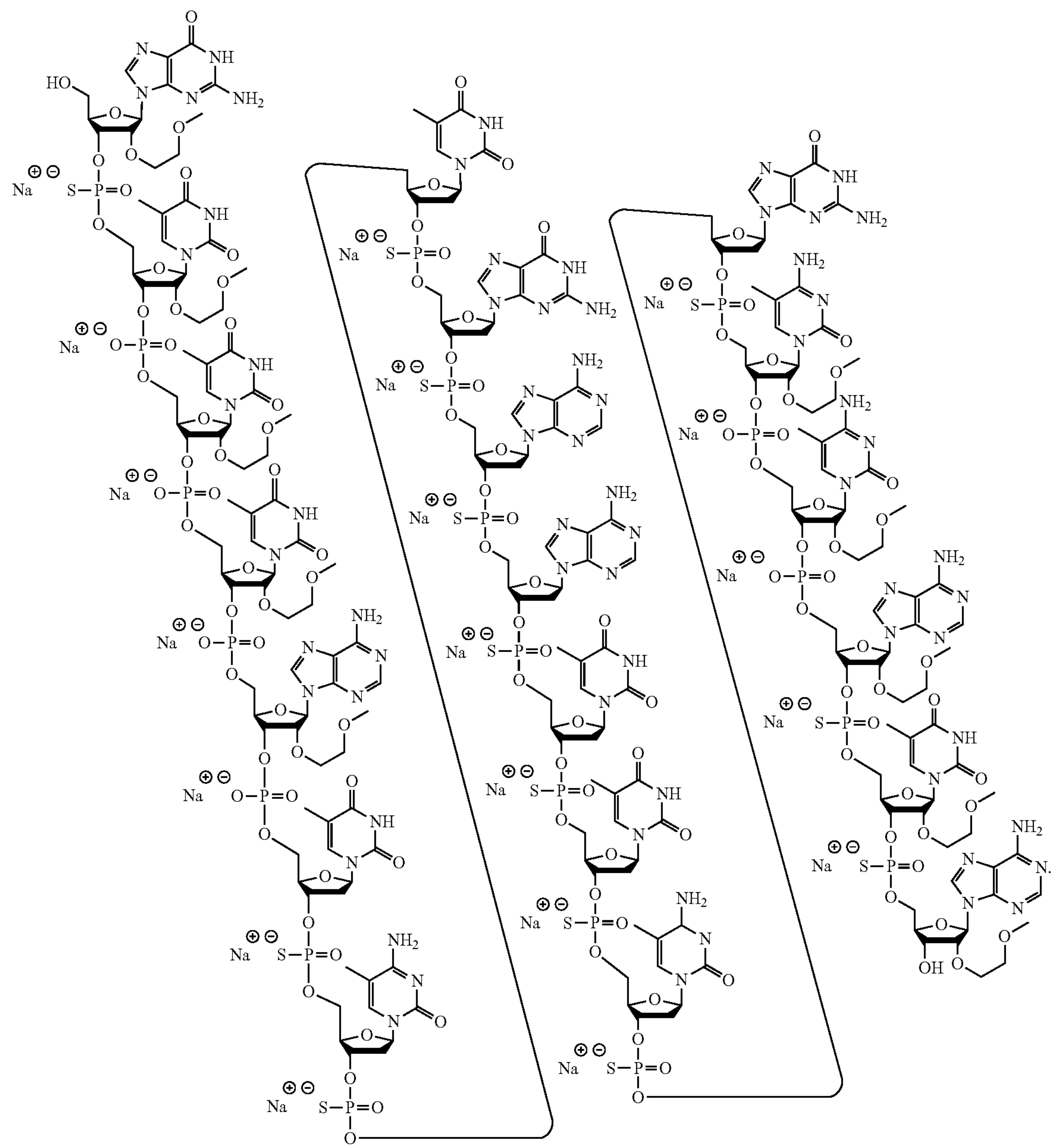
Embodiment 46. A modified oligonucleotide according to the following chemical structure:

(SEQ ID NO: 13)

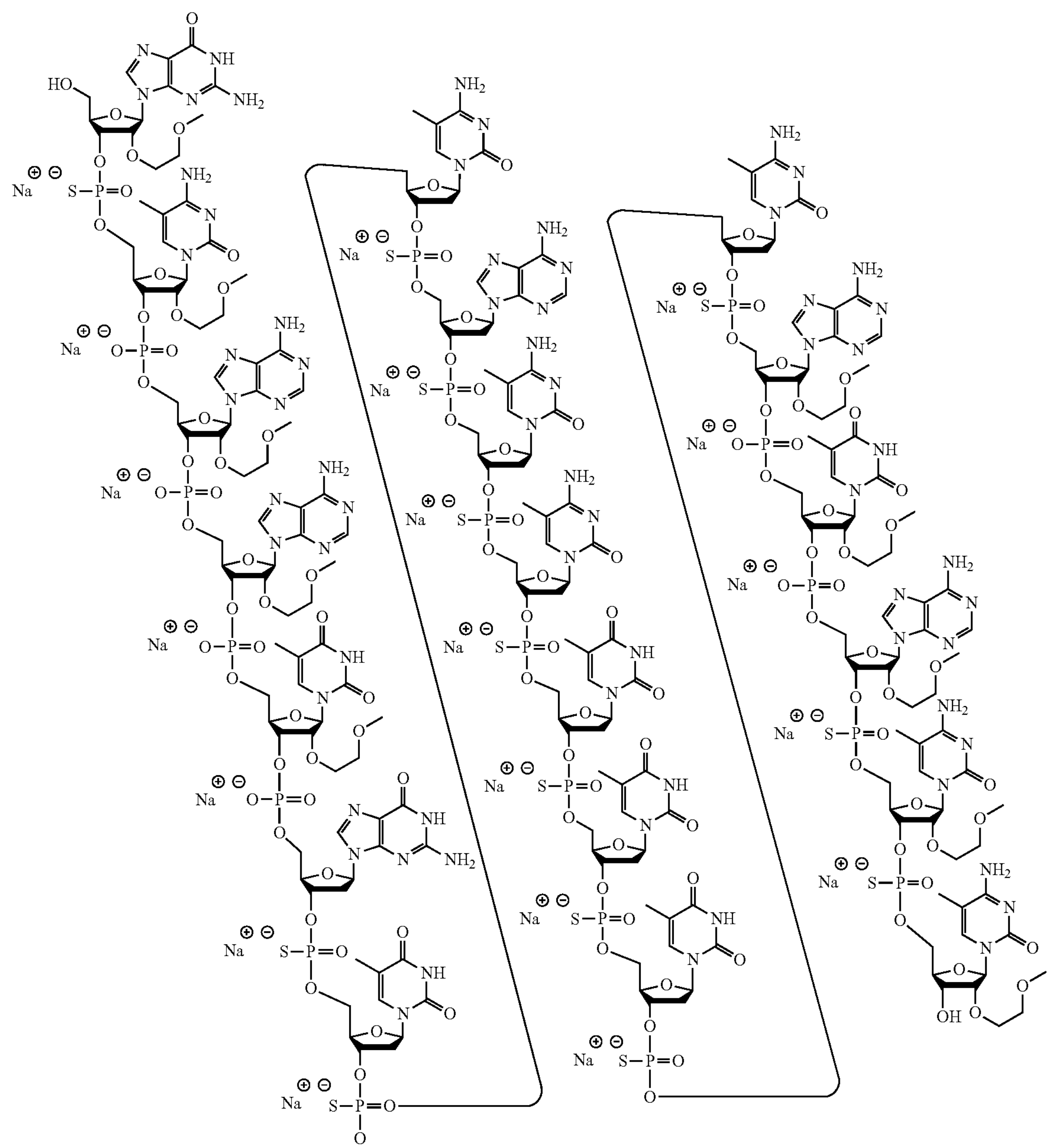

Embodiment 47. A pharmaceutical composition comprising at least one of the oligomeric compound of any of embodiments 1-36, the oligomeric duplex of embodiment 37, the antisense compound of embodiment 38, and the modified oligonucleotide of any one of embodiments 39-46; and a pharmaceutically acceptable carrier or diluent.

Embodiment 48. The pharmaceutical composition of embodiment 47, wherein the pharmaceutically acceptable diluent is artificial cerebrospinal fluid or phosphate buffered saline (PBS).

Embodiment 49. The pharmaceutical composition of embodiment 48, wherein the pharmaceutical composition consists essentially of the oligomeric compound, oligomeric duplex, antisense compound, or modified oligonucleotide; and artificial cerebrospinal fluid.

Embodiment 50. A method comprising administering to a subject at least one of the oligomeric compound of any of embodiments 1-36, the oligomeric duplex of embodiment 37, the antisense compound of embodiment 38, the modified oligonucleotide of any one of embodiments 39-46, and the pharmaceutical composition of any of embodiments 47-49.

Embodiment 51. A method of treating a neurodegenerative condition comprising administering to a subject having or at risk for developing the neurodegenerative condition a therapeutically effective amount of at least one of the oligomeric compound of any of embodiments 1-36, the oligomeric duplex of embodiment 37, the antisense compound of embodiment 38, the modified oligonucleotide of any one of embodiments 39-46, and the pharmaceutical composition of any of embodiments 47-49; thereby treating the neurodegenerative condition.

Embodiment 52. A method of reducing FUS RNA or FUS protein in the central nervous system of a subject having or at risk for developing a neurodegenerative condition comprising administering a therapeutically effective amount of at least one of the oligomeric compound of any of embodiments 1-36, the oligomeric duplex of embodiment 37, the antisense compound of embodiment 38, the modified oligonucleotide of any one of embodiments 39-46, and the pharmaceutical composition of any of embodiments 47-49, thereby reducing FUS RNA or FUS protein in the central nervous system.

Embodiment 53. The method of embodiment 51 or 52, wherein the neurodegenerative condition is amyotrophic lateral sclerosis (ALS).

Embodiment 54. The method of embodiment 51 or 52, wherein the neurodegenerative condition is frontotemporal lobar degeneration (FTLD).

Embodiment 55. The method of embodiment 51 or 52, wherein the neurodegenerative condition is FTLD-FUS.

Embodiment 56. The method of embodiment 51 or 52, wherein the neurodegenerative condition is ALS with FTLD.

Embodiment 57. A method of treating a neurodegenerative condition associated with a FUS mutation comprising identifying the FUS mutation in a subject and administering to the subject a therapeutically effective amount of at least one of the oligomeric compound of any of embodiments 1-36, the oligomeric duplex of embodiment 37, the antisense compound of embodiment 38, the modified oligonucleotide of any one of embodiments 39-46, and the pharmaceutical composition of any of embodiments 47-49.

Embodiment 58. The method of embodiment 57, wherein the FUS mutation is a single nucleotide polymorphism selected from rs121909667, rs121909668, rs121909669, rs121909671, rs186547381, rs267606831, rs267606832, rs267606833, rs387906627, rs387906628, rs387907274, rs752076094, rs764487847, rs886041389, rs886041390, rs886041577, rs886041776, rs1085308015, rs1161032867, rs1555509569, rs1555509609, rs1555509693, rs1596908744, rs1596912983, and rs121909668.

Embodiment 59. The method of embodiment 57, wherein the FUS mutation is selected from S57del, S96del, G156E, G171-174del, G174-175del, G187S, G191S, G206S, R216C, G225V, G230C, R234C, R234L, R244C, M254V, S402_P411delinsGGGG, S462F, G466VfsX14, Y484AfsX514, R495X, R495EfsX527, G497AfsX527, G507D, K510WfsX517, K510E, S513P, R514S, R514G, G515C, E516V, H517D, H517P, H517Q, R518G, R518K, Q519IfsX9, R521C, R521G, R521H, R521L, R521S, R522G, R524S, R524T, R524W, and P525L.

Embodiment 60. The method of embodiment 57, wherein identifying the FUS mutation comprises sequencing a FUS nucleic acid from the subject, or contacting the FUS nucleic acid from the subject with a nucleic acid probe that is complementary to a portion of the FUS nucleic acid comprising the mutation.

Embodiment 61. The method of any of embodiments 50-60, wherein the administering is by intrathecal administration.

Embodiment 62. The method of any of embodiments 55-61, wherein at least one symptom or hallmark of the neurodegenerative condition is ameliorated.

Embodiment 63. The method of embodiment 62, wherein the neurodegenerative condition is ALS and the at least one symptom or hallmark is selected from muscle weakness, muscle fatigue, slurred speech, twitching, cramping, protein aggregates in the central nervous system of the subject, and a combination thereof.

Embodiment 64. The method of embodiment 62, wherein the neurodegenerative condition is FTLD and the at least one symptom or hallmark is selected from speech difficulty and a behavioral abnormality.

Embodiment 65. The method of any of embodiments 50-64, wherein the method prevents or slows disease regression.

Embodiment 66. The method of any one of embodiments 50-65, wherein the subject is pre-symptomatic for the neurodegenerative condition.

Embodiment 67. The method of any one of embodiments 50-65, wherein the subject is symptomatic for the neurodegenerative condition.

Embodiment 68. The method of any one of embodiments 50-65, wherein the subject is prodromal for the neurodegenerative condition.

Embodiment 69. The method of any one of embodiments 51-68, wherein the therapeutically effective amount is 50 mg.

Embodiment 70. The method of any one of embodiments 51-68, wherein the therapeutically effective amount is 60 mg.

Embodiment 71. The method of any one of embodiments 51-68, wherein the therapeutically effective amount is 70 mg.

Embodiment 72. The method of any one of embodiments 51-68, wherein the therapeutically effective amount is 80 mg.

Embodiment 73. The method of any one of embodiments 51-68, wherein the therapeutically effective amount is 90 mg.

Embodiment 74. The method of any one of embodiments 51-68, wherein the therapeutically effective amount is 100 mg.

Embodiment 75. The method of any one of embodiments 51-68, wherein the therapeutically effective amount is 110 mg.

Embodiment 76. The method of any one of embodiments 51-68, wherein the therapeutically effective amount is 120 mg.

Embodiment 77. The method of any one of embodiments 51-68, wherein the therapeutically effective amount is 130 mg.

Embodiment 78. The method of any one of embodiments 51-68, wherein the therapeutically effective amount is 140 mg.

Embodiment 79. The method of any one of embodiments 51-68, wherein the therapeutically effective amount is 150 mg.

Embodiment 80. The method of any one of embodiments 51-68, wherein the therapeutically effective amount is 160 mg.

Embodiment 81. The method of any one of embodiments 51-68, wherein the therapeutically effective amount is 170 mg.

Embodiment 82. The method of any one of embodiments 51-68, wherein the therapeutically effective amount is 180 mg.

Embodiment 83. The method of any one of embodiments 51-68, wherein the therapeutically effective amount is 190 mg.

Embodiment 84. The method of any one of embodiments 51-68, wherein the therapeutically effective amount is 200 mg.

Embodiment 85. The method of any one of embodiments 51-68, wherein the therapeutically effective amount is about 50 mg.

Embodiment 86. The method of any one of embodiments 51-68, wherein the therapeutically effective amount is about 60 mg.

Embodiment 87. The method of any one of embodiments 51-68, wherein the therapeutically effective amount is about 70 mg.

Embodiment 88. The method of any one of embodiments 51-68, wherein the therapeutically effective amount is about 80 mg.

Embodiment 89. The method of any one of embodiments 51-68, wherein the therapeutically effective amount is about 90 mg.

Embodiment 90. The method of any one of embodiments 51-68, wherein the therapeutically effective amount is about 100 mg.

Embodiment 91. The method of any one of embodiments 51-68, wherein the therapeutically effective amount is about 110 mg.

Embodiment 92. The method of any one of embodiments 51-68, wherein the therapeutically effective amount is about 120 mg.

Embodiment 93. The method of any one of embodiments 51-68, wherein the therapeutically effective amount is about 130 mg.

Embodiment 94. The method of any one of embodiments 51-68, wherein the therapeutically effective amount is about 140 mg.

Embodiment 95. The method of any one of embodiments 51-68, wherein the therapeutically effective amount is about 150 mg.

Embodiment 96. The method of any one of embodiments 51-68, wherein the therapeutically effective amount is about 160 mg.

Embodiment 97. The method of any one of embodiments 51-68, wherein the therapeutically effective amount is about 170 mg.

Embodiment 98. The method of any one of embodiments 51-68, wherein the therapeutically effective amount is about 180 mg.

Embodiment 99. The method of any one of embodiments 51-68, wherein the therapeutically effective amount is about 190 mg.

Embodiment 100. The method of any one of embodiments 51-68, wherein the therapeutically effective amount is about 200 mg.

Embodiment 101. The method of any one of embodiments 51-68, wherein the therapeutically effective amount is any of 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, and 300 mg.

Embodiment 102. The method of any one of embodiments 51-68, wherein the therapeutically effective amount is any of about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, and about 300 mg.

Embodiment 103. The method of any one of embodiments 51-68, wherein the therapeutically effective amount is any of 115.0 mg, 115.1 mg, 115.2 mg, 115.3 mg, 115.4 mg, 115.5 mg, 115.6 mg, 115.7 mg, 115.8 mg, 115.9 mg, 116.0 mg, 116.1 mg, 116.2 mg, 116.3 mg, 116.4 mg, 116.5 mg, 116.6 mg, 116.7 mg, 116.8 mg, 116.9 mg, 117.0 mg, 117.1 mg, 117.2 mg, 117.3 mg, 117.4 mg, 117.5 mg, 117.6 mg, 117.7 mg, 117.8 mg, 117.9 mg, 118.0 mg, 118.1 mg, 118.2 mg, 118.3 mg. 118.4 mg, 118.5 mg, 118.6 mg, 118.7 mg, 118.8 mg, 118.9 mg, 119.0 mg, 119.1 mg, 119.2 mg, 119.3 mg, 119.4 mg, 119.5 mg, 119.6 mg, 119.7 mg, 119.8 mg, 119.9 mg, 120.0 mg, 120.1 mg, 120.2 mg, 120.3 mg. 120.4 mg, 120.5 mg, 120.6 mg, 120.7 mg, 120.8 mg, 120.9 mg, 121.0 mg, 121.1 mg, 121.2 mg, 121.3 mg, 121.4 mg, 121.5 mg, 121.6 mg, 121.7 mg, 121.8 mg, 121.9 mg, 122.0 mg, 122.1 mg, 122.2 mg, 122.3 mg. 122.4 mg, 122.5 mg, 122.6 mg, 122.7 mg, 122.8 mg, 122.9 mg, 123.0 mg, 123.1 mg, 123.2 mg, 123.3 mg, 123.4 mg, 123.5 mg, 123.6 mg, 123.7 mg, 123.8 mg, 123.9 mg, 124.0 mg, 124.1 mg, 124.2 mg, 124.3 mg. 124.4 mg, 124.5 mg, 124.6 mg, 124.7 mg, 124.8 mg, 124.9 mg, and 125.0 mg.

Embodiment 104. The method of any one of embodiments 51-68, wherein the therapeutically effective amount is any of about 115.0 mg, about 115.1 mg, about 115.2 mg, about 115.3 mg, about 115.4 mg, about 115.5 mg, about 115.6 mg, about 115.7 mg, about 115.8 mg, about 115.9 mg, about 116.0 mg, about 116.1 mg, about 116.2 mg, about 116.3 mg, about 116.4 mg, about 116.5 mg, about 116.6 mg, about 116.7 mg, about 116.8 mg, about 116.9 mg, about 117.0 mg, about 117.1 mg, about 117.2 mg, about 117.3 mg, about 117.4 mg, about 117.5 mg, about 117.6 mg, about 117.7 mg, about 117.8 mg, about 117.9 mg, about 118.0 mg, about 118.1 mg, about 118.2 mg, about 118.3 mg. 118.4 mg, about 118.5 mg, about 118.6 mg, about 118.7 mg, about 118.8 mg, about 118.9 mg, about 119.0 mg, about 119.1 mg, about 119.2 mg, about 119.3 mg, about 119.4 mg, about 119.5 mg, about 119.6 mg, about 119.7 mg, about 119.8 mg, about 119.9 mg, about 120.0 mg, about 120.1 mg, about 120.2 mg, about 120.3 mg. 120.4 mg, about 120.5 mg, about 120.6 mg, about 120.7 mg, about 120.8 mg, about 120.9 mg, about 121.0 mg, about 121.1 mg, about 121.2 mg, about 121.3 mg, about 121.4 mg, about 121.5 mg, about 121.6 mg, about 121.7 mg, about 121.8 mg, about 121.9 mg, about 122.0 mg, about 122.1 mg, about 122.2 mg, about 122.3 mg. 122.4 mg, about 122.5 mg, about 122.6 mg, about 122.7 mg, about 122.8 mg, about 122.9 mg, about 123.0 mg, about 123.1 mg, about 123.2 mg, about 123.3 mg, about 123.4 mg, about 123.5 mg, about 123.6 mg, about 123.7 mg, about 123.8 mg, about 123.9 mg, about 124.0 mg, about 124.1 mg, about 124.2 mg, about 124.3 mg. 124.4 mg, about 124.5 mg, about 124.6 mg, about 124.7 mg, about 124.8 mg, about 124.9 mg, and about 125.0 mg.

Embodiment 105. The method of any one of embodiments 51-68, wherein the therapeutically effective amount is any of 95.0 mg, 95.1 mg, 95.2 mg, 95.3 mg, 95.4 mg, 95.5 mg, 95.6 mg, 95.7 mg, 95.8 mg, 95.9 mg, 96.0 mg, 96.1 mg, 96.2 mg, 96.3 mg, 96.4 mg, 96.5 mg, 96.6 mg, 96.7 mg, 96.8 mg, 96.9 mg, 97.0 mg, 97.1 mg, 97.2 mg, 97.3 mg, 97.4 mg, 97.5 mg, 97.6 mg, 97.7 mg, 97.8 mg, 97.9 mg, 98.0 mg, 98.1 mg, 98.2 mg, 98.3 mg. 98.4 mg, 98.5 mg, 98.6 mg, 98.7 mg, 98.8 mg, 98.9 mg, 99.0 mg, 99.1 mg, 99.2 mg, 99.3 mg, 99.4 mg, 99.5 mg, 99.6 mg, 99.7 mg, 99.8 mg, 99.9 mg, 100.0 mg, 100.1 mg, 100.2 mg, 100.3 mg. 100.4 mg, 100.5 mg, 100.6 mg, 100.7 mg, 100.8 mg, 100.9 mg, 101.0 mg, 101.1 mg, 101.2 mg, 101.3 mg, 101.4 mg, 101.5 mg, 101.6 mg, 101.7 mg, 101.8 mg, 101.9 mg, 102.0 mg, 102.1 mg, 102.2 mg, 102.3 mg. 102.4 mg, 102.5 mg, 102.6 mg, 102.7 mg, 102.8 mg, 102.9 mg, 103.0 mg, 103.1 mg, 103.2 mg, 103.3 mg, 103.4 mg, 103.5 mg, 103.6 mg, 103.7 mg, 103.8 mg, 103.9 mg, 104.0 mg, 104.1 mg, 104.2 mg, 104.3 mg. 104.4 mg, 104.5 mg, 104.6 mg, 104.7 mg, 104.8 mg, 104.9 mg, and 105.0 mg.

Embodiment 106. The method of any one of embodiments 51-68, wherein the therapeutically effective amount is any of about 95.0 mg, about 95.1 mg, about 95.2 mg, about 95.3 mg, about 95.4 mg, about 95.5 mg, about 95.6 mg, about 95.7 mg, about 95.8 mg, about 95.9 mg, about 96.0 mg, about 96.1 mg, about 96.2 mg, about 96.3 mg, about 96.4 mg, about 96.5 mg, about 96.6 mg, about 96.7 mg, about 96.8 mg, about 96.9 mg, about 97.0 mg, about 97.1 mg, about 97.2 mg, about 97.3 mg, about 97.4 mg, about 97.5 mg, about 97.6 mg, about 97.7 mg, about 97.8 mg, about 97.9 mg, about 98.0 mg, about 98.1 mg, about 98.2 mg, about 98.3 mg. 98.4 mg, about 98.5 mg, about 98.6 mg, about 98.7 mg, about 98.8 mg, about 98.9 mg, about 99.0 mg, about 99.1 mg, about 99.2 mg, about 99.3 mg, about 99.4 mg, about 99.5 mg, about 99.6 mg, about 99.7 mg, about 99.8 mg, about 99.9 mg, about 100.0 mg, about 100.1 mg, about 100.2 mg, about 100.3 mg. 100.4 mg, about 100.5 mg, about 100.6 mg, about 100.7 mg, about 100.8 mg, about 100.9 mg, about 101.0 mg, about 101.1 mg, about 101.2 mg, about 101.3 mg, about 101.4 mg, about 101.5 mg, about 101.6 mg, about 101.7 mg, about 101.8 mg, about 101.9 mg, about 102.0 mg, about 102.1 mg, about 102.2 mg, about 102.3 mg. 102.4 mg, about 102.5 mg, about 102.6 mg, about 102.7 mg, about 102.8 mg, about 102.9 mg, about 103.0 mg, about 103.1 mg, about 103.2 mg, about 103.3 mg, about 103.4 mg, about 103.5 mg, about 103.6 mg, about 103.7 mg, about 103.8 mg, about 103.9 mg, about 104.0 mg, about 104.1 mg, about 104.2 mg, about 104.3 mg. 104.4 mg, about 104.5 mg, about 104.6 mg, about 104.7 mg, about 104.8 mg, about 104.9 mg, and about 105.0 mg.

Embodiment 107. The method of any one of embodiments 51-68, wherein the therapeutically effective amount is within the range of any of 40 mg to 200 mg, 40 mg to 190 mg, 40 mg to 180 mg, 40 mg to 170 mg, from 40 mg to 160 mg, 40 mg to 150 mg, 40 mg to 140 mg, 40 mg to 120 mg, 40 mg to 110 mg, 40 mg to 100 mg, 40 mg to 80 mg, 40 mg to 70 mg, 40 mg to 60 mg, 40 mg to 50 mg, 50 mg to 200 mg, 50 mg to 190 mg, 50 mg to 180 mg, 50 mg to 170 mg, 50 mg to 160 mg, 50 mg to 150 mg, 50 mg to 140 mg, 50 mg to 120 mg, 50 mg to 110 mg, 50 mg to 100 mg, 50 mg to 80 mg, 50 mg to 70 mg, 50 mg to 60 mg, 60 mg to 200 mg, 60 mg to 190 mg, 60 mg to 180 mg, 60 mg to 170 mg, 60 mg to 160 mg, 60 mg to 150 mg, 60 mg to 140 mg, 60 mg to 120 mg, 60 mg to 110 mg, 60 mg to 100 mg, 60 mg to 80 mg, 60 mg to 70 mg, 70 mg to 200 mg, 70 mg to 190 mg, 70 mg to 180 mg, 70 mg to 170 mg, 70 mg to 160 mg, 70 mg to 150 mg, 70 mg to 140 mg, 70 mg to 120 mg, 70 mg to 110 mg, 70 mg to 100 mg, 70 mg to 80 mg, 80 mg to 200 mg, 80 mg to 190 mg, 80 mg to 180 mg, 80 mg to 170 mg, 80 mg to 160 mg, 80 mg to 150 mg, 80 mg to 140 mg, 80 mg to 120 mg, 80 mg to 110 mg, 80 mg to 100 mg, 80 mg to 90 mg, 90 mg to 200 mg, 90 mg to 190 mg, 90 mg to 180 mg, 90 mg to 170 mg, 90 mg to 160 mg, 90 mg to 150 mg, 90 mg to 140 mg, 90 mg to 120 mg, 90 mg to 110 mg, 90 mg to 100 mg, 100 mg to 200 mg, 100 mg to 190 mg, 100 mg to 180 mg, 100 mg to 170 mg, 100 mg to 160 mg, 100 mg to 150 mg, 100 mg to 140 mg, 100 mg to 120 mg, 100 mg to 110 mg, 110 mg to 200 mg, 110 mg to 190 mg, 110 mg to 180 mg, 110 mg to 170 mg, 110 mg to 160 mg, 110 mg to 150 mg, 110 mg to 140 mg, 110 mg to 130 mg, 110 mg to 120 mg, 120 mg to 200 mg, 120 mg to 190 mg, 120 mg to 180 mg, 120 mg to 170 mg, 120 mg to 160 mg, 120 mg to 150 mg, 120 mg to 140 mg, 120 mg to 130 mg, 130 mg to 200 mg, 130 mg to 190 mg, 130 mg to 180 mg, 130 mg to 170 mg, 130 mg to 160 mg, 130 mg to 150 mg, 130 mg to 140 mg, 140 mg to 200 mg, 140 mg to 190 mg, 140 mg to 180 mg, 140 mg to 170 mg, 140 mg to 160 mg, 140 mg to 150 mg, 150 mg to 200 mg, 150 mg to 190 mg, 150 mg to 180 mg, 150 mg to 170 mg, 150 mg to 160 mg, 160 mg to 200 mg, 160 mg to 190 mg, 160 mg to 180 mg, 160 mg to 170 mg, 180 mg to 200 mg, 180 mg to 190 mg, 190 mg to 200 mg, 105 mg to 135 mg, 105 mg to 130 mg, 105 mg to 125 mg 105 mg to 120 mg, 110 mg to 135 mg, 110 mg to 130 mg, 110 mg to 125 mg, 110 mg to 120 mg, 115 mg to 135 mg, 115 mg to 130 mg, 115 mg to 125 mg, 115 mg to 120 mg, 115 mg to 125 mg, 115 mg to 120 mg, 120 mg to 135 mg, 120 mg to 125 mg, 125 mg to 140 mg, 125 mg to 130 mg, 130 mg to 135 mg, 135 mg to 140 mg, 120 mg to 129 mg, 120 mg to 128 mg, 120 mg to 127 mg, 120 mg to 86 mg, 120 mg to 124 mg, 120 mg to 123 mg, 120 mg to 122 mg, 120 mg to 121 mg, 121 mg to 130 mg, 122 mg to 129 mg, 122 mg to 128 mg, 122 mg to 127 mg, 122 mg to 126 mg, 122 mg to 125 mg, 122 mg to 124 mg, 122 mg to 123 mg, 123 mg to 130 mg, 123 mg to 129 mg, 123 mg to 128 mg, 123 mg to 127 mg, 123 mg to 126 mg, 123 mg to 125 mg, 123 mg to 124 mg, 124 mg to 130 mg, 124 mg to 129 mg, 124 mg to 128 mg, 124 mg to 127 mg, 124 mg to 126 mg, 124 mg to 125 mg, 125 mg to 129 mg, 125 mg to 128 mg, 125 mg to 127 mg, 125 mg to 126 mg, 126 mg to 130 mg, 126 mg to 129 mg, 126 mg to 128 mg, 126 mg to 127 mg, 127 mg to 130 mg, 127 mg to 129 mg, 127 mg to 128 mg, 128 mg to 130 mg, 128 mg to 129 mg, and 129 mg to 130 mg.

Embodiment 108. The method of any one of embodiments 51-68, wherein the therapeutically effective amount is any of less than 300 mg, less than 295 mg, less than 290 mg, less than 285 mg, less than 280 mg, less than 275 mg, less than 270 mg, less than 265 mg, less than 260 mg, less than 255 mg, less than 250 mg, less than 245 mg, less than 240 mg, less than 235 mg, less than 230 mg, less than 225 mg, less than 220 mg, less than 215 mg, less than 210 mg, less than 205 mg, less than 200 mg, less than 195 mg, less than 190 mg, less than 185 mg, less than 180 mg, less than 175 mg, less than 170 mg, less than 165 mg, less than 160 mg, less than 150 mg, less than 145 mg, less than 140 mg, less than 135 mg, less than 130 mg, less than 125 mg, less than 120 mg, less than 115 mg, less than 110 mg, less than 105 mg, less than 100 mg, less than 95 mg, less than 90 mg, less than 85 mg, less than 80 mg, less than 75 mg, less than 70 mg, less than 65 mg, less than 60 mg, less than 55 mg, less than 50 mg, less than 45 mg, less than 40 mg, less than 35 mg, less than 30 mg, less than 25 mg, less than 20 mg, less than 15 mg, less than 10 mg, and less than 5 mg.

Embodiment 109. The method of any one of embodiments 51-68, wherein the therapeutically effective amount is any of less than about 300 mg, less than about 295 mg, less than about 290 mg, less than about 285 mg, less than about 280 mg, less than about 275 mg, less than about 270 mg, less than about 265 mg, less than about 260 mg, less than about 255 mg, less than about 250 mg, less than about 245 mg, less than about 240 mg, less than about 235 mg, less than about 230 mg, less than about 225 mg, less than about 220 mg, less than about 215 mg, less than about 210 mg, less than about 205 mg, less than about 200 mg, less than about 195 mg, less than about 190 mg, less than about 185 mg, less than about 180 mg, less than about 175 mg, less than about 170 mg, less than about 165 mg, less than about 160 mg, less than about 150 mg, less than about 145 mg, less than about 140 mg, less than about 135 mg, less than about 130 mg, less than about 125 mg, less than about 120 mg, less than about 115 mg, less than about 110 mg, less than about 105 mg, less than about 100 mg, less than about 95 mg, less than about 90 mg, less than about 85 mg, less than about 80 mg, less than about 75 mg, less than about 70 mg, less than about 65 mg, less than about 60 mg, less than about 55 mg, less than about 50 mg, less than about 45 mg, less than about 40 mg, less than about 35 mg, less than about 30 mg, less than about 25 mg, less than about 20 mg, less than about 15 mg, less than about 10 mg, and less than about 5 mg.

Embodiment 110. The method of any one of embodiments 51-68, wherein the therapeutically effective amount is any of at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least about 100 mg, at least 105 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185, at least 190 mg, at least 195 mg, and at least 200 mg.

Embodiment 111. The method of any one of embodiments 51-68, wherein the therapeutically effective amount is any of at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 115 mg, at least about 120 mg, at least about 125 mg, at least about 130 mg, at least about 135 mg, at least about 140 mg, at least about 145 mg, or at least about 150 mg, at least about 155 mg, at least about 160 mg, at least about 165 mg, at least about 170 mg, at least about 175 mg, at least about 180 mg, at least about 185, at least about 190 mg, at least about 195 mg, and at least about 200 mg.

Embodiment 112. The method of any one of embodiments 51-111, comprising administering the modified oligonucleotide once every 4 weeks.

Embodiment 113. The method of any one of embodiments 51-111, comprising administering the modified oligonucleotide once every 8 weeks.

Embodiment 114. The method of any one of embodiments 51-111, comprising administering the modified oligonucleotide once every 12 weeks.

Embodiment 115. The method of any one of embodiments 51-111, comprising administering the modified oligonucleotide once every 16 weeks.

Embodiment 116. The method of any one of embodiments 51-111, comprising administering the modified oligonucleotide about once every 4 weeks.

Embodiment 117. The method of any one of embodiments 51-111, comprising administering the modified oligonucleotide about once every 8 weeks.

Embodiment 118. The method of any one of embodiments 51-111, comprising administering the modified oligonucleotide about once every 12 weeks.

Embodiment 119. The method of any one of embodiments 51-111, comprising administering the modified oligonucleotide about once every 16 weeks.

Embodiment 120. The method of any one of embodiments 51-111, comprising administering the modified oligonucleotide any of once every 1 week, once every 2 weeks, once every 3 weeks, once every 4 weeks, once every 5 weeks, once every 6 weeks, once every 7 weeks, once every 8 weeks, once every 9 weeks, once every 10 weeks, once every 11 weeks, once every 12 weeks, once every 13 weeks, once every 14 weeks, once every 15 weeks, once every 16 weeks, once every 17 weeks, once every 18 weeks, once every 19 weeks, and once every 20 weeks.

Embodiment 121. The method of any one of embodiments 51-111, comprising administering the modified oligonucleotide any of once about every 1 week, once about every 2 weeks, once about every 3 weeks, once about every 4 weeks, once about every 5 weeks, once about every 6 weeks, once about every 7 weeks, once about every 8 weeks, once about every 9 weeks, once about every 10 weeks, once about every 11 weeks, once about every 12 weeks, once about every 13 weeks, once about every 14 weeks, once about every 15 weeks, once about every 16 weeks, once about every 17 weeks, once about every 18 weeks, once about every 19 weeks, and once about every 20 weeks.

Embodiment 122. A method of reducing FUS RNA in a cell comprising contacting the cell with at least one of the oligomeric compound of any of embodiments 1-36, the oligomeric duplex of embodiment 37, the antisense compound of embodiment 38, and the modified oligonucleotide of any one of embodiments 39-46, thereby reducing FUS RNA in the cell.

Embodiment 123. A method of reducing FUS protein in a cell comprising contacting the cell with at least one of the oligomeric compound of any of embodiments 1-36, the oligomeric duplex of embodiment 37, the antisense compound of embodiment 38, and the modified oligonucleotide of any one of embodiments 39-46, thereby reducing FUS protein in the cell.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non-bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-$OCH_3$ ("OMe" or "O-methyl"), and 2'-$O(CH_2)_2OCH_3$ ("MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted non-bicyclic modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)—N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside non-bicyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)—N(H)CH_3$ ("NMA").

In certain embodiments, a 2'-substituted non-bicyclic modified nucleoside comprises a sugar moiety comprising a non-bridging 2'-substituent group selected from: F, $OCH_3$, and $OCH_2CH_2OCH_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt"), 4'-$CH_2$—O—$CH_2$-2', 4'-$CH_2$—N(R)-2', 4'-CH($CH_2OCH_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—$N(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—$C(H)(CH_3)$-2' (see, e.g., Zhou, et al., *J Org. Chem.,* 2009, 74, 118-134), 4'-$CH_2$—$C(=CH_2)$-2' and analogs thereof (see e.g., Seth et al., U.S. Pat. No. 8,278,426), 4'-$C(R_aR_b)$—N(R)—O-2', 4'-$C(R_aR_b)$—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —$C(R_a)=C(R_b)$—, —$C(R_a)=N$—, —$C(=NR_a)$—, —C(=O)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research,* 1997, 25(22), 4429-4443, Albaek et al., *J Org. Chem.,* 2006, 71, 7731-7740, Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J Org. Chem.,* 1998, 63, 10035-10039; Srivastava et al., *J. Am. Chem. Soc.,* 2007, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

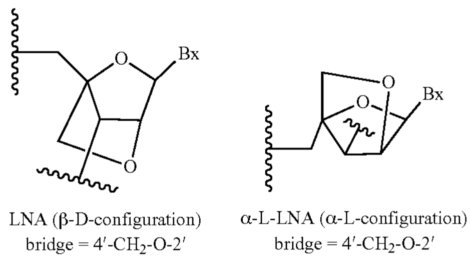

LNA (β-D-configuration) bridge = 4'-$CH_2$-O-2'    α-L-LNA (α-L-configuration) bridge = 4'-$CH_2$-O-2'

α-L-methyleneoxy (4'-$CH_2$—O-2') or α-L-LNA bicyclic nucleosides have been incorporated into oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("INA") (see, e.g., Leumann, C J. *Bioorg. & Med. Chem.* 2002, 10, 841-854), fluoro HNA:

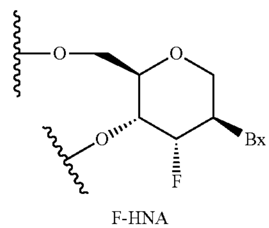

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

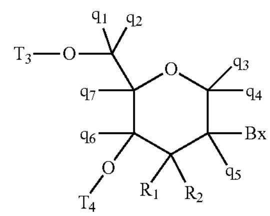

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

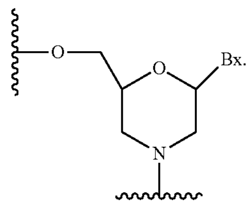

In certain embodiments, morpholinos may be modified, for example by adding or altering various substituent groups from the above morpholino structure. Such sugar surrogates are referred to herein as "modifed morpholinos."

In certain embodiments, sugar surrogates comprise acyclic moieites. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.,* 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($-C{\equiv}C-CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15*, Antisense Research and Applications*, Crooke, S. T. and Lebleu, B., Eds., CRC Press, 1993, 273-288; and those disclosed in Chapters 6 and 15*, Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino ($—CH_2—N(CH_3)—O—CH_2—$), thiodiester, thionocarbamate (—O—C(═O)(NH)—S—); siloxane ($—O—SiH_2—O—$); and N,N'-dimethylhydrazine ($—CH_2—N(CH_3)—N(CH_3)—$). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

($R_p$)

($S_p$)

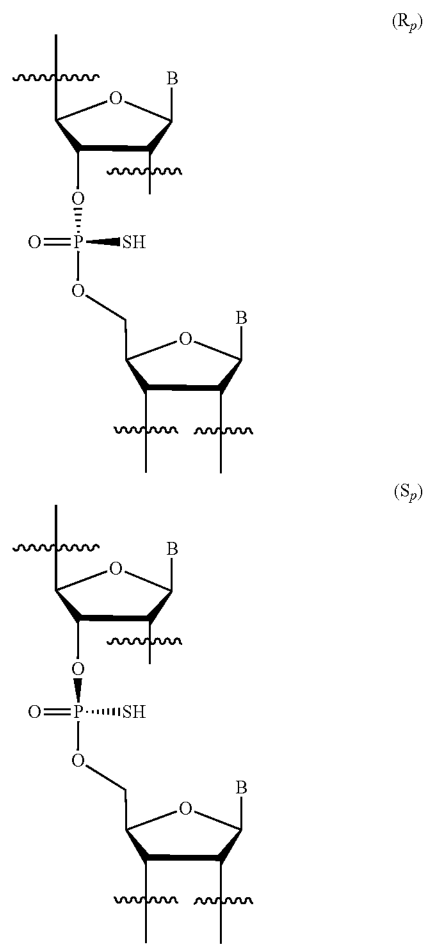

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—N($CH_3$)—O-5'), amide-3 (3'-$CH_2$—C(═O)—N(H)-5'), amide-4 (3'-$CH_2$—N(H)—C(═O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., *ACS Symposium Series* 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or “wings” and a central or internal region or “gap.” The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5-wing differs from the sugar motif of the 3-wing (asymmetric gapmer).

In certain embodiments, the wings of a gapmer comprise 1-5 nucleosides. In certain embodiments, each nucleoside of each wing of a gapmer is a modified nucleoside. In certain embodiments, at least one nucleoside of each wing of a gapmer is a modified nucleoside. In certain embodiments, at least two nucleosides of each wing of a gapmer are modified nucleosides. In certain embodiments, at least three nucleosides of each wing of a gapmer are modified nucleosides. In certain embodiments, at least four nucleosides of each wing of a gapmer are modified nucleosides.

In certain embodiments, the gap of a gapmer comprises 7-12 nucleosides. In certain embodiments, each nucleoside of the gap of a gapmer is an unmodified 2'-deoxynucleoside. In certain embodiments, at least one nucleoside of the gap of a gapmer is a modified nucleoside.

In certain embodiments, the gapmer is a deoxy gapmer. In certain embodiments, the nucleosides on the gap side of each wing/gap junction are unmodified 2'-deoxynucleosides and the nucleosides on the wing sides of each wing/gap junction are modified nucleosides. In certain embodiments, each nucleoside of the gap is an unmodified 2'-deoxynucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprise unmodified deoxynucleosides sugars. Thus, a 5-10-5 MOE gapmer consists of 5 linked MOE modified nucleosides in the 5'-wing, 10 linked deoxynucleosides in the gap, and 5 linked MOE nucleosides in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P═O). In certain embodiments, each internucleoside linking group of a modified oligonucleotide is a phosphorothioate internucleoside linkage (P═S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

D. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for R-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

E. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

B. Certain Terminal Groups

In certain embodiments, oligomeric compounds comprise one or more terminal groups. In certain such embodiments, oligomeric compounds comprise a stabilized 5'-phophate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or subject.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. FUS

In certain embodiments, oligomeric compounds comprise or consist of an oligonucleotide comprising a region that is complementary to a FUS nucleic acid. In certain embodiments, the FUS nucleic acid has the sequence set forth in SEQ ID NO: 1 (GENBANK Accession No: NM_004960.3). In certain embodiments, the FUS nucleic acid has the sequence set forth in SEQ ID NO: 2 (GENBANK Accession No: NC_000016.10 truncated from nucleotides 31176001 to 31198000).

In certain embodiments an oligomeric compound complementary to SEQ ID NO: 1 or SEQ ID NO: 2 is capable of reducing a FUS RNA in a cell. In certain embodiments an oligomeric compound complementary to SEQ ID NO: 1 or SEQ ID NO: 2 is capable of reducing a FUS protein in a cell. In certain embodiments, the cell is in vitro. In certain embodiments, the cell is in a subject. In certain embodiments, the oligomeric compound consists of a modified oligonucleotide. In certain embodiments, an oligomeric compound complementary to SEQ ID NO: 1 or SEQ ID NO: 2 is capable of ameliorating one or more symptom or hallmark of a neurodegenerative condition when it is introduced to a cell in a subject. Exemplary symptoms and hallmarks of ALS include, but are not limited to, muscle weakness and fatigue, slurred speech, twitching, cramping, and protein aggregates in the CNS. Exemplary symptoms and hallmarks of FTLD include, but are not limited to, speech difficulties and behavioral abnormalities.

In certain embodiments, an oligomeric compound complementary to SEQ ID NO: 1 or SEQ ID NO: 2 is capable of reducing a detectable amount of FUS RNA in the CSF of a subject when the oligomeric compound is administered to the CSF of the subject. The detectable amount of the FUS RNA may be reduced by at least 10%, at least 20%, at least 30%, at least 40%, at least 50%, at least 60%, at least 70%, at least 80%, or at least 90%. In certain embodiments, an oligomeric compound complementary to SEQ ID NO: 1 or SEQ ID NO: 2 is capable of reducing a detectable amount of a FUS protein in the CSF of the subject when the oligomeric compound is administered to the CSF of the subject. The detectable amount of the FUS protein may be reduced by at least 10%, at least 20%, at least 30%, at least 40%, at least 50%, at least 60%, at least 70%, at least 80%, or at least 90%.

VI. Certain Compounds

Compound No. 1043680

In certain embodiments, Compound No. 1043680 is characterized as a 5-10-5 MOE gapmer, having a sequence of (from 5' to 3') GTTTATCTGAATTCGCCATA (incorporated herein as SEQ ID NO: 12), wherein each of nucleosides 1-5 and 16-20 are 2'-O-methoxyethyl nucleosides, and each of nucleosides 6-15 are β-D-deoxyribonucleosides, wherein the internucleoside linkages between nucleosides 2 to 3, 3 to 4, 4 to 5, 5 to 6, 16 to 17, and 17 to 18 are phosphodiester linkages and the internucleoside linkages between nucleosides 1 to 2, 6 to 7, 7 to 8, 8 to 9, 9 to 10, 10 to 11, 11 to 12, 12 to 13, 13 to 14, 14 to 15, and 15 to 16 are phosphorothioate linkages, and wherein each cytosine is a 5'-methylcytosine.

In certain embodiments, Compound No. 1043680 is described by the following chemical notation: Ges Teo Teo Teo Aeo Tds mCds Tds Gds Ads Ads Tds Tds mCds Gds mCeo mCeo Aes Tes Ae (SEQ ID NO: 12); wherein, A=an adenine, mC=a 5'-methylcytosine, G=a guanine, T=a thymine, e=a 2'-O-methoxyethylribose modified sugar, d=a 2'-deoxyribose sugar, s=a phosphorothioate internucleoside linkage, and o=a phosphodiester internucleoside linkage.

In certain embodiments, Compound No. 1043680 is described by the following chemical structure, or a salt thereof:

(SEQ ID NO: 12)
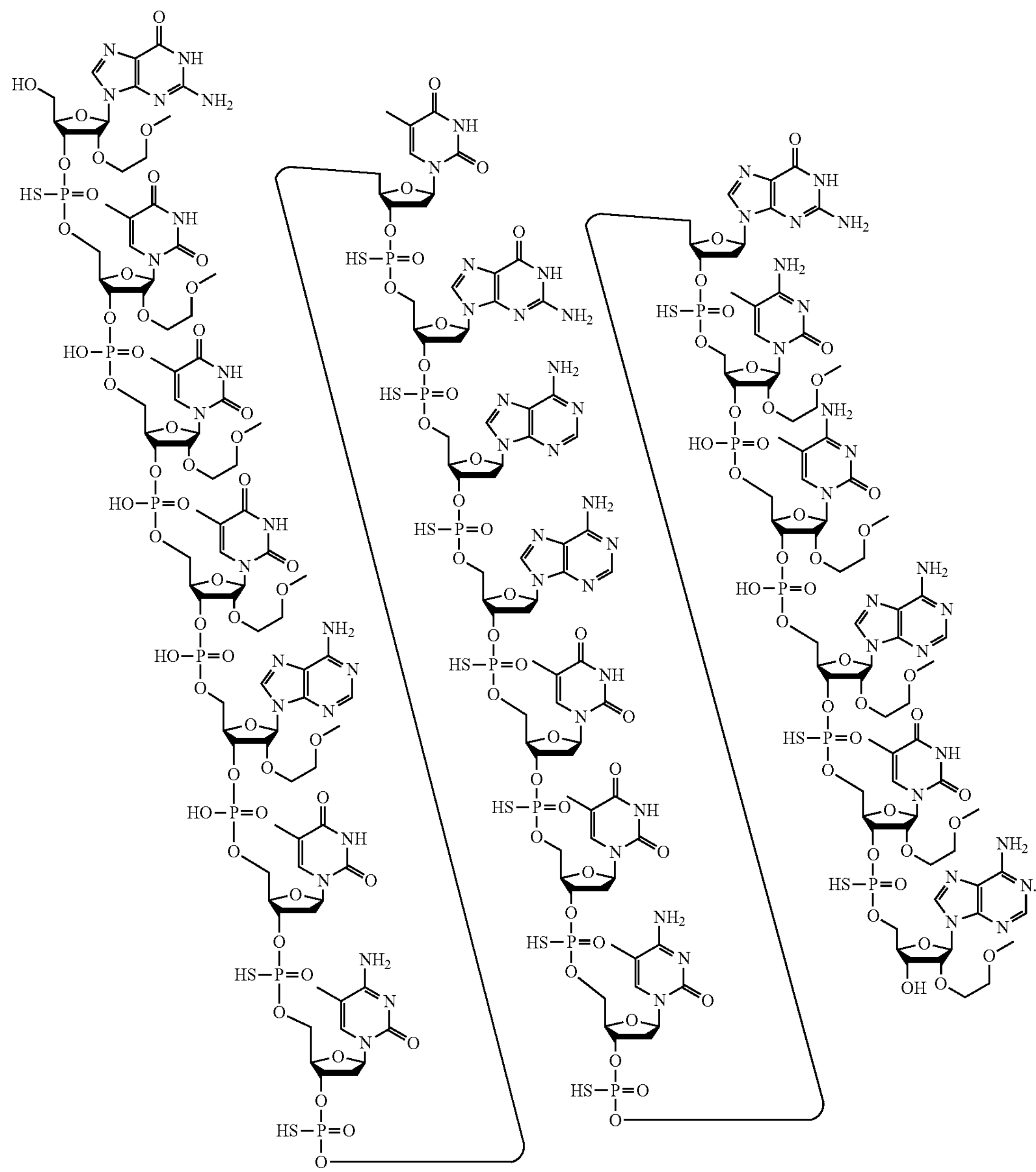
In certain embodiments, the sodium salt of Compound No. 1043680 is described by the following chemical structure:

(SEQ ID NO: 12)

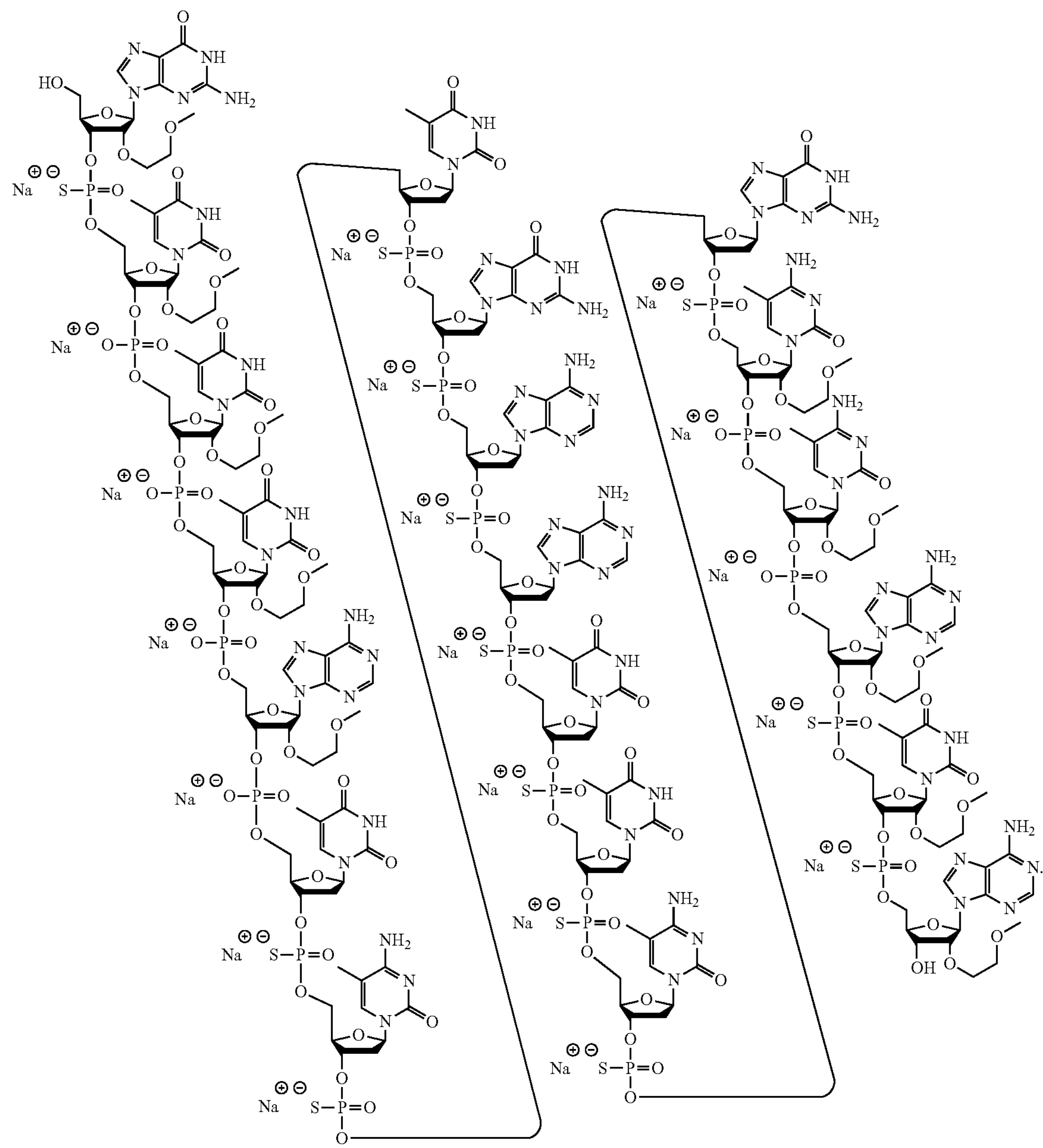

Compound No. 1044030

In certain embodiments, Compound No. 1044030 is characterized as a 5-10-5 MOE gapmer, having a sequence of (from 5' to 3') GCAATGTCACCTTTCATACC (incorporated herein as SEQ ID NO: 13), wherein each of nucleosides 1-5 and 16-20 are 2'-O-methoxyethyl nucleosides, and each of nucleosides 6-15 are β-D-deoxyribonucleosides, wherein the internucleoside linkages between nucleosides 2 to 3, 3 to 4, 4 to 5, 5 to 6, 16 to 17, and 17 to 18 are phosphodiester linkages and the internucleoside linkages between nucleosides 1 to 2, 6 to 7, 7 to 8, 8 to 9, 9 to 10, 10 to 11, 11 to 12, 12 to 13, 13 to 14, 14 to 15, and 15 to 16 are phosphorothioate linkages, and wherein each cytosine is a 5'-methylcyto sine.

In certain embodiments, Compound No. 1044030 is described by the following chemical notation: Ges Ceo Aeo Aeo Teo Gds Tds mCds Adsd mCds mCds Tds Tds Tds mCds Aeo Teo Aes mCes mCe (SEQ ID NO: 13); wherein, A=an adenine, mC=a 5'-methylcytosine, G=a guanine, T=a thymine, e=a 2'-O-methoxyethylribose modified sugar, d=a 2'-deoxyribose sugar, s=a phosphorothioate internucleoside linkage, and o=a phosphodiester internucleoside linkage.

In certain embodiments, Compound No. 1044030 is described by the following chemical structure, or a salt thereof:

(SEQ ID NO: 13)
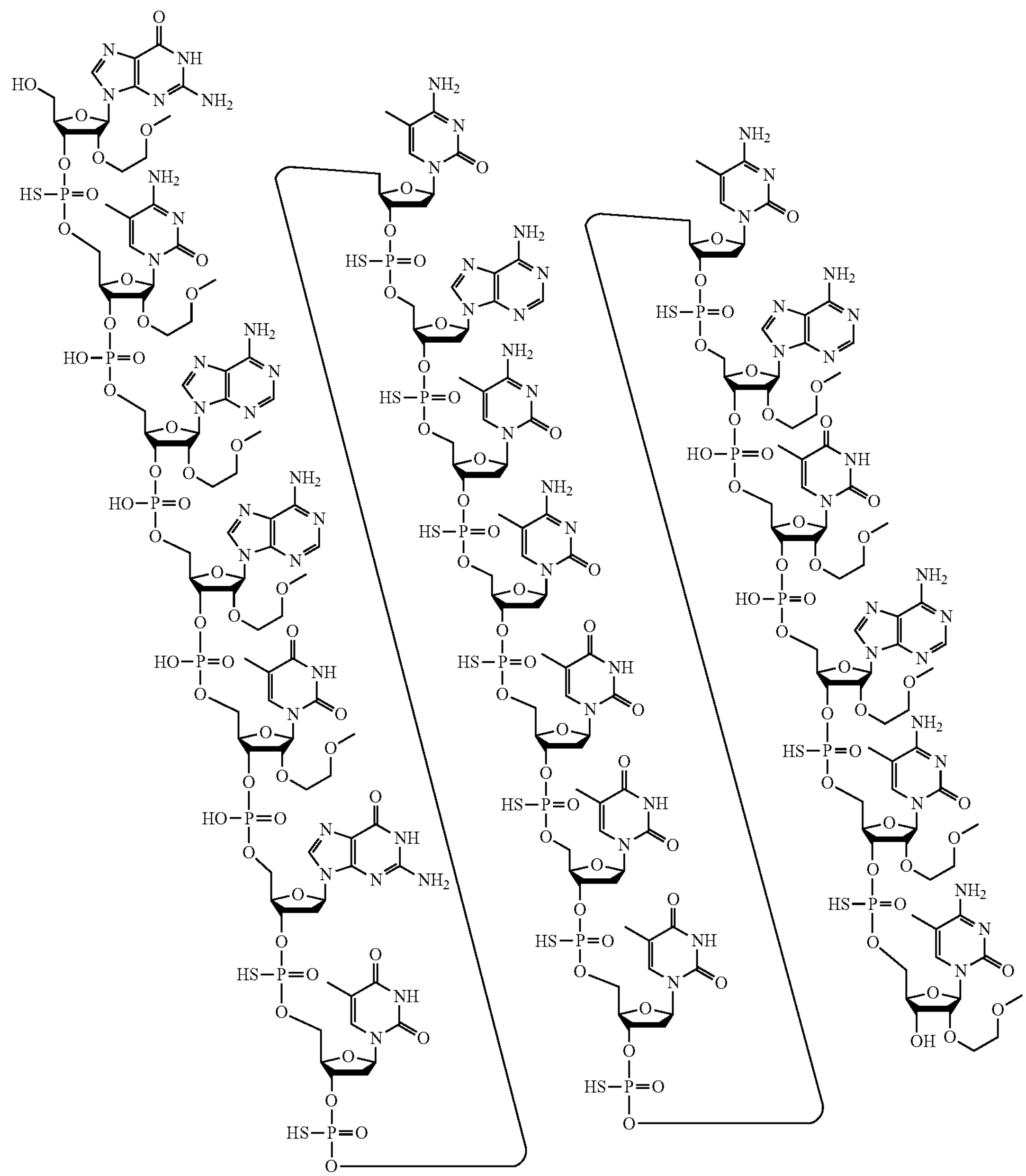
In certain embodiments, the sodium salt of Compound No. 1044030 is described by the following chemical structure:

(SEQ ID NO: 13)

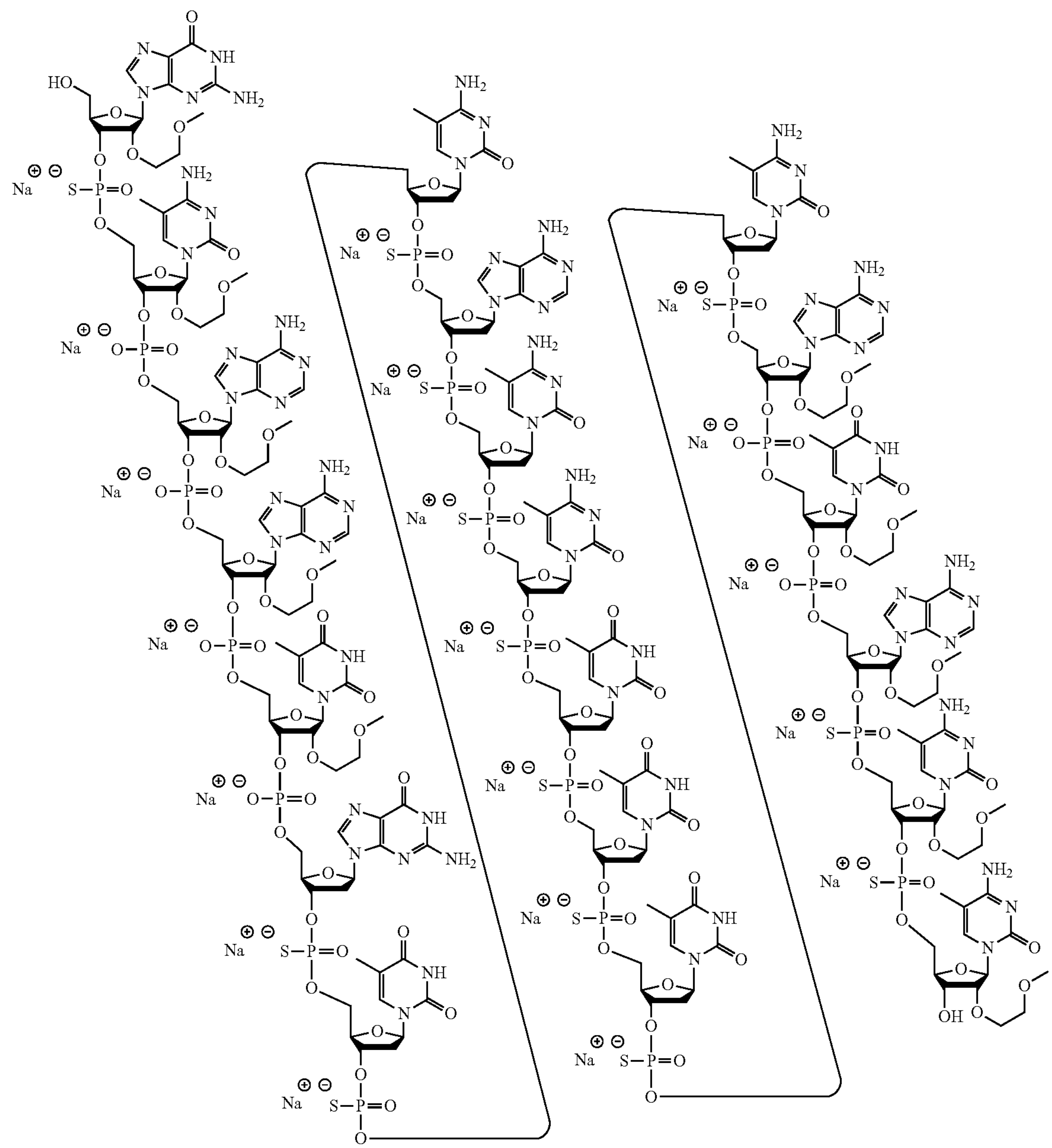

VII. Certain Hotspot Regions

In certain embodiments, nucleobases 1,786-1,841 of SEQ ID NO: 1 comprise a hotspot region. In certain embodiments, modified oligonucleotides are complementary to a portion of nucleobases 1,786-1,841 of SEQ ID NO: 1. In certain embodiments, modified oligonucleotides are 20 nucleobases in length. In certain embodiments, modified oligonucleotides are gapmers. In certain embodiments, the gapmers are MOE gapmers. In certain embodiments, the internucleoside linkages of the modified oligonucleotides are phosphorothioate internucleoside linkages and phosphodiester internucleoside linkages.

The nucleobase sequences of SEQ ID NOs: 34, 35, 111, 112, 188, 265, 342, and 418 are complementary to nucleobases 1,786-1,841 of SEQ ID NO: 1.

The nucleobase sequences of Compound Nos: 1043394, 1043395, 1043396, 1043397, 1043398, 1043399, 1043400, and 1043401 are complementary to nucleobases 1,786-1,841 of SEQ ID NO: 1.

In certain embodiments, modified oligonucleotides complementary to nucleobases 1,786-1,841 of SEQ ID NO: 1 achieve an average of 83% reduction of FUS mRNA in vitro in the standard cell assay. In certain embodiments, modified oligonucleotides complementary to nucleobases 1,786-1,841 of SEQ ID NO: 1 achieve a minimum of 62% reduction of FUS mRNA in vitro in the standard cell assay.

VIII. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to a subject, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, the compounds described herein act as an acids. For example, although Compound No. 1044030 may be drawn or described in protonated (free acid) form, or ionized and in association with a cation (salt)

form, aqueous solutions of Compound No. 1044030 exist in equilibrium among such forms. For example, a phosphate linkage of Compound No. 1044030 in aqueous solution exists in equilibrium among free acid, anion, and salt forms. Unless otherwise indicated, the term, "Compound No. 1044030," is intended to include all such forms. Moreover, Compound No. 1044030 has several such linkages, each of which is in equilibrium. Thus, Compound No. 1044030 exists in solution in an ensemble of forms at multiple positions all at equilibrium. The term "Compound No. 1044030" is intended to include all such forms. Drawn structures necessarily depict a single form. Nevertheless, unless otherwise indicated, such drawings are likewise intended to include corresponding forms. Herein, a structure depicting the free acid of Compound No. 1044030 followed by the term "or a salt thereof" expressly includes all such forms that may be fully or partially protonated/de-protonated/in association with a cation. In certain instances, one or more specific cation is identified.

In certain embodiments, compounds are in aqueous solution with sodium. In certain embodiments, compounds are in aqueous solution with potassium. In certain embodiments, compounds are in PBS. In certain embodiments, compounds are in water. In certain such embodiments, the pH of the solution is adjusted with NaOH and/or HCl to achieve a desired pH.

Herein, certain specific doses are described. For clarity and by way of example, a dose of Compound No. 1044030 in milligrams indicates the mass of the free acid form of Compound No. 1044030. As described above, in aqueous solution, the free acid is in equilibrium with anionic and salt forms. However, for the purpose of calculating dose, it is assumed that Compound No. 1044030 exists as a solvent-free, sodium-acetate free, anhydrous, free acid. For example, where Compound No. 1044030 is in solution comprising sodium (e.g., saline), Compound No. 1044030 may be partially or fully de-protonated and in association with Na+ ions. However, the mass of the protons is nevertheless counted toward the weight of the dose, and the mass of the Na+ ions are not counted toward the weight of the dose. Thus, for example, a dose of 100 mg of Compound No. 1044030 equals the number of fully protonated molecules that weighs 100 mg. This would be equivalent to 106 mg of solvent-free, sodium-acetate free, anhydrous sodiated Compound No. 1044030.

IX. Certain Dosage Amounts

In certain embodiments, described herein are methods of administering to a subject a therapeutically effective amount of a compound disclosed herein. In certain embodiments, the therapeutically effective amount is 50 mg. In certain embodiments, the therapeutically effective amount is about 50 mg. In certain embodiments, the therapeutically effective amount is 60 mg. In certain embodiments, the therapeutically effective amount is about 60 mg. In certain embodiments, the therapeutically effective amount is 70 mg. In certain embodiments, the therapeutically effective amount is about 70 mg. In certain embodiments, the therapeutically effective amount is 80 mg. In certain embodiments, the therapeutically effective amount is about 80 mg. In certain embodiments, the therapeutically effective amount is 90 mg. In certain embodiments, the therapeutically effective amount is about 90 mg. In certain embodiments, the therapeutically effective amount is 100 mg. In certain embodiments, the therapeutically effective amount is about 100 mg. In certain embodiments, the therapeutically effective amount is 110 mg. In certain embodiments, the therapeutically effective amount is about 110 mg. In certain embodiments, the therapeutically effective amount is 120 mg. In certain embodiments, the therapeutically effective amount is about 120 mg. In certain embodiments, the therapeutically effective amount is 130 mg. In certain embodiments, the therapeutically effective amount is about 130 mg. In certain embodiments, the therapeutically effective amount is 140 mg. In certain embodiments, the therapeutically effective amount is about 140 mg. In certain embodiments, the therapeutically effective amount is 150 mg. In certain embodiments, the therapeutically effective amount is about 150 mg. In certain embodiments, the therapeutically effective amount is 160 mg. In certain embodiments, the therapeutically effective amount is about 160 mg. In certain embodiments, the therapeutically effective amount is 170 mg. In certain embodiments, the therapeutically effective amount is about 170 mg. In certain embodiments, the therapeutically effective amount is 180 mg. In certain embodiments, the therapeutically effective amount is about 180 mg. In certain embodiments, the therapeutically effective amount is 190 mg. In certain embodiments, the therapeutically effective amount is about 190 mg. In certain embodiments, the therapeutically effective amount is 200 mg. In certain embodiments, the therapeutically effective amount is about 200 mg.

In certain embodiments, the therapeutically effective amount is any of 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, and 300 mg.

In certain embodiments, the therapeutically effective amount is any of about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, and about 300 mg.

In certain embodiments, the therapeutically effective amount is any of 95.0 mg, 95.1 mg, 95.2 mg, 95.3 mg, 95.4 mg, 95.5 mg, 95.6 mg, 95.7 mg, 95.8 mg, 95.9 mg, 96.0 mg, 96.1 mg, 96.2 mg, 96.3 mg, 96.4 mg, 96.5 mg, 96.6 mg, 96.7 mg, 96.8 mg, 96.9 mg, 97.0 mg, 97.1 mg, 97.2 mg, 97.3 mg, 97.4 mg, 97.5 mg, 97.6 mg, 97.7 mg, 97.8 mg, 97.9 mg, 98.0 mg, 98.1 mg, 98.2 mg, 98.3 mg. 98.4 mg, 98.5 mg, 98.6 mg, 98.7 mg, 98.8 mg, 98.9 mg, 99.0 mg, 99.1 mg, 99.2 mg, 99.3 mg, 99.4 mg, 99.5 mg, 99.6 mg, 99.7 mg, 99.8 mg, 99.9 mg, 100.0 mg, 100.1 mg, 100.2 mg, 100.3 mg. 100.4 mg, 100.5 mg, 100.6 mg, 100.7 mg, 100.8 mg, 100.9 mg, 101.0 mg, 101.1 mg, 101.2 mg, 101.3 mg, 101.4 mg, 101.5 mg, 101.6 mg, 101.7 mg, 101.8 mg, 101.9 mg, 102.0 mg, 102.1 mg, 102.2 mg, 102.3 mg. 102.4 mg, 102.5 mg, 102.6 mg, 102.7 mg, 102.8 mg, 102.9 mg, 103.0 mg, 103.1 mg, 103.2 mg, 103.3 mg, 103.4 mg, 103.5 mg, 103.6 mg, 103.7 mg, 103.8 mg, 103.9 mg, 104.0 mg, 104.1 mg, 104.2 mg, 104.3 mg. 104.4 mg, 104.5 mg, 104.6 mg, 104.7 mg, 104.8 mg, 104.9 mg, and 105.0 mg.

In certain embodiments, the therapeutically effective amount is any of about 95.0 mg, about 95.1 mg, about 95.2 mg, about 95.3 mg, about 95.4 mg, about 95.5 mg, about 95.6 mg, about 95.7 mg, about 95.8 mg, about 95.9 mg, about 96.0 mg, about 96.1 mg, about 96.2 mg, about 96.3 mg, about 96.4 mg, about 96.5 mg, about 96.6 mg, about 96.7 mg, about 96.8 mg, about 96.9 mg, about 97.0 mg, about 97.1 mg, about 97.2 mg, about 97.3 mg, about 97.4 mg, about 97.5 mg, about 97.6 mg, about 97.7 mg, about 97.8 mg, about 97.9 mg, about 98.0 mg, about 98.1 mg, about 98.2 mg, about 98.3 mg. 98.4 mg, about 98.5 mg, about 98.6 mg, about 98.7 mg, about 98.8 mg, about 98.9 mg, about 99.0 mg, about 99.1 mg, about 99.2 mg, about 99.3 mg, about 99.4 mg, about 99.5 mg, about 99.6 mg, about 99.7 mg, about 99.8 mg, about 99.9 mg, about 100.0 mg, about 100.1 mg, about 100.2 mg, about 100.3 mg. 100.4 mg, about 100.5 mg, about 100.6 mg, about 100.7 mg, about 100.8 mg, about 100.9 mg, about 101.0 mg, about 101.1 mg, about 101.2 mg, about 101.3 mg, about 101.4 mg, about 101.5 mg, about 101.6 mg, about 101.7 mg, about 101.8 mg, about 101.9 mg, about 102.0 mg, about 102.1 mg, about 102.2 mg, about 102.3 mg. 102.4 mg, about 102.5 mg, about 102.6 mg, about 102.7 mg, about 102.8 mg, about 102.9 mg, about 103.0 mg, about 103.1 mg, about 103.2 mg, about 103.3 mg, about 103.4 mg, about 103.5 mg, about 103.6 mg, about 103.7 mg, about 103.8 mg, about 103.9 mg, about 104.0 mg, about 104.1 mg, about 104.2 mg, about 104.3 mg. 104.4 mg, about 104.5 mg, about 104.6 mg, about 104.7 mg, about 104.8 mg, about 104.9 mg, and about 105.0 mg.

In certain embodiments, the therapeutically effective amount is any of 115.0 mg, 115.1 mg, 115.2 mg, 115.3 mg, 115.4 mg, 115.5 mg, 115.6 mg, 115.7 mg, 115.8 mg, 115.9 mg, 116.0 mg, 116.1 mg, 116.2 mg, 116.3 mg, 116.4 mg, 116.5 mg, 116.6 mg, 116.7 mg, 116.8 mg, 116.9 mg, 117.0 mg, 117.1 mg, 117.2 mg, 117.3 mg, 117.4 mg, 117.5 mg, 117.6 mg, 117.7 mg, 117.8 mg, 117.9 mg, 118.0 mg, 118.1 mg, 118.2 mg, 118.3 mg. 118.4 mg, 118.5 mg, 118.6 mg, 118.7 mg, 118.8 mg, 118.9 mg, 119.0 mg, 119.1 mg, 119.2 mg, 119.3 mg, 119.4 mg, 119.5 mg, 119.6 mg, 119.7 mg, 119.8 mg, 119.9 mg, 120.0 mg, 120.1 mg, 120.2 mg, 120.3 mg. 120.4 mg, 120.5 mg, 120.6 mg, 120.7 mg, 120.8 mg, 120.9 mg, 121.0 mg, 121.1 mg, 121.2 mg, 121.3 mg, 121.4 mg, 121.5 mg, 121.6 mg, 121.7 mg, 121.8 mg, 121.9 mg, 122.0 mg, 122.1 mg, 122.2 mg, 122.3 mg. 122.4 mg, 122.5 mg, 122.6 mg, 122.7 mg, 122.8 mg, 122.9 mg, 123.0 mg, 123.1 mg, 123.2 mg, 123.3 mg, 123.4 mg, 123.5 mg, 123.6 mg, 123.7 mg, 123.8 mg, 123.9 mg, 124.0 mg, 124.1 mg, 124.2 mg, 124.3 mg. 124.4 mg, 124.5 mg, 124.6 mg, 124.7 mg, 124.8 mg, 124.9 mg, and 125.0 mg.

In certain embodiments, the therapeutically effective amount is any of about 115.0 mg, about 115.1 mg, about 115.2 mg, about 115.3 mg, about 115.4 mg, about 115.5 mg, about 115.6 mg, about 115.7 mg, about 115.8 mg, about 115.9 mg, about 116.0 mg, about 116.1 mg, about 116.2 mg, about 116.3 mg, about 116.4 mg, about 116.5 mg, about 116.6 mg, about 116.7 mg, about 116.8 mg, about 116.9 mg, about 117.0 mg, about 117.1 mg, about 117.2 mg, about 117.3 mg, about 117.4 mg, about 117.5 mg, about 117.6 mg, about 117.7 mg, about 117.8 mg, about 117.9 mg, about 118.0 mg, about 118.1 mg, about 118.2 mg, about 118.3 mg. 118.4 mg, about 118.5 mg, about 118.6 mg, about 118.7 mg, about 118.8 mg, about 118.9 mg, about 119.0 mg, about 119.1 mg, about 119.2 mg, about 119.3 mg, about 119.4 mg, about 119.5 mg, about 119.6 mg, about 119.7 mg, about 119.8 mg, about 119.9 mg, about 120.0 mg, about 120.1 mg, about 120.2 mg, about 120.3 mg. 120.4 mg, about 120.5 mg, about 120.6 mg, about 120.7 mg, about 120.8 mg, about 120.9 mg, about 121.0 mg, about 121.1 mg, about 121.2 mg, about 121.3 mg, about 121.4 mg, about 121.5 mg, about 121.6 mg, about 121.7 mg, about 121.8 mg, about 121.9 mg, about 122.0 mg, about 122.1 mg, about 122.2 mg, about 122.3 mg. 122.4 mg, about 122.5 mg, about 122.6 mg, about 122.7 mg, about 122.8 mg, about 122.9 mg, about 123.0 mg, about 123.1 mg, about 123.2 mg, about 123.3 mg, about 123.4 mg, about 123.5 mg, about 123.6 mg, about 123.7 mg, about 123.8 mg, about 123.9 mg, about 124.0 mg, about 124.1 mg, about 124.2 mg, about 124.3 mg. 124.4 mg, about 124.5 mg, about 124.6 mg, about 124.7 mg, about 124.8 mg, about 124.9 mg, and about 125.0 mg.

In certain embodiments, the therapeutically effective amount is any of 40 mg to 200 mg, 40 mg to 190 mg, 40 mg to 180 mg, 40 mg to 170 mg, from 40 mg to 160 mg, 40 mg to 150 mg, 40 mg to 140 mg, 40 mg to 120 mg, 40 mg to 110 mg, 40 mg to 100 mg, 40 mg to 80 mg, 40 mg to 70 mg, 40 mg to 60 mg, 40 mg to 50 mg, 50 mg to 200 mg, 50 mg to 190 mg, 50 mg to 180 mg, 50 mg to 170 mg, 50 mg to 160 mg, 50 mg to 150 mg, 50 mg to 140 mg, 50 mg to 120 mg, 50 mg to 110 mg, 50 mg to 100 mg, 50 mg to 80 mg, 50 mg to 70 mg, 50 mg to 60 mg, 60 mg to 200 mg, 60 mg to 190 mg, 60 mg to 180 mg, 60 mg to 170 mg, 60 mg to 160 mg, 60 mg to 150 mg, 60 mg to 140 mg, 60 mg to 120 mg, 60 mg to 110 mg, 60 mg to 100 mg, 60 mg to 80 mg, 60 mg to 70 mg, 70 mg to 200 mg, 70 mg to 190 mg, 70 mg to 180 mg, 70 mg to 170 mg, 70 mg to 160 mg, 70 mg to 150 mg, 70 mg to 140 mg, 70 mg to 120 mg, 70 mg to 110 mg, 70 mg to 100 mg, 70 mg to 80 mg, 80 mg to 200 mg, 80 mg to 190 mg, 80 mg to 180 mg, 80 mg to 170 mg, 80 mg to 160 mg, 80 mg to 150 mg, 80 mg to 140 mg, 80 mg to 120 mg, 80 mg to 110 mg, 80 mg to 100 mg, 80 mg to 90 mg, 90 mg to 200 mg, 90 mg to 190 mg, 90 mg to 180 mg, 90 mg to 170 mg, 90 mg to 160 mg, 90 mg to 150 mg, 90 mg to 140 mg, 90 mg to 120 mg, 90 mg to 110 mg, 90 mg to 100 mg, 100 mg to 200 mg, 100 mg to 190 mg, 100 mg to 180 mg, 100 mg to 170 mg, 100 mg to 160 mg, 100 mg to 150 mg, 100 mg to 140 mg, 100 mg to 120 mg, 100 mg to 110 mg, 110 mg to 200 mg, 110 mg to 190 mg, 110 mg to 180 mg, 110 mg to 170 mg, 110 mg to 160 mg, 110 mg to 150 mg, 110 mg to 140 mg, 110 mg to 130 mg, 110 mg to 120 mg, 120 mg to 200 mg, 120 mg to 190 mg, 120 mg to 180 mg, 120 mg to 170 mg, 120 mg to 160 mg, 120 mg to 150 mg, 120 mg to 140 mg, 120 mg to 130 mg, 130 mg to 200 mg, 130 mg to 190 mg, 130 mg to 180 mg, 130 mg to 170 mg, 130 mg to 160 mg, 130 mg to 150 mg, 130 mg to 140 mg, 140 mg to 200 mg, 140 mg to 190 mg, 140 mg to 180 mg, 140 mg to 170 mg, 140 mg to 160 mg, 140 mg to 150 mg, 150 mg to 200 mg, 150 mg to 190 mg, 150 mg to 180 mg, 150 mg to 170 mg, 150 mg to 160 mg, 160 mg to 200 mg, 160 mg to 190 mg, 160 mg to 180 mg, 160 mg to 170 mg, 180 mg to 200 mg, 180 mg to 190 mg, 190 mg to 200 mg, 105 mg to 135 mg, 105 mg to 130 mg, 105 mg to 125 mg 105 mg to 120 mg, 110 mg to 135 mg, 110 mg to 130 mg, 110 mg to 125 mg, 110 mg to 120 mg, 115 mg to 135 mg, 115 mg to 130 mg, 115 mg to 125 mg, 115 mg to 120 mg, 115 mg to 125 mg, 115 mg to 120 mg, 120 mg to 135 mg, 120 mg to 125 mg, 125 mg to 140 mg, 125 mg to 130 mg, 130 mg to 135 mg, 135 mg to 140 mg, 120 mg to 129 mg, 120 mg to 128 mg, 120 mg to 127 mg, 120 mg to 86 mg, 120 mg to 124 mg, 120 mg to 123 mg, 120 mg to 122 mg, 120 mg to 121 mg, 121 mg to 130 mg, 122 mg to 129 mg, 122 mg to 128 mg, 122 mg to 127 mg, 122 mg to 126 mg, 122 mg to 125 mg, 122 mg to 124 mg, 122 mg to 123 mg, 123 mg to 130 mg, 123 mg to 129 mg, 123 mg to 128 mg, 123 mg to 127 mg, 123 mg to 126 mg, 123 mg to 125 mg, 123 mg to 124 mg, 124 mg to 130 mg, 124 mg to 129 mg, 124 mg to 128 mg, 124 mg to 127 mg, 124 mg to 126 mg, 124 mg to 125 mg, 125 mg to 129 mg, 125 mg to 128 mg, 125 mg to 127 mg, 125 mg to 126 mg, 126 mg to 130 mg, 126 mg to 129 mg, 126 mg to 128 mg, 126 mg to 127 mg, 127 mg to 130 mg, 127 mg to 129 mg, 127 mg to 128 mg, 128 mg to 130 mg, 128 mg to 129 mg, and 129 mg to 130 mg.

In certain embodiments, the therapeutically effective amount is any of less than 300 mg, less than 295 mg, less than 290 mg, less than 285 mg, less than 280 mg, less than 275 mg, less than 270 mg, less than 265 mg, less than 260 mg, less than 255 mg, less than 250 mg, less than 245 mg, less than 240 mg, less than 235 mg, less than 230 mg, less than 225 mg, less than 220 mg, less than 215 mg, less than 210 mg, less than 205 mg, less than 200 mg, less than 195 mg, less than 190 mg, less than 185 mg, less than 180 mg, less than 175 mg, less than 170 mg, less than 165 mg, less than 160 mg, less than 150 mg, less than 145 mg, less than 140 mg, less than 135 mg, less than 130 mg, less than 125 mg, less than 120 mg, less than 115 mg, less than 110 mg, less than 105 mg, less than 100 mg, less than 95 mg, less than 90 mg, less than 85 mg, less than 80 mg, less than 75 mg, less than 70 mg, less than 65 mg, less than 60 mg, less than 55 mg, less than 50 mg, less than 45 mg, less than 40 mg, less than 35 mg, less than 30 mg, less than 25 mg, less than 20 mg, less than 15 mg, less than 10 mg, and less than 5 mg.

In certain embodiments, the therapeutically effective amount is any of less than about 300 mg, less than about 295 mg, less than about 290 mg, less than about 285 mg, less than about 280 mg, less than about 275 mg, less than about 270 mg, less than about 265 mg, less than about 260 mg, less than about 255 mg, less than about 250 mg, less than about 245 mg, less than about 240 mg, less than about 235 mg, less than about 230 mg, less than about 225 mg, less than about 220 mg, less than about 215 mg, less than about 210 mg, less than about 205 mg, less than about 200 mg, less than about 195 mg, less than about 190 mg, less than about 185 mg, less than about 180 mg, less than about 175 mg, less than about 170 mg, less than about 165 mg, less than about 160 mg, less than about 150 mg, less than about 145 mg, less than about 140 mg, less than about 135 mg, less than about 130 mg, less than about 125 mg, less than about 120 mg, less than about 115 mg, less than about 110 mg, less than about 105 mg, less than about 100 mg, less than about 95 mg, less than about 90 mg, less than about 85 mg, less than about 80 mg, less than about 75 mg, less than about 70 mg, less than about 65 mg, less than about 60 mg, less than about 55 mg, less than about 50 mg, less than about 45 mg, less than about 40 mg, less than about 35 mg, less than about 30 mg, less than about 25 mg, less than about 20 mg, less than about 15 mg, less than about 10 mg, and less than about 5 mg.

In certain embodiments, the therapeutically effective amount is any of at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185, at least 190 mg, at least 195 mg, and at least 200 mg.

In certain embodiments, the therapeutically effective amount is any of at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 115 mg, at least about 120 mg, at least about 125 mg, at least about 130 mg, at least about 135 mg, at least about 140 mg, at least about 145 mg, or at least about 150 mg, at least about 155 mg, at least about 160 mg, at least about 165 mg, at least about 170 mg, at least about 175 mg, at least about 180 mg, at least about 185, at least about 190 mg, at least about 195 mg, and at least about 200 mg.

X. Certain Dosing Regimens

In certain embodiments, described herein are methods of administering to a subject a therapeutically effective amount of a compound disclosed herein one or more times. In certain embodiments, methods comprise administering the therapeutically effective amount at least 1, 2, 3, 4, 5, 6, 7, 8, 9 or 10 times. In certain embodiments, methods comprise administering the therapeutically effective amount once every 4 weeks. In certain embodiments, methods comprise administering the therapeutically effective amount once every 8 weeks. In certain embodiments, methods comprise administering the therapeutically effective amount once every 12 weeks. In certain embodiments, methods comprise administering the therapeutically effective amount once every 16 weeks.

In certain embodiments, methods comprise administering the therapeutically effective amount about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, or about every 20 weeks.

In certain embodiments, methods comprise administering the therapeutically effective amount for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least about 12 months.

Loading and Maintenance Doses

In certain embodiment, the therapeutically effective amount is administered as a loading dose and/or a maintenance dose. In certain embodiments, methods comprise administering a loading dose or doses and subsequently administering a maintenance dose or doses. In certain embodiments, methods comprise administering a loading dose once about every 4 weeks, and subsequently administering a maintenance dose once about every 8 weeks. In certain embodiments, methods comprise administering a loading dose once about every 4 weeks, and subsequently administering a maintenance dose once about every 16 weeks.

In certain embodiments, methods comprise administering at least 2 loading doses, at least 3 loading doses, at least 4 loading doses, at least 5 loading doses, or at least 6 loading doses. In certain embodiments, methods comprise administering 2, 3, 4, 5, 6, 7, 8, 9, 10, 11, 12, 13, 14, 15, or 16 loading doses. In certain embodiments, methods comprise administering a loading dose or doses about every 1 week, about every 2 weeks, about every 3 weeks, about every 4 weeks, about every 5 weeks, about every 6 weeks, about every 7 weeks, about every 8 weeks, about every 9 weeks, about every 10 weeks, about every 11 weeks, or about every 12 weeks. In certain embodiments, methods comprise administering an initial loading dose and administering a second loading dose about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks after administering the initial loading dose.

In certain embodiments, methods comprise administering at least 2 maintenance doses, at least 3 maintenance doses, at least 4 maintenance doses, at least 5 maintenance doses, or at least 6 maintenance doses. In certain embodiments, methods comprise administering 2, 3, 4, 5, 6, 7, 8, 9, 10, 11, 12, 13, 14, 15, or 16 maintenance doses. In some instances, methods comprise administering a maintenance dose or doses about every 4 weeks, about every 5 weeks, about every 6 weeks, about every 7 weeks, about every 8 weeks, about every 9 weeks, about every 10 weeks, about every 11 weeks, about every 12 weeks, about every 13 weeks, about every 14 weeks, about every 15 weeks, about every 16 weeks, about every 17 weeks, about every 18 weeks, about every 19 weeks, or about every 20 weeks. In certain embodiments, methods comprise administering a first maintenance dose and administering a second maintenance dose about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, or about 20 weeks after administering the first maintenance dose.

In certain embodiments, methods comprise administering a first maintenance dose or doses about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, or about 20 weeks after administering the last loading dose.

XI. Potency and Efficacy

In certain embodiments, described herein are methods of reducing FUS RNA and/or FUS protein in a cell or biological fluid of a human subject, wherein the methods comprise administering a therapeutically effective amount of Compound No. 1044030 to the subject. In certain embodiments, methods reduce FUS RNA and/or FUS protein in the cerebrospinal fluid of the human subject. One may determine whether or not methods reduce FUS RNA and/or FUS protein, e.g., by detecting/quantifying a first amount of FUS RNA or FUS protein in a first biological sample obtained before administering and detecting/quantifying a second amount of FUS RNA or FUS protein in a second biological sample obtained after administering, and detecting or quantifying a reduction in FUS RNA or FUS protein by comparing the first amount to the second amount.

In certain embodiments, methods comprise reducing FUS RNA and/or FUS protein by 1-100%, or a range defined by any two of these values. In certain embodiments, methods comprise reducing FUS RNA and/or FUS protein by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In certain embodiments, methods comprise reducing FUS RNA or FUS protein by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%.

In certain embodiments, methods comprise reducing FUS RNA or FUS protein by about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to 100%.

In certain embodiments, methods comprise administering Compound No. 1044030 to a subject and detecting or quantifying an amount of FUS RNA or FUS protein in a cell or a biological fluid of the subject. In certain embodiments, methods comprise detecting/quantifying a first amount of FUS RNA or FUS protein in a first biological sample obtained before administering and detecting/quantifying a second amount of FUS RNA or FUS protein in a second biological sample obtained after administering, and detecting or quantifying a reduction in FUS RNA or FUS protein by comparing the first amount to the second amount. In certain embodiments, the second biological sample is obtained less than about 24 hours after administering. In certain embodiments, the second biological sample is obtained less than about 1 week after administering. In certain embodiments, the second biological sample is obtained about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, or about 18 weeks after administering. In certain embodiments, methods comprise increasing or decreasing the dose after comparing the first amount to the second amount. In certain embodiments, methods comprise administering more frequently or less frequently after comparing the first amount to the second amount.

XII. Certain Indications

In certain embodiments, provided herein are methods of administering to a subject in need thereof an oligomeric compound targeting a FUS nucleic acid. Such oligomeric compounds are described herein.

In certain embodiments, the subject has a neurodegenerative condition. In certain embodiments, the neurodegenerative condition is a polyglutamine (polyQ) repeat disorder. In certain embodiments, the neurodegenerative condition is a neuronal intranuclear inclusion body disease (NIIBD). In certain embodiments, the neurodegenerative condition is ALS. In certain embodiments, the neurodegenerative condition is FTLD. In certain embodiments, the subject has juvenile ALS, wherein the subject develops at least one symptom or hallmark of ALS before the age of 25.

In certain embodiments, the subject has a FUS mutation (a mutation in a gene encoding FUS). In certain embodiments, the subject has a neurodegenerative condition associated with a FUS mutation. In certain embodiments, the subject has a FUS mutation associated with ALS. In certain embodiments, the FUS mutation associated with ALS results in overexpression of FUS relative to expression of FUS in a control subject that does not have a FUS mutation. In certain embodiments, the FUS mutation associated with ALS results in a gain of function of FUS protein relative to the activity of FUS protein in a control subject that does not have a FUS mutation. In certain embodiments the FUS mutation causes a FUS protein to aggregate in the cytoplasm, misfold, aggregate, or any combination thereof. In certain embodiments, the FUS mutation is a missense mutation. In certain embodiments, the FUS mutation is a truncation mutation.

In certain embodiments, the FUS mutation associated with ALS is a single nucleotide polymorphism (SNP). In certain embodiments, the SNP is selected from rs121909667 (C>G), rs121909668 (C>A/C>G/C>T), rs121909669 (G>A), rs121909671 (G>A/G>T), rs186547381 (C>T), rs267606831 (G>A), rs267606832 (C>G/C>T), rs267606833 (A>T), rs387906627 (C>T), rs387906628 (G>A), rs387907274 (C>T), rs752076094 (A>G), rs764487847 (C>G/C>T), rs886041389 (G>C), rs886041390 (C>T), rs886041577 (delGA), rs886041776 (dupGGTGG), rs1085308015 (A>C/A>G), rs1161032867 (delG/dupGGG), rs1555509569 (delA), rs1555509609 (A>C/A>G/A>T), rs1555509693 (A>G), rs1596908744 (delTT), rs1596912983 (dupAG), and rs121909668 (C>A/C>G/C>T), located at positions 31191408, 31191418, 31191410, 31191419, 31190398, 31191089, 31185061, 31191427, 31191052, 31185031, 31189158, 31185175, 31183884, 31191429, 31191431, 31191073-31191074, 31191079-31191083, 31191407, 31191070-31191073, 31190961, 31191109, 31191421, 31189748-31189751, 31191076-31191079, and 31191418 of chromosome 16, respectively, according to Genome Reference Consortium Human Build 38 patch release 12 (GRCh38.p12).

In certain embodiments, the FUS mutation associated with ALS results in a modification of a FUS protein amino acid sequence relative to a wildtype FUS protein (e.g., see NCBI reference number NP_004951.1 (SEQ ID NO: 3)). In certain embodiments, the modification of the FUS protein amino acid sequence is selected from S57del, S96del, G156E, G171-174del, G174-175del, G187S, G191S, G206S, R216C, G225V, G230C, R234C, R234L, R244C, M254V, S402_P411delinsGGGG, S462F, G466VfsX14, Y484AfsX514, R495X, R495EfsX527, G497AfsX527, G507D, K510WfsX517, K510E, S513P, R514S, R514G, G515C, E516V, H517D, H517P, H517Q, R518G, R518K, Q519IfsX9, R521C, R521G, R521H, R521L, R521S, R522G, R524S, R524T, R524W, and P525L. In certain embodiments, the FUS mutation results in a modification of at least one of the 60 amino acids at the C-terminal of the FUS protein amino acid sequence relative to a wildtype FUS protein. In certain embodiments, the FUS mutation results in a modification of at least one of the 17 amino acids at the C-terminal of the FUS protein amino acid sequence relative to a wildtype FUS protein. In certain embodiments, the FUS mutation results in the substitution of the proline at amino acid position 525 of SEQ ID NO: 3 with an amino acid other than proline. In certain embodiments, the FUS mutation is P525L.

In certain embodiments, methods comprise identifying a FUS mutation in a subject. In certain embodiments, methods comprise identifying a FUS mutation in a subject and subsequently administering an oligomeric compound disclosed herein to the subject. In certain embodiments, identifying the FUS mutation may comprise obtaining information about a sequence of a FUS nucleic acid in a sample from the subject. In certain embodiments, obtaining information about the sequence of the FUS nucleic acid comprises obtaining a sequence of a FUS nucleic acid in a sample from the subject. In certain embodiments, the sequence of the FUS nucleic acid is obtained from a sequencing reaction, e.g., Sanger sequencing or high throughput sequencing. In certain embodiments, identifying a FUS mutation comprises contacting the FUS nucleic acid with a primer or a probe. In certain embodiments, the primer or probe hybridizes to the nucleic acid if the mutation is present. In certain embodiments, the primer or probe does not hybridize to the nucleic acid if the mutation is present.

XIII. Certain Comparator Compounds

Comparator Compound No. 441522 was selected as a comparator compound in the experiment described in Example 8 of the instant specification. Comparator Compound No. 441522 is identical to a FUS-targeting modified oligonucleotide described by Lagier-Tourenne et al., Nat Neurosci. 15(11):1488-1497 (2012), incorporated herein by reference. Compound No. 441522 is a gapmer having a sugar motif of (from 5' to 3') eeeeeddddddddddeeeee, wherein each "e" represents a 2'-MOE sugar moiety and each "d" represents a 2'-β-D-deoxyribosyl sugar moiety; having a sequence of (from 5' to 3') CCTGGTTATTTCCCATGAGC (SEQ ID NO: 481) wherein each "C" of the gap is a 5-methyl cytosine; and wherein each internucleoside linkage is a phosphorothioate internucleoside linkage.

In certain embodiments, compounds described herein are more tolerable relative to Comparator Compound No. 441522.

For example, as described herein (see Example 5), Comparator Compound No. 441522 had a 3-hour FOB of 6.00 in mice, whereas Compound No. 1044030 had a 3-hour FOB of 0.00 in mice. An FOB of 6 indicates the mouse is immobile and unresponsive to stimuli. An FOB of 0 indicates a bright, alert, and responsive mouse. Therefore, certain compounds described herein are more tolerable than Comparator Compound No. 441522.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^{m}$CGAUCG," wherein $^{m}$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}H$ hydrogen atoms. Isotopic substitutions encompassed by the compounds herein include but are not limited to: $^{2}H$ or $^{3}H$ in place of $^{1}H$, $^{13}C$ or $^{14}C$ in place of $^{12}C$, $^{5}N$ in place of $^{14}N$, $^{17}O$ or $^{18}O$ in place of $^{16}O$, and $^{33}S$, $^{34}S$, $^{35}S$ or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1: Effects of Modified Oligonucleotides on Human FUS RNA In Vitro, Single Dose Modified oligonucleotides complementary to human FUS were designed and tested for their single dose effects on FUS mRNA in vitro.

The modified oligonucleotides are 5-10-5 MOE gapmers, wherein a central gap segment consists of ten 2'-β-D-deoxynucleosides, the 5' wing segment consists of five 2'-MOE nucleosides, and the 3' wing segment consists of five 2'-MOE nucleosides. The sugar motif of the gapmers is (from 5' to 3'): eeeeeddddddddddeeeee; wherein 'd' represents a 2'-β-D-deoxyribosyl sugar moiety, and 'e' represents a 2'-MOE sugar moiety. The gapmers have an internucleoside linkage motif of (from 5' to 3'): soooossssssssssooss; wherein "s" represents a phosphorothioate internucleoside linkage and "o" represents a phosphodiester internucleoside linkage. All cytosine residues are 5-methylcytosines.

The sequences of the modified oligonucleotides are shown in Tables 1-6 below. "Start site" indicates the 5'-most nucleoside to which the modified oligonucleotide is complementary in the human gene sequence. "Stop site" indicates the 3'-most nucleoside to which the modified oligonucleotide is complementary in the human gene sequence. Each modified oligonucleotide listed in the Tables 1-6 is 100% complementary to SEQ ID NO: 2 (GENBANK Accession No. NC_000016.10 truncated from nucleotides 31176001 to 31198000). 'N/A' indicates that the modified oligonucleotide is not 100% complementary to that particular gene sequence. The values marked with an asterisk (*) indicate that the modified oligonucleotide is complementary to the amplicon region of the primer probe set.

Cultured A-431 cells at a density of 10,000 cells per well, were treated with modified oligonucleotide at a concentration of 4,000 nM using free uptake for a treatment period of 48 hours. At the end of the treatment period, total RNA was isolated from the cells and FUS RNA levels were measured by quantitative real-time PCR. FUS RNA levels were measured by Human FUS primer probe set RTS38562 (forward sequence TGCTTGCTTGCCTGTGC, designated herein as SEQ ID NO: 6; reverse sequence ACTGTAACTCTGCTGTCCGT, designated herein as SEQ ID NO: 7; probe sequence TTGAGGCCATGTCCGCGC, designated herein as SEQ ID NO: 8). FUS RNA levels were normalized to total RNA content, as measured by RIBOGREEN®.

TABLE 1

Reduction of FUS RNA by 5-10-5 MOE gapmers with mixed PO/PS linkages complementary to human FUS

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043279 | 51 | 70 | 4160 | 4179 | AGTTCCAACACCGCTGAGTA | 40 | 14 |
| 1043285 | 91 | 110 | 4200 | 4219 | GCCATGTCCGCGCACGCGCG | 7* | 15 |

TABLE 1-continued

Reduction of FUS RNA by 5-10-5 MOE gapmers with mixed PO/PS linkages complementary to human FUS

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043291 | 218 | 237 | 6587 | 6606 | GGACTGGCTATAACCACTGT | 74* | 16 |
| 1043297 | 266 | 285 | 6635 | 6654 | CTGGCCATAAGAAGAATAGC | 111 | 17 |
| 1043303 | 330 | 349 | 7892 | 7911 | CATAGCCGCCAGTCGAGCCA | 98 | 18 |
| 1043309 | 362 | 381 | 7924 | 7943 | CCCGTAAGACGATTGGGAGC | 105 | 19 |
| 1043315 | 439 | 458 | 8207 | 8226 | TGAGAACTGCTACCGTAACT | 43 | 20 |
| 1043321 | 505 | 524 | 8273 | 8292 | TGCTGTCCACCATAGCTAGG | 74 | 21 |
| 1043327 | 648 | 667 | 8958 | 8977 | CACCACTACTCATGGAGGAT | 36 | 22 |
| 1043333 | 719 | 738 | 9029 | 9048 | CTGCTGTCCATAGCCACCGC | 53 | 23 |
| 1043339 | 788 | 807 | 9098 | 9117 | GCGGTTGTAACCACCACCGC | 87 | 24 |
| 1043345 | 1198 | 1217 | 14066 | 14085 | CGAGTAGCAAATGAGACCTT | 67 | 25 |
| 1043351 | 1225 | 1244 | 14093 | 14112 | CCACCACCCCGATTAAAGTC | 55 | 26 |
| 1043357 | 1320 | 1339 | 14321 | 14340 | TGGGAAATCCTCCTCGGCCA | 96 | 27 |
| 1043363 | 1505 | 1524 | 14969 | 14988 | ACGACGATCATCCCCGTAGT | 55 | 28 |
| 1043369 | 1534 | 1553 | 14998 | 15017 | CCGCCTCGATCATAGCCTCC | 52 | 29 |
| 1043375 | 1544 | 1563 | 15008 | 15027 | GCCCCGGTAGCCGCCTCGAT | 68 | 30 |
| 1043381 | 1667 | 1686 | 15419 | 15438 | TTAATACGGCCTCTCCCTGC | 87 | 31 |
| 1043387 | 1676 | 1695 | 15428 | 15447 | CCAGGCTAATTAATACGGCC | 105 | 32 |
| 1043393 | 1781 | 1800 | 15533 | 15552 | TAGTCCGACACAAAAAAACC | 66 | 33 |
| 1043397 | 1792 | 1811 | 15544 | 15563 | TTACAATTACATAGTCCGAC | 6 | 34 |
| 1043400 | 1808 | 1827 | 15560 | 15579 | GGAACCAGAGGTATAGTTAC | 35 | 35 |
| 1043406 | 1883 | 1902 | 15635 | 15654 | TCGGGACATCGATCTTCCAG | 103 | 36 |
| 1043412 | 1922 | 1941 | 15674 | 15693 | GCAGGGTAATCTGAACAGGA | 91 | 37 |
| 1043418 | 1964 | 1983 | 15716 | 15735 | ATTTGGCCTTCTCCCCGAAC | 104 | 38 |
| 1043424 | 2061 | 2080 | 15813 | 15832 | TAGGCCAACACTCATGACAT | 76 | 39 |
| 1043430 | 2334 | 2353 | 16086 | 16105 | GAGTCACTCACCTCCTAGAT | 107 | 40 |
| 1043436 | 2448 | 2467 | 16200 | 16219 | GTCAATGACCTCAAGCCCTC | 63 | 41 |
| 1043442 | 2606 | 2625 | 16358 | 16377 | CGTGCAAGTTTACAACCACA | 72 | 42 |
| 1043448 | 2718 | 2737 | 16470 | 16489 | TCTTACAAACCAAGTTCGAA | 94 | 43 |
| 1043454 | 3471 | 3490 | 17223 | 17242 | GGAAGTAAACCTGCTATTCC | 98 | 44 |
| 1043460 | 3519 | 3538 | 17271 | 17290 | ACCACTCTCCGCCTACTGTT | 79 | 45 |
| 1043466 | 3531 | 3550 | 17283 | 17302 | TTAATACGCCAGACCACTCT | 105 | 46 |
| 1043472 | 3553 | 3572 | 17305 | 17324 | CCCACTTGACGATCCTTTGT | 83 | 47 |
| 1043478 | 3681 | 3700 | 17433 | 17452 | AGTGAACTACTCAAATATCG | 71 | 48 |
| 1043484 | 3794 | 3813 | 17546 | 17565 | GGTCCCAGTAATCATATCTT | 81 | 49 |
| 1043490 | 3841 | 3860 | 17593 | 17612 | GGCCAATCACATATGCCATT | 96 | 50 |

TABLE 1-continued

Reduction of FUS RNA by 5-10-5 MOE gapmers with mixed PO/PS linkages complementary to human FUS

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043496 | 3895 | 3914 | 17647 | 17666 | ACTGGACCTACCCACTAAAC | 99 | 51 |
| 1043502 | 4232 | 4251 | 17984 | 18003 | TGGGACACCTAATGCTTCAA | 78 | 52 |
| 1043508 | 4404 | 4423 | 18156 | 18175 | GCAGCCCTACATCCAAGTAC | 94 | 53 |
| 1043514 | 4434 | 4453 | 18186 | 18205 | CTGGTCAATCTACCCACCAC | 92 | 54 |
| 1043520 | 4450 | 4469 | 18202 | 18221 | CCCTAGACCTTAATTCCTGG | 102 | 55 |
| 1043526 | 4841 | 4860 | 18593 | 18612 | ATTTTCATAGCCGGACACAG | 77 | 56 |
| 1043532 | N/A | N/A | 3749 | 3768 | TGGCCGGGCCCCTTCGCTGG | 91 | 57 |
| 1043538 | N/A | N/A | 3887 | 3906 | CGATCTATCTCCACCCCCAT | 114 | 58 |
| 1043544 | N/A | N/A | 3901 | 3920 | GCAGGACTAGCCCACGATCT | 84 | 59 |
| 1043550 | N/A | N/A | 4104 | 4123 | GTCGAAGCTTAAGTACGCTC | 113 | 60 |
| 1043556 | N/A | N/A | 4225 | 4244 | CTCGCGCCCTTACCTACCGT | 98* | 61 |
| 1043562 | N/A | N/A | 4290 | 4309 | CCCGGTCCCACTGAAAACGA | 97 | 62 |
| 1043568 | N/A | N/A | 4417 | 4436 | AGACTTCCCGCCCCGCGCGC | 88 | 63 |
| 1043574 | N/A | N/A | 4755 | 4774 | GGAGCGATCCCGCCCATTCG | 104 | 64 |
| 1043580 | N/A | N/A | 4838 | 4857 | CCACCGCCGCCAAACCGTTA | 101 | 65 |
| 1043586 | N/A | N/A | 4871 | 4890 | GGGCCGTCCCCAAGTCCGTT | 106 | 66 |
| 1043592 | N/A | N/A | 5238 | 5257 | CGGCCGTTCTTCTCCGTCCC | 94 | 67 |
| 1043598 | N/A | N/A | 5543 | 5562 | GGCTTTTTAGTGCAAAGCCA | 81 | 68 |
| 1043604 | N/A | N/A | 5775 | 5794 | GTGATTGCTCTAAAACATCG | 72 | 69 |
| 1043610 | N/A | N/A | 7636 | 7655 | AGTTCCAATTTCACCCCGCC | 38 | 70 |
| 1043616 | N/A | N/A | 7989 | 8008 | CCGTACCTTCCCGAGGTGCT | 111 | 71 |
| 1043622 | N/A | N/A | 7999 | 8018 | ATCAACACCACCGTACCTTC | 94 | 72 |
| 1043628 | N/A | N/A | 8931 | 8950 | GGCCATAGTTACCTGTGAGA | 80 | 73 |
| 1043634 | N/A | N/A | 9507 | 9526 | ATCATCGGTTTCCCTTGCAG | 5 | 74 |
| 1043640 | N/A | N/A | 9721 | 9740 | GCTTACTTCAGTCAGCTGGC | 19 | 75 |
| 1043646 | N/A | N/A | 10220 | 10239 | GTCACCCCTTCTACACTGCG | 15 | 76 |
| 1043652 | N/A | N/A | 10443 | 10462 | GTTGGTTTAAAAACCCTACC | 80 | 77 |
| 1043658 | N/A | N/A | 10999 | 11018 | TACCTGCTCCAGGTTAGCAC | 80 | 78 |
| 1043664 | N/A | N/A | 11075 | 11094 | TCCAAGGCCTACTAGACCCC | 71 | 79 |
| 1043670 | N/A | N/A | 11315 | 11334 | TCATTGACACCATTCCGTAC | 25 | 80 |
| 1043676 | N/A | N/A | 11467 | 11486 | GGTCCACGAATTCAGTTTGT | 47 | 81 |
| 1043682 | N/A | N/A | 11812 | 11831 | GTTGTTTCCCCGAAACCACA | 85 | 82 |
| 1043688 | N/A | N/A | 11932 | 11951 | TGGGCTCGCCACCAGCCATG | 75 | 83 |
| 1043694 | N/A | N/A | 12159 | 12178 | CCAAACCCTTTCCTGGGTCG | 96 | 84 |
| 1043700 | N/A | N/A | 12564 | 12583 | GGGTCCTCTCAGACCTAAAT | 99 | 85 |
| 1043706 | N/A | N/A | 13418 | 13437 | GGTACTCTGATAAGTTATAC | 51 | 86 |

TABLE 1-continued

Reduction of FUS RNA by 5-10-5 MOE gapmers with mixed PO/PS linkages complementary to human FUS

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043712 | N/A | N/A | 13842 | 13861 | GGCTTGTTTCCTAAGGCTTG | 101 | 87 |
| 1043718 | N/A | N/A | 14454 | 14473 | CGCACATACCTCAGTACCAA | 53 | 88 |
| 1043724 | N/A | N/A | 14899 | 14918 | GTTCCCCGAGCCTCCCCGCT | 102 | 89 |
| 1043730 | N/A | N/A | 15154 | 15173 | ACCCTGTTATCCTATGGCCT | 83 | 90 |
| 1043736 | N/A | N/A | 15301 | 15320 | CCCTCCTACCTAACCCAGCG | 90 | 91 |

TABLE 2

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043280 | 54 | 73 | 4163 | 4182 | CGAAGTTCCAACACCGCTGA | 45 | 92 |
| 1043286 | 98 | 117 | 4207 | 4226 | GTTTGAGGCCATGTCCGCGC | 15* | 93 |
| 1043292 | 233 | 252 | 6602 | 6621 | GCCTGAAGTGTCCGTGGACT | 86 | 94 |
| 1043298 | 321 | 340 | 7883 | 7902 | CAGTCGAGCCATATCCCTGG | 74 | 95 |
| 1043304 | 333 | 352 | 7895 | 7914 | TGCCATAGCCGCCAGTCGAG | 82 | 96 |
| 1043310 | 363 | 382 | 7925 | 7944 | GCCCGTAAGACGATTGGGAG | 94 | 97 |
| 1043316 | 494 | 513 | 8262 | 8281 | ATAGCTAGGCTGCTGGCTGT | 89 | 98 |
| 1043322 | 506 | 525 | 8274 | 8293 | CTGCTGTCCACCATAGCTAG | 88 | 99 |
| 1043328 | 678 | 697 | 8988 | 9007 | CTTGATTGCCATAACCGCCA | 37 | 100 |
| 1043334 | 720 | 739 | 9030 | 9049 | CCTGCTGTCCATAGCCACCG | 36 | 101 |
| 1043340 | 789 | 808 | 9099 | 9118 | TGCGGTTGTAACCACCACCG | 48 | 102 |
| 1043346 | 1199 | 1218 | 14067 | 14086 | GCGAGTAGCAAATGAGACCT | 52 | 103 |
| 1043352 | 1226 | 1245 | 14094 | 14113 | GCCACCACCCCGATTAAAGT | 36 | 104 |
| 1043358 | 1322 | 1341 | 14323 | 14342 | ACTGGGAAATCCTCCTCGGC | 94 | 105 |
| 1043364 | 1506 | 1525 | 14970 | 14989 | CACGACGATCATCCCCGTAG | 56 | 106 |
| 1043370 | 1535 | 1554 | 14999 | 15018 | GCCGCCTCGATCATAGCCTC | 91 | 107 |
| 1043376 | 1567 | 1586 | 15031 | 15050 | AAGCCTCCACGGTCCCCGCC | 83 | 108 |
| 1043382 | 1668 | 1687 | 15420 | 15439 | ATTAATACGGCCTCTCCCTG | 92 | 109 |
| 1043388 | 1677 | 1696 | 15429 | 15448 | GCCAGGCTAATTAATACGGC | 89 | 110 |
| 1043394 | 1786 | 1805 | 15538 | 15557 | TTACATAGTCCGACACAAAA | 38 | 111 |
| 1043397 | 1792 | 1811 | 15544 | 15563 | TTACAATTACATAGTCCGAC | 6 | 34 |
| 1043401 | 1822 | 1841 | 15574 | 15593 | GGTCACTTTTAATGGGAACC | 9 | 112 |
| 1043407 | 1885 | 1904 | 15637 | 15656 | GATCGGGACATCGATCTTCC | 121 | 113 |

TABLE 2-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043413 | 1958 | 1977 | 15710 | 15729 | CCTTCTCCCCGAACACTGTA | 78 | 114 |
| 1043419 | 1965 | 1984 | 15717 | 15736 | CATTTGGCCTTCTCCCCGAA | 94 | 115 |
| 1043425 | 2062 | 2081 | 15814 | 15833 | TTAGGCCAACACTCATGACA | 84 | 116 |
| 1043431 | 2335 | 2354 | 16087 | 16106 | GGAGTCACTCACCTCCTAGA | 103 | 117 |
| 1043437 | 2487 | 2506 | 16239 | 16258 | CCTCCAATCAAAAAGGGATC | 94 | 118 |
| 1043443 | 2661 | 2680 | 16413 | 16432 | GTTACGCTCTGTGTAACTAA | 84 | 119 |
| 1043449 | 2719 | 2738 | 16471 | 16490 | GTCTTACAAACCAAGTTCGA | 82 | 120 |
| 1043455 | 3494 | 3513 | 17246 | 17265 | GAGAGCACCCCAATGCTGGC | 110 | 121 |
| 1043461 | 3520 | 3539 | 17272 | 17291 | GACCACTCTCCGCCTACTGT | 90 | 122 |
| 1043467 | 3533 | 3552 | 17285 | 17304 | TTTTAATACGCCAGACCACT | 85 | 123 |
| 1043473 | 3554 | 3573 | 17306 | 17325 | GCCCACTTGACGATCCTTTG | 103 | 124 |
| 1043479 | 3689 | 3708 | 17441 | 17460 | GCACCAACAGTGAACTACTC | 101 | 125 |
| 1043485 | 3796 | 3815 | 17548 | 17567 | ATGGTCCCAGTAATCATATC | 104 | 126 |
| 1043491 | 3846 | 3865 | 17598 | 17617 | GTCAAGGCCAATCACATATG | 86 | 127 |
| 1043497 | 3896 | 3915 | 17648 | 17667 | AACTGGACCTACCCACTAAA | 98 | 128 |
| 1043503 | 4233 | 4252 | 17985 | 18004 | ATGGGACACCTAATGCTTCA | 73 | 129 |
| 1043509 | 4405 | 4424 | 18157 | 18176 | TGCAGCCCTACATCCAAGTA | 98 | 130 |
| 1043515 | 4444 | 4463 | 18196 | 18215 | ACCTTAATTCCTGGTCAATC | 91 | 131 |
| 1043521 | 4452 | 4471 | 18204 | 18223 | GACCCTAGACCTTAATTCCT | 118 | 132 |
| 1043527 | N/A | N/A | 3462 | 3481 | CCCGGATCCTCATGGCTTTG | 105 | 133 |
| 1043533 | N/A | N/A | 3750 | 3769 | GTGGCCGGGCCCCTTCGCTG | 102 | 134 |
| 1043539 | N/A | N/A | 3892 | 3911 | GCCCACGATCTATCTCCACC | 107 | 135 |
| 1043545 | N/A | N/A | 4029 | 4048 | GGAACGCACTCCGCCCCCTT | 75 | 136 |
| 1043551 | N/A | N/A | 4220 | 4239 | GCCCTTACCTACCGTTTGAG | 99* | 137 |
| 1043557 | N/A | N/A | 4226 | 4245 | CCTCGCGCCCTTACCTACCG | 89* | 138 |
| 1043563 | N/A | N/A | 4304 | 4323 | CACGGGATCGCCGCCCCGGT | 90 | 139 |
| 1043569 | N/A | N/A | 4672 | 4691 | CTCGCGACAGAAAGCTGAAC | 106 | 140 |
| 1043575 | N/A | N/A | 4756 | 4775 | CGGAGCGATCCCGCCCATTC | 71 | 141 |
| 1043581 | N/A | N/A | 4839 | 4858 | ACCACCGCCGCCAAACCGTT | 82 | 142 |
| 1043587 | N/A | N/A | 4873 | 4892 | TCGGGCCGTCCCCAAGTCCG | 108 | 143 |
| 1043593 | N/A | N/A | 5239 | 5258 | GCGGCCGTTCTTCTCCGTCC | 113 | 144 |
| 1043599 | N/A | N/A | 5572 | 5591 | ACTCTTTGACCAATCCCGGA | 76 | 145 |
| 1043605 | N/A | N/A | 5815 | 5834 | GGTGGACATCCACAATTTTC | 93 | 146 |
| 1043611 | N/A | N/A | 7637 | 7656 | CAGTTCCAATTTCACCCCGC | 42 | 147 |
| 1043617 | N/A | N/A | 7990 | 8009 | ACCGTACCTTCCCGAGGTGC | 94 | 148 |
| 1043623 | N/A | N/A | 8004 | 8023 | CCGACATCAACACCACCGTA | 103 | 149 |

TABLE 2-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043629 | N/A | N/A | 8933 | 8952 | TTGGCCATAGTTACCTGTGA | 89 | 150 |
| 1043635 | N/A | N/A | 9587 | 9606 | TCAGGTTAACCATTACCAAC | 41 | 151 |
| 1043641 | N/A | N/A | 9926 | 9945 | GTAGGGTCCTTCAAATCTTA | 7 | 152 |
| 1043647 | N/A | N/A | 10221 | 10240 | GGTCACCCCTTCTACACTGC | 17 | 153 |
| 1043653 | N/A | N/A | 10459 | 10478 | GGTTGACAACCAAGTAGTTG | 9 | 154 |
| 1043659 | N/A | N/A | 11014 | 11033 | ATTGAGTCTTACCCCTACCT | 49 | 155 |
| 1043665 | N/A | N/A | 11076 | 11095 | GTCCAAGGCCTACTAGACCC | 52 | 156 |
| 1043671 | N/A | N/A | 11316 | 11335 | TTCATTGACACCATTCCGTA | 25 | 157 |
| 1043677 | N/A | N/A | 11621 | 11640 | CACCTAAGTCATGAACCCAC | 52 | 158 |
| 1043683 | N/A | N/A | 11816 | 11835 | CCGTGTTGTTTCCCCGAAAC | 9 | 159 |
| 1043689 | N/A | N/A | 11935 | 11954 | AGATGGGCTCGCCACCAGCC | 86 | 160 |
| 1043695 | N/A | N/A | 12309 | 12328 | GGGCCTTTAGTGACATGGAA | 117 | 161 |
| 1043701 | N/A | N/A | 12794 | 12813 | GGTCCCCGAATTAAATAAGA | 89 | 162 |
| 1043707 | N/A | N/A | 13608 | 13627 | GCTACAGTACTCCCTTTCCA | 91 | 163 |
| 1043713 | N/A | N/A | 13985 | 14004 | GCAAGACACATTAATCCGAA | 106 | 164 |
| 1043719 | N/A | N/A | 14455 | 14474 | ACGCACATACCTCAGTACCA | 31 | 165 |
| 1043725 | N/A | N/A | 14911 | 14930 | CCATTCCCCTATGTTCCCCG | 107 | 166 |
| 1043731 | N/A | N/A | 15155 | 15174 | AACCCTGTTATCCTATGGCC | 81 | 167 |
| 1043737 | N/A | N/A | 15318 | 15337 | CTAGATATCCTATCTGCCCC | 84 | 168 |

TABLE 3

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043281 | 55 | 74 | 4164 | 4183 | ACGAAGTTCCAACACCGCTG | 18 | 169 |
| 1043287 | 167 | 186 | 6536 | 6555 | CTGGGAATAGCCCTGCCCGG | 48* | 170 |
| 1043293 | 236 | 255 | 6605 | 6624 | ATAGCCTGAAGTGTCCGTGG | 54 | 171 |
| 1043299 | 322 | 341 | 7884 | 7903 | CCAGTCGAGCCATATCCCTG | 59 | 172 |
| 1043305 | 335 | 354 | 7897 | 7916 | ACTGCCATAGCCGCCAGTCG | 104 | 173 |
| 1043311 | 364 | 383 | 7926 | 7945 | TGCCCGTAAGACGATTGGGA | 97 | 174 |
| 1043317 | 496 | 515 | 8264 | 8283 | CCATAGCTAGGCTGCTGGCT | 63 | 175 |
| 1043323 | 507 | 526 | 8275 | 8294 | GCTGCTGTCCACCATAGCTA | 44 | 176 |
| 1043329 | 679 | 698 | 8989 | 9008 | TCTTGATTGCCATAACCGCC | 64 | 177 |

TABLE 3-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043335 | 724 | 743 | 9034 | 9053 | CGGTCCTGCTGTCCATAGCC | 62 | 178 |
| 1043341 | 991 | 1010 | 13176 | 13195 | GCCACAGACTCAATTGTAAC | 36 | 179 |
| 1043347 | 1215 | 1234 | 14083 | 14102 | GATTAAAGTCTGCCCGGCGA | 102 | 180 |
| 1043353 | 1227 | 1246 | 14095 | 14114 | TGCCACCACCCCGATTAAAG | 53 | 181 |
| 1043359 | 1323 | 1342 | 14324 | 14343 | CACTGGGAAATCCTCCTCGG | 100 | 182 |
| 1043365 | 1507 | 1526 | 14971 | 14990 | CCACGACGATCATCCCCGTA | 78 | 183 |
| 1043371 | 1536 | 1555 | 15000 | 15019 | AGCCGCCTCGATCATAGCCT | 62 | 184 |
| 1043377 | 1572 | 1591 | 15036 | 15055 | CTCGGAAGCCTCCACGGTCC | 93 | 185 |
| 1043383 | 1670 | 1689 | 15422 | 15441 | TAATTAATACGGCCTCTCCC | 88 | 186 |
| 1043389 | 1678 | 1697 | 15430 | 15449 | AGCCAGGCTAATTAATACGG | 121 | 187 |
| 1043395 | 1788 | 1807 | 15540 | 15559 | AATTACATAGTCCGACACAA | 8 | 188 |
| 1043397 | 1792 | 1811 | 15544 | 15563 | TTACAATTACATAGTCCGAC | 6 | 34 |
| 1043402 | 1876 | 1895 | 15628 | 15647 | ATCGATCTTCCAGGAAAGTG | 106 | 189 |
| 1043408 | 1896 | 1915 | 15648 | 15667 | TCTACCTTCCTGATCGGGAC | 76 | 190 |
| 1043414 | 1959 | 1978 | 15711 | 15730 | GCCTTCTCCCCGAACACTGT | 105 | 191 |
| 1043420 | 1966 | 1985 | 15718 | 15737 | TCATTTGGCCTTCTCCCCGA | 78 | 192 |
| 1043426 | 2186 | 2205 | 15938 | 15957 | GCCTCACCATTAAAAGGGCC | 94 | 193 |
| 1043432 | 2336 | 2355 | 16088 | 16107 | GGGAGTCACTCACCTCCTAG | 100 | 194 |
| 1043438 | 2503 | 2522 | 16255 | 16274 | TAGGAGGGCCTTCCACCCTC | 122 | 195 |
| 1043444 | 2666 | 2685 | 16418 | 16437 | TTAATGTTACGCTCTGTGTA | 88 | 196 |
| 1043450 | 2720 | 2739 | 16472 | 16491 | TGTCTTACAAACCAAGTTCG | 104 | 197 |
| 1043456 | 3514 | 3533 | 17266 | 17285 | TCTCCGCCTACTGTTGCTTA | 104 | 198 |
| 1043462 | 3525 | 3544 | 17277 | 17296 | CGCCAGACCACTCTCCGCCT | 28 | 199 |
| 1043468 | 3534 | 3553 | 17286 | 17305 | TTTTTAATACGCCAGACCAC | 112 | 200 |
| 1043474 | 3557 | 3576 | 17309 | 17328 | AAGGCCCACTTGACGATCCT | 92 | 201 |
| 1043480 | 3711 | 3730 | 17463 | 17482 | GATTAGAATCCTGCTAGGCA | 89 | 202 |
| 1043486 | 3807 | 3826 | 17559 | 17578 | ACTTGACACTAATGGTCCCA | 91 | 203 |
| 1043492 | 3891 | 3910 | 17643 | 17662 | GACCTACCCACTAAACAGTC | 97 | 204 |
| 1043498 | 3898 | 3917 | 17650 | 17669 | CAAACTGGACCTACCCACTA | 102 | 205 |
| 1043504 | 4263 | 4282 | 18015 | 18034 | CTTAGCCTGTCCCAATTCCA | 106 | 206 |
| 1043510 | 4406 | 4425 | 18158 | 18177 | CTGCAGCCCTACATCCAAGT | 109 | 207 |
| 1043516 | 4445 | 4464 | 18197 | 18216 | GACCTTAATTCCTGGTCAAT | 129 | 208 |
| 1043522 | 4453 | 4472 | 18205 | 18224 | GGACCCTAGACCTTAATTCC | 104 | 209 |
| 1043528 | N/A | N/A | 3463 | 3482 | ACCCGGATCCTCATGGCTTT | 100 | 210 |
| 1043534 | N/A | N/A | 3762 | 3781 | ACCGAGATTCCTGTGGCCGG | 96 | 211 |
| 1043540 | N/A | N/A | 3893 | 3912 | AGCCCACGATCTATCTCCAC | 75 | 212 |

TABLE 3-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043546 | N/A | N/A | 4087 | 4106 | CTCCGCCGCCTACGCACCGC | 97 | 213 |
| 1043552 | N/A | N/A | 4221 | 4240 | CGCCCTTACCTACCGTTTGA | 94* | 214 |
| 1043558 | N/A | N/A | 4227 | 4246 | GCCTCGCGCCCTTACCTACC | 90* | 215 |
| 1043564 | N/A | N/A | 4340 | 4359 | CGCGGCTTCCCGCCACAGGG | 95 | 216 |
| 1043570 | N/A | N/A | 4710 | 4729 | CACACCGGACGCGCGCCGCC | 103 | 217 |
| 1043576 | N/A | N/A | 4760 | 4779 | GGAACGGAGCGATCCCGCCC | 133 | 218 |
| 1043582 | N/A | N/A | 4848 | 4867 | CGAACCCTGACCACCGCCGC | 100 | 219 |
| 1043588 | N/A | N/A | 4877 | 4896 | ACTCTCGGGCCGTCCCCAAG | 115 | 220 |
| 1043594 | N/A | N/A | 5349 | 5368 | AGCCCCACTTAAGATACACG | 115 | 221 |
| 1043600 | N/A | N/A | 5664 | 5683 | CAGGTTTGAATTCGAACAGT | 48 | 222 |
| 1043606 | N/A | N/A | 5914 | 5933 | CGTTATCAGCCAAGTGTTCT | 85 | 223 |
| 1043612 | N/A | N/A | 7654 | 7673 | CTACCAACTCTTTAGTACAG | 58 | 224 |
| 1043618 | N/A | N/A | 7991 | 8010 | CACCGTACCTTCCCGAGGTG | 85 | 225 |
| 1043624 | N/A | N/A | 8005 | 8024 | CCCGACATCAACACCACCGT | 97 | 226 |
| 1043630 | N/A | N/A | 9178 | 9197 | GGCTCATGAGACACCTACCC | 75 | 227 |
| 1043636 | N/A | N/A | 9588 | 9607 | GTCAGGTTAACCATTACCAA | 9 | 228 |
| 1043642 | N/A | N/A | 10012 | 10031 | CTTACCATTTCCAAACTCGG | 36 | 229 |
| 1043648 | N/A | N/A | 10222 | 10241 | GGGTCACCCCTTCTACACTG | 95 | 230 |
| 1043654 | N/A | N/A | 10956 | 10975 | TACCCTACCCCTTTCTGGAG | 76 | 231 |
| 1043660 | N/A | N/A | 11060 | 11079 | ACCCCTCTTATTAACCTGGG | 56 | 232 |
| 1043666 | N/A | N/A | 11087 | 11106 | GCAACGGCCCAGTCCAAGGC | 67 | 233 |
| 1043672 | N/A | N/A | 11368 | 11387 | GAGCTAGTTTCTATTTGCCC | 24 | 234 |
| 1043678 | N/A | N/A | 11623 | 11642 | GACACCTAAGTCATGAACCC | 35 | 235 |
| 1043684 | N/A | N/A | 11829 | 11848 | ACCATCCTTAAAACCGTGTT | 7 | 236 |
| 1043690 | N/A | N/A | 11961 | 11980 | CCCGGTTCTCTCACCCGAGA | 96 | 237 |
| 1043696 | N/A | N/A | 12314 | 12333 | CCCGAGGGCCTTTAGTGACA | 62 | 238 |
| 1043702 | N/A | N/A | 13033 | 13052 | CCTAGTATCCATCAAGCAAC | 69 | 239 |
| 1043708 | N/A | N/A | 13791 | 13810 | GCCTTCTCATACATACCATC | 105 | 240 |
| 1043714 | N/A | N/A | 13986 | 14005 | TGCAAGACACATTAATCCGA | 129 | 241 |
| 1043720 | N/A | N/A | 14534 | 14553 | ACATCAACCTTACCTAGGTA | 82 | 242 |
| 1043726 | N/A | N/A | 14957 | 14976 | CCCGTAGTTACCCCCTAGGA | 75 | 243 |
| 1043732 | N/A | N/A | 15284 | 15303 | GCGAGTATCTTATCTCAAGT | 54 | 244 |
| 1043738 | N/A | N/A | 15319 | 15338 | CCTAGATATCCTATCTGCCC | 87 | 245 |

TABLE 4

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043282 | 56 | 75 | 4165 | 4184 | AACGAAGTTCCAACACCGCT | 49* | 246 |
| 1043288 | 197 | 216 | 6566 | 6585 | ACTCTGCTGTCCGTAGGGCT | 8* | 247 |
| 1043294 | 240 | 259 | 6609 | 6628 | GGCCATAGCCTGAAGTGTCC | 85 | 248 |
| 1043300 | 323 | 342 | 7885 | 7904 | GCCAGTCGAGCCATATCCCT | 59 | 249 |
| 1043306 | 339 | 358 | 7901 | 7920 | GGCTACTGCCATAGCCGCCA | 97 | 250 |
| 1043312 | 370 | 389 | 7932 | 7951 | GACTGCTGCCCGTAAGACGA | 48 | 251 |
| 1043318 | 497 | 516 | 8265 | 8284 | ACCATAGCTAGGCTGCTGGC | 56 | 252 |
| 1043324 | 627 | 646 | 8937 | 8956 | GATCTTGGCCATAGTTACCT | 40 | 253 |
| 1043330 | 680 | 699 | 8990 | 9009 | GTCTTGATTGCCATAACCGC | 44 | 254 |
| 1043336 | 727 | 746 | 9037 | 9056 | CCACGGTCCTGCTGTCCATA | 45 | 255 |
| 1043342 | 1045 | 1064 | 13668 | 13687 | GGCTGTCCCGTTTTCTTGTT | 55 | 256 |
| 1043348 | 1221 | 1240 | 14089 | 14108 | CACCCCGATTAAAGTCTGCC | 97 | 257 |
| 1043354 | 1243 | 1262 | 14111 | 14130 | CGGCCTCCACGACCATTGCC | 95 | 258 |
| 1043360 | 1377 | 1396 | 14378 | 14397 | GATTAGGACACTTCCAGTCA | 92 | 259 |
| 1043366 | 1508 | 1527 | 14972 | 14991 | ACCACGACGATCATCCCCGT | 71 | 260 |
| 1043372 | 1537 | 1556 | 15001 | 15020 | TAGCCGCCTCGATCATAGCC | 68 | 261 |
| 1043378 | 1573 | 1592 | 15037 | 15056 | CCTCGGAAGCCTCCACGGTC | 87 | 262 |
| 1043384 | 1671 | 1690 | 15423 | 15442 | CTAATTAATACGGCCTCTCC | 103 | 263 |
| 1043390 | 1739 | 1758 | 15491 | 15510 | GGTTACAAAATAACGAGGGT | 5 | 264 |
| 1043396 | 1789 | 1808 | 15541 | 15560 | CAATTACATAGTCCGACACA | 33 | 265 |
| 1043397 | 1792 | 1811 | 15544 | 15563 | TTACAATTACATAGTCCGAC | 6 | 34 |
| 1043403 | 1879 | 1898 | 15631 | 15650 | GACATCGATCTTCCAGGAAA | 80 | 266 |
| 1043409 | 1897 | 1916 | 15649 | 15668 | CTCTACCTTCCTGATCGGGA | 111 | 267 |
| 1043415 | 1960 | 1979 | 15712 | 15731 | GGCCTTCTCCCCGAACACTG | 62 | 268 |
| 1043421 | 1976 | 1995 | 15728 | 15747 | CTCAAGGATATCATTTGGCC | 81 | 269 |
| 1043427 | 2242 | 2261 | 15994 | 16013 | CGCTCTCCACCATGGTCAAA | 80 | 270 |
| 1043433 | 2396 | 2415 | 16148 | 16167 | CAGACCAGTCTCCTTATAGC | 62 | 271 |
| 1043439 | 2504 | 2523 | 16256 | 16275 | TTAGGAGGGCCTTCCACCCT | 112 | 272 |
| 1043445 | 2668 | 2687 | 16420 | 16439 | GGTTAATGTTACGCTCTGTG | 24 | 273 |
| 1043451 | 3153 | 3172 | 16905 | 16924 | GCAACTCTTCAGTAGAGAAC | 81 | 274 |
| 1043457 | 3516 | 3535 | 17268 | 17287 | ACTCTCCGCCTACTGTTGCT | 99 | 275 |
| 1043463 | 3526 | 3545 | 17278 | 17297 | ACGCCAGACCACTCTCCGCC | 92 | 276 |
| 1043469 | 3535 | 3554 | 17287 | 17306 | GTTTTTAATACGCCAGACCA | 71 | 277 |
| 1043475 | 3560 | 3579 | 17312 | 17331 | GGGAAGGCCCACTTGACGAT | 92 | 278 |
| 1043481 | 3712 | 3731 | 17464 | 17483 | AGATTAGAATCCTGCTAGGC | 116 | 279 |
| 1043487 | 3808 | 3827 | 17560 | 17579 | AACTTGACACTAATGGTCCC | 110 | 280 |

TABLE 4-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043493 | 3892 | 3911 | 17644 | 17663 | GGACCTACCCACTAAACAGT | 96 | 281 |
| 1043499 | 3907 | 3926 | 17659 | 17678 | AGATCCCCCCAAACTGGACC | 62 | 282 |
| 1043505 | 4267 | 4286 | 18019 | 18038 | CCTACTTAGCCTGTCCCAAT | 94 | 283 |
| 1043511 | 4431 | 4450 | 18183 | 18202 | GTCAATCTACCCACCACTGA | 94 | 284 |
| 1043517 | 4446 | 4465 | 18198 | 18217 | AGACCTTAATTCCTGGTCAA | 125 | 285 |
| 1043523 | 4458 | 4477 | 18210 | 18229 | GGGCTGGACCCTAGACCTTA | 118 | 286 |
| 1043529 | N/A | N/A | 3464 | 3483 | CACCCGGATCCTCATGGCTT | 80 | 287 |
| 1043535 | N/A | N/A | 3763 | 3782 | AACCGAGATTCCTGTGGCCG | 134 | 288 |
| 1043541 | N/A | N/A | 3894 | 3913 | TAGCCCACGATCTATCTCCA | 87 | 289 |
| 1043547 | N/A | N/A | 4088 | 4107 | GCTCCGCCGCCTACGCACCG | 94 | 290 |
| 1043553 | N/A | N/A | 4222 | 4241 | GCGCCCTTACCTACCGTTTG | 83* | 291 |
| 1043559 | N/A | N/A | 4229 | 4248 | TCGCCTCGCGCCCTTACCTA | 91 | 292 |
| 1043565 | N/A | N/A | 4341 | 4360 | CCGCGGCTTCCCGCCACAGG | 104 | 293 |
| 1043571 | N/A | N/A | 4716 | 4735 | AAGGCTCACACCGGACGCGC | 89 | 294 |
| 1043577 | N/A | N/A | 4802 | 4821 | CGATCCCGAGCCTCCGCCCC | 92 | 295 |
| 1043583 | N/A | N/A | 4851 | 4870 | GGTCGAACCCTGACCACCGC | 90 | 296 |
| 1043589 | N/A | N/A | 5234 | 5253 | CGTTCTTCTCCGTCCCTATC | 112 | 297 |
| 1043595 | N/A | N/A | 5428 | 5447 | TGGGACTCCAGATGGTTCCG | 99 | 298 |
| 1043601 | N/A | N/A | 5727 | 5746 | AGCCATTATCGCCAGGAGTC | 32 | 299 |
| 1043607 | N/A | N/A | 6473 | 6492 | CGTGATCAGAAAACATGGCG | 96 | 300 |
| 1043613 | N/A | N/A | 7703 | 7722 | GCAAAGATAGTTACCCTCCT | 10 | 301 |
| 1043619 | N/A | N/A | 7992 | 8011 | CCACCGTACCTTCCCGAGGT | 72 | 302 |
| 1043625 | N/A | N/A | 8011 | 8030 | GCCTTCCCCGACATCAACAC | 79 | 303 |
| 1043631 | N/A | N/A | 9282 | 9301 | GCCCTCACAGATCCCTAGAC | 68 | 304 |
| 1043637 | N/A | N/A | 9589 | 9608 | AGTCAGGTTAACCATTACCA | 6 | 305 |
| 1043643 | N/A | N/A | 10177 | 10196 | GTCACCTTTCATACCTGTGG | 3 | 306 |
| 1043649 | N/A | N/A | 10263 | 10282 | GTCCTAACTACTGAGCTGTT | 29 | 307 |
| 1043655 | N/A | N/A | 10963 | 10982 | GGCATTCTACCCTACCCCTT | 9 | 308 |
| 1043661 | N/A | N/A | 11061 | 11080 | GACCCCTCTTATTAACCTGG | 19 | 309 |
| 1043667 | N/A | N/A | 11089 | 11108 | TGGCAACGGCCCAGTCCAAG | 76 | 310 |
| 1043673 | N/A | N/A | 11438 | 11457 | GACCTGGTTATTTCCCATGA | 22 | 311 |
| 1043679 | N/A | N/A | 11628 | 11647 | GCAATGACACCTAAGTCATG | 62 | 312 |
| 1043685 | N/A | N/A | 11830 | 11849 | AACCATCCTTAAAACCGTGT | 7 | 313 |
| 1043691 | N/A | N/A | 11962 | 11981 | GCCCGGTTCTCTCACCCGAG | 87 | 314 |
| 1043697 | N/A | N/A | 12323 | 12342 | ATCCTTGGTCCCGAGGGCCT | 100 | 315 |

TABLE 4-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043703 | N/A | N/A | 13036 | 13055 | GCACCTAGTATCCATCAAGC | 35 | 316 |
| 1043709 | N/A | N/A | 13795 | 13814 | GCCAGCCTTCTCATACATAC | 119 | 317 |
| 1043715 | N/A | N/A | 14038 | 14057 | TTCCGGAGAATTCTTTACCT | 61 | 318 |
| 1043721 | N/A | N/A | 14535 | 14554 | TACATCAACCTTACCTAGGT | 83 | 319 |
| 1043727 | N/A | N/A | 14958 | 14977 | CCCCGTAGTTACCCCCTAGG | 98 | 320 |
| 1043733 | N/A | N/A | 15285 | 15304 | AGCGAGTATCTTATCTCAAG | 61 | 321 |
| 1043739 | N/A | N/A | 15320 | 15339 | GCCTAGATATCCTATCTGCC | 95 | 322 |

TABLE 5

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043283 | 57 | 76 | 4166 | 4185 | CAACGAAGTTCCAACACCGC | 48* | 323 |
| 1043289 | 213 | 232 | 6582 | 6601 | GGCTATAACCACTGTAACTC | 11* | 324 |
| 1043295 | 241 | 260 | 6610 | 6629 | TGGCCATAGCCTGAAGTGTC | 115 | 325 |
| 1043301 | 328 | 347 | 7890 | 7909 | TAGCCGCCAGTCGAGCCATA | 119 | 326 |
| 1043307 | 340 | 359 | 7902 | 7921 | TGGCTACTGCCATAGCCGCC | 113 | 327 |
| 1043313 | 371 | 390 | 7933 | 7952 | GGACTGCTGCCCGTAAGACG | 57 | 328 |
| 1043319 | 501 | 520 | 8269 | 8288 | GTCCACCATAGCTAGGCTGC | 59 | 329 |
| 1043325 | 638 | 657 | 8948 | 8967 | CATGGAGGATTGATCTTGGC | 65 | 330 |
| 1043331 | 682 | 701 | 8992 | 9011 | TGGTCTTGATTGCCATAACC | 101 | 331 |
| 1043337 | 737 | 756 | 9047 | 9066 | GCCGCGGCCTCCACGGTCCT | 101 | 332 |
| 1043343 | 1046 | 1065 | 13669 | 13688 | GGGCTGTCCCGTTTTCTTGT | 85 | 333 |
| 1043349 | 1223 | 1242 | 14091 | 14110 | ACCACCCCGATTAAAGTCTG | 69 | 334 |
| 1043355 | 1244 | 1263 | 14112 | 14131 | TCGGCCTCCACGACCATTGC | 58 | 335 |
| 1043361 | 1502 | 1521 | 14966 | 14985 | ACGATCATCCCCGTAGTTAC | 48 | 336 |
| 1043367 | 1509 | 1528 | 14973 | 14992 | CACCACGACGATCATCCCCG | 88 | 337 |
| 1043373 | 1539 | 1558 | 15003 | 15022 | GGTAGCCGCCTCGATCATAG | 57 | 338 |
| 1043379 | 1586 | 1605 | 15050 | 15069 | ACCACCCCGGCCCCCTCGGA | 111 | 339 |
| 1043385 | 1673 | 1692 | 15425 | 15444 | GGCTAATTAATACGGCCTCT | 78 | 340 |
| 1043391 | 1740 | 1759 | 15492 | 15511 | AGGTTACAAAATAACGAGGG | 6 | 341 |
| 1043397 | 1792 | 1811 | 15544 | 15563 | TTACAATTACATAGTCCGAC | 9 | 34 |
| 1043398 | 1793 | 1812 | 15545 | 15564 | GTTACAATTACATAGTCCGA | 5 | 342 |
| 1043404 | 1881 | 1900 | 15633 | 15652 | GGGACATCGATCTTCCAGGA | 110 | 343 |

TABLE 5-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043410 | 1898 | 1917 | 15650 | 15669 | TCTCTACCTTCCTGATCGGG | 90 | 344 |
| 1043416 | 1962 | 1981 | 15714 | 15733 | TTGGCCTTCTCCCCGAACAC | 122 | 345 |
| 1043422 | 2058 | 2077 | 15810 | 15829 | GCCAACACTCATGACATCCC | 75 | 346 |
| 1043428 | 2243 | 2262 | 15995 | 16014 | GCGCTCTCCACCATGGTCAA | 113 | 347 |
| 1043434 | 2398 | 2417 | 16150 | 16169 | GCCAGACCAGTCTCCTTATA | 87 | 348 |
| 1043440 | 2557 | 2576 | 16309 | 16328 | GGTTTTAACTCATTGGCTGC | 56 | 349 |
| 1043446 | 2673 | 2692 | 16425 | 16444 | TCTTGGGTTAATGTTACGCT | 56 | 350 |
| 1043452 | 3305 | 3324 | 17057 | 17076 | TCCCAGCTATCGCTTGAACC | 98 | 351 |
| 1043458 | 3517 | 3536 | 17269 | 17288 | CACTCTCCGCCTACTGTTGC | 112 | 352 |
| 1043464 | 3528 | 3547 | 17280 | 17299 | ATACGCCAGACCACTCTCCG | 102 | 353 |
| 1043470 | 3536 | 3555 | 17288 | 17307 | TGTTTTTAATACGCCAGACC | 121 | 354 |
| 1043476 | 3561 | 3580 | 17313 | 17332 | TGGGAAGGCCCACTTGACGA | 92 | 355 |
| 1043482 | 3753 | 3772 | 17505 | 17524 | CACTCCTAACAGGAGGGCAT | 94 | 356 |
| 1043488 | 3809 | 3828 | 17561 | 17580 | GAACTTGACACTAATGGTCC | 101 | 357 |
| 1043494 | 3893 | 3912 | 17645 | 17664 | TGGACCTACCCACTAAACAG | 143 | 358 |
| 1043500 | 3935 | 3954 | 17687 | 17706 | GCTAGGTGTCTCTATCCATT | 85 | 359 |
| 1043506 | 4268 | 4287 | 18020 | 18039 | TCCTACTTAGCCTGTCCCAA | 97 | 360 |
| 1043512 | 4432 | 4451 | 18184 | 18203 | GGTCAATCTACCCACCACTG | 106 | 361 |
| 1043518 | 4447 | 4466 | 18199 | 18218 | TAGACCTTAATTCCTGGTCA | 105 | 362 |
| 1043524 | 4472 | 4491 | 18224 | 18243 | GTCAAGTCTCACATGGGCTG | 115 | 363 |
| 1043530 | N/A | N/A | 3465 | 3484 | TCACCCGGATCCTCATGGCT | 144 | 364 |
| 1043536 | N/A | N/A | 3765 | 3784 | GGAACCGAGATTCCTGTGGC | 89 | 365 |
| 1043542 | N/A | N/A | 3896 | 3915 | ACTAGCCCACGATCTATCTC | 109 | 366 |
| 1043548 | N/A | N/A | 4092 | 4111 | GTACGCTCCGCCGCCTACGC | 108 | 367 |
| 1043554 | N/A | N/A | 4223 | 4242 | CGCGCCCTTACCTACCGTTT | 100* | 368 |
| 1043560 | N/A | N/A | 4232 | 4251 | CCGTCGCCTCGCGCCCTTAC | 123 | 369 |
| 1043566 | N/A | N/A | 4342 | 4361 | TCCGCGGCTTCCCGCCACAG | 129 | 370 |
| 1043572 | N/A | N/A | 4746 | 4765 | CCGCCCATTCGCGAAGGACC | 100 | 371 |
| 1043578 | N/A | N/A | 4813 | 4832 | GAGGGCGGCCCCGATCCCGA | 88 | 372 |
| 1043584 | N/A | N/A | 4852 | 4871 | TGGTCGAACCCTGACCACCG | 127 | 373 |
| 1043590 | N/A | N/A | 5235 | 5254 | CCGTTCTTCTCCGTCCCTAT | 105 | 374 |
| 1043596 | N/A | N/A | 5479 | 5498 | AACTGCTCGCCTTAGGAGGC | 96 | 375 |
| 1043602 | N/A | N/A | 5773 | 5792 | GATTGCTCTAAAACATCGCG | 73 | 376 |
| 1043608 | N/A | N/A | 7535 | 7554 | CGTGCAGTATCTACAGGACA | 21 | 377 |
| 1043614 | N/A | N/A | 7729 | 7748 | GCTGTTAGTGATGTTGCAAC | 72 | 378 |

TABLE 5-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043620 | N/A | N/A | 7993 | 8012 | ACCACCGTACCTTCCCGAGG | 94 | 379 |
| 1043626 | N/A | N/A | 8015 | 8034 | TCAAGCCTTCCCCGACATCA | 81 | 380 |
| 1043632 | N/A | N/A | 9458 | 9477 | GCCTAGGATATTAATGACTC | 57 | 381 |
| 1043638 | N/A | N/A | 9704 | 9723 | GGCCCCATAAACCAAGTCAC | 62 | 382 |
| 1043644 | N/A | N/A | 10193 | 10212 | CGGAGTATTTTGCAATGTCA | 2 | 383 |
| 1043650 | N/A | N/A | 10305 | 10324 | AGGCAACTTCCCCTTAAAGC | 11 | 384 |
| 1043656 | N/A | N/A | 10967 | 10986 | AGGTGGCATTCTACCCTACC | 111 | 385 |
| 1043662 | N/A | N/A | 11063 | 11082 | TAGACCCCTCTTATTAACCT | 36 | 386 |
| 1043668 | N/A | N/A | 11184 | 11203 | ACAACGATCAAAAGGATCCT | 91 | 387 |
| 1043674 | N/A | N/A | 11465 | 11484 | TCCACGAATTCAGTTTGTGC | 14 | 388 |
| 1043680 | N/A | N/A | 11668 | 11687 | GTTTATCTGAATTCGCCATA | 4 | 12 |
| 1043686 | N/A | N/A | 11926 | 11945 | CGCCACCAGCCATGCGATGT | 55 | 389 |
| 1043692 | N/A | N/A | 11963 | 11982 | GGCCCGGTTCTCTCACCCGA | 69 | 390 |
| 1043698 | N/A | N/A | 12389 | 12408 | GTCTTGATACCACTTTAGCC | 39 | 391 |
| 1043704 | N/A | N/A | 13296 | 13315 | GGCAACCATTAAAGACTTGC | 46 | 392 |
| 1043710 | N/A | N/A | 13827 | 13846 | GCTTGCTGCCCTATATCCCC | 89 | 393 |
| 1043716 | N/A | N/A | 14193 | 14212 | CCATGCAAGCCTTTACCATC | 78 | 394 |
| 1043722 | N/A | N/A | 14540 | 14559 | CCCATTACATCAACCTTACC | 85 | 395 |
| 1043728 | N/A | N/A | 14960 | 14979 | ATCCCCGTAGTTACCCCCTA | 41 | 396 |
| 1043734 | N/A | N/A | 15294 | 15313 | ACCTAACCCAGCGAGTATCT | 108 | 397 |
| 1043740 | N/A | N/A | 15321 | 15340 | AGCCTAGATATCCTATCTGC | 111 | 398 |

TABLE 6

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043284 | 78 | 97 | 4187 | 4206 | ACGCGCGCACAGGCAAGCAA | 13* | 399 |
| 1043290 | 215 | 234 | 6584 | 6603 | CTGGCTATAACCACTGTAAC | 29* | 400 |
| 1043296 | 242 | 261 | 6611 | 6630 | CTGGCCATAGCCTGAAGTGT | 101 | 401 |
| 1043302 | 329 | 348 | 7891 | 7910 | ATAGCCGCCAGTCGAGCCAT | 108 | 402 |
| 1043308 | 341 | 360 | 7903 | 7922 | CTGGCTACTGCCATAGCCGC | 75 | 403 |
| 1043314 | 372 | 391 | 7934 | 7953 | AGGACTGCTGCCCGTAAGAC | 73 | 404 |
| 1043320 | 504 | 523 | 8272 | 8291 | GCTGTCCACCATAGCTAGGC | 41 | 405 |
| 1043326 | 647 | 666 | 8957 | 8976 | ACCACTACTCATGGAGGATT | 65 | 406 |

TABLE 6-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043332 | 717 | 736 | 9027 | 9046 | GCTGTCCATAGCCACCGCTG | 81 | 407 |
| 1043338 | 738 | 757 | 9048 | 9067 | TGCCGCGGCCTCCACGGTCC | 83 | 408 |
| 1043344 | 1107 | 1126 | 13730 | 13749 | AAGAGACCGTTGCCTCTCCC | 111 | 409 |
| 1043350 | 1224 | 1243 | 14092 | 14111 | CACCACCCCGATTAAAGTCT | 46 | 410 |
| 1043356 | 1245 | 1264 | 14113 | 14132 | CTCGGCCTCCACGACCATTG | 121 | 411 |
| 1043362 | 1503 | 1522 | 14967 | 14986 | GACGATCATCCCCGTAGTTA | 47 | 412 |
| 1043368 | 1529 | 1548 | 14993 | 15012 | TCGATCATAGCCTCCTCTGC | 69 | 413 |
| 1043374 | 1540 | 1559 | 15004 | 15023 | CGGTAGCCGCCTCGATCATA | 73 | 414 |
| 1043380 | 1664 | 1683 | 15416 | 15435 | ATACGGCCTCTCCCTGCGAT | 65 | 415 |
| 1043386 | 1675 | 1694 | 15427 | 15446 | CAGGCTAATTAATACGGCCT | 116 | 416 |
| 1043392 | 1763 | 1782 | 15515 | 15534 | CCCTTGGGTGATCAGGAATT | 67 | 417 |
| 1043397 | 1792 | 1811 | 15544 | 15563 | TTACAATTACATAGTCCGAC | 5 | 34 |
| 1043399 | 1794 | 1813 | 15546 | 15565 | AGTTACAATTACATAGTCCG | 4 | 418 |
| 1043405 | 1882 | 1901 | 15634 | 15653 | CGGGACATCGATCTTCCAGG | 94 | 419 |
| 1043411 | 1899 | 1918 | 15651 | 15670 | CTCTCTACCTTCCTGATCGG | 102 | 420 |
| 1043417 | 1963 | 1982 | 15715 | 15734 | TTTGGCCTTCTCCCCGAACA | 90 | 421 |
| 1043423 | 2059 | 2078 | 15811 | 15830 | GGCCAACACTCATGACATCC | 91 | 422 |
| 1043429 | 2329 | 2348 | 16081 | 16100 | ACTCACCTCCTAGATCCTGA | 93 | 423 |
| 1043435 | 2406 | 2425 | 16158 | 16177 | GTAACCCAGCCAGACCAGTC | 107 | 424 |
| 1043441 | 2558 | 2577 | 16310 | 16329 | AGGTTTTAACTCATTGGCTG | 83 | 425 |
| 1043447 | 2674 | 2693 | 16426 | 16445 | CTCTTGGGTTAATGTTACGC | 62 | 426 |
| 1043453 | 3306 | 3325 | 17058 | 17077 | ATCCCAGCTATCGCTTGAAC | 110 | 427 |
| 1043459 | 3518 | 3537 | 17270 | 17289 | CCACTCTCCGCCTACTGTTG | 81 | 428 |
| 1043465 | 3529 | 3548 | 17281 | 17300 | AATACGCCAGACCACTCTCC | 124 | 429 |
| 1043471 | 3551 | 3570 | 17303 | 17322 | CACTTGACGATCCTTTGTTT | 77 | 430 |
| 1043477 | 3662 | 3681 | 17414 | 17433 | GTATCAGGCCATTTCAACTA | 62 | 431 |
| 1043483 | 3773 | 3792 | 17525 | 17544 | CAAGGAGCTTCGACCTCCTC | 150 | 432 |
| 1043489 | 3810 | 3829 | 17562 | 17581 | GGAACTTGACACTAATGGTC | 106 | 433 |
| 1043495 | 3894 | 3913 | 17646 | 17665 | CTGGACCTACCCACTAAACA | 119 | 434 |
| 1043501 | 3937 | 3956 | 17689 | 17708 | CTGCTAGGTGTCTCTATCCA | 91 | 435 |
| 1043507 | 4401 | 4420 | 18153 | 18172 | GCCCTACATCCAAGTACTGA | 114 | 436 |
| 1043513 | 4433 | 4452 | 18185 | 18204 | TGGTCAATCTACCCACCACT | 80 | 437 |
| 1043519 | 4448 | 4467 | 18200 | 18219 | CTAGACCTTAATTCCTGGTC | 119 | 438 |
| 1043525 | 4474 | 4493 | 18226 | 18245 | GAGTCAAGTCTCACATGGGC | 91 | 439 |
| 1043531 | N/A | N/A | 3578 | 3597 | GTTGCCTTGCCTTTCGGCCT | 125 | 440 |

TABLE 6-continued

Reduction of FUS RNA by 5-10-5 MOE gapmers with mixed PO/PS linkages complementary to human FUS RNA

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FUS (% UTC) | SEQ ID NO |
|---|---|---|---|---|---|---|---|
| 1043537 | N/A | N/A | 3858 | 3877 | GTGGTACGGCCTGAGTGCCC | 104 | 441 |
| 1043543 | N/A | N/A | 3899 | 3918 | AGGACTAGCCCACGATCTAT | 120 | 442 |
| 1043549 | N/A | N/A | 4098 | 4117 | GCTTAAGTACGCTCCGCCGC | 89 | 443 |
| 1043555 | N/A | N/A | 4224 | 4243 | TCGCGCCCTTACCTACCGTT | 103* | 444 |
| 1043561 | N/A | N/A | 4234 | 4253 | CGCCGTCGCCTCGCGCCCTT | 104 | 445 |
| 1043567 | N/A | N/A | 4415 | 4434 | ACTTCCCGCCCCGCGCGCGA | 118 | 446 |
| 1043573 | N/A | N/A | 4752 | 4771 | GCGATCCCGCCCATTCGCGA | 98 | 447 |
| 1043579 | N/A | N/A | 4814 | 4833 | AGAGGGCGGCCCCGATCCCG | 127 | 448 |
| 1043585 | N/A | N/A | 4857 | 4876 | TCCGTTGGTCGAACCCTGAC | 90 | 449 |
| 1043591 | N/A | N/A | 5236 | 5255 | GCCGTTCTTCTCCGTCCCTA | 87 | 450 |
| 1043597 | N/A | N/A | 5481 | 5500 | GCAACTGCTCGCCTTAGGAG | 30 | 451 |
| 1043603 | N/A | N/A | 5774 | 5793 | TGATTGCTCTAAAACATCGC | 100 | 452 |
| 1043609 | N/A | N/A | 7635 | 7654 | GTTCCAATTTCACCCCGCCA | 29 | 453 |
| 1043615 | N/A | N/A | 7857 | 7876 | GACTGAGTTCCATAGCCTGC | 67 | 454 |
| 1043621 | N/A | N/A | 7994 | 8013 | CACCACCGTACCTTCCCGAG | 80 | 455 |
| 1043627 | N/A | N/A | 8096 | 8115 | AGGCTCCCCTACCCCAATTA | 110 | 456 |
| 1043633 | N/A | N/A | 9506 | 9525 | TCATCGGTTTCCCTTGCAGA | 7 | 457 |
| 1043639 | N/A | N/A | 9710 | 9729 | TCAGCTGGCCCCATAAACCA | 51 | 458 |
| 1043645 | N/A | N/A | 10218 | 10237 | CACCCCTTCTACACTGCGAG | 49 | 459 |
| 1043651 | N/A | N/A | 10432 | 10451 | AACCCTACCCCAATTTACCC | 82 | 460 |
| 1043657 | N/A | N/A | 10969 | 10988 | ACAGGTGGCATTCTACCCTA | 72 | 461 |
| 1043663 | N/A | N/A | 11069 | 11088 | GCCTACTAGACCCCTCTTAT | 41 | 462 |
| 1043669 | N/A | N/A | 11286 | 11305 | GTATACCAACTTCACCATCC | 10 | 463 |
| 1043675 | N/A | N/A | 11466 | 11485 | GTCCACGAATTCAGTTTGTG | 21 | 464 |
| 1043681 | N/A | N/A | 11669 | 11688 | TGTTTATCTGAATTCGCCAT | 7 | 465 |
| 1043687 | N/A | N/A | 11928 | 11947 | CTCGCCACCAGCCATGCGAT | 95 | 466 |
| 1043693 | N/A | N/A | 12115 | 12134 | GCAGGCCCCTTAAGATCTGT | 105 | 467 |
| 1043699 | N/A | N/A | 12390 | 12409 | AGTCTTGATACCACTTTAGC | 49 | 468 |
| 1043705 | N/A | N/A | 13327 | 13346 | GCAACAACCACTAAGACTTG | 91 | 469 |
| 1043711 | N/A | N/A | 13841 | 13860 | GCTTGTTTCCTAAGGCTTGC | 103 | 470 |
| 1043717 | N/A | N/A | 14391 | 14410 | AGTTTCACTCACGGATTAGG | 101 | 471 |
| 1043723 | N/A | N/A | 14886 | 14905 | CCCCGCTGAAAAATTAAGGA | 136 | 472 |
| 1043729 | N/A | N/A | 15153 | 15172 | CCCTGTTATCCTATGGCCTC | 103 | 473 |
| 1043735 | N/A | N/A | 15298 | 15317 | TCCTACCTAACCCAGCGAGT | 101 | 474 |
| 1043741 | N/A | N/A | 15324 | 15343 | CCAAGCCTAGATATCCTATC | 80 | 475 |

Example 2: Effects of Modified Oligonucleotides on Human FUS mRNA In Vitro, Multiple Doses Modified oligonucleotides selected from the examples above were tested at various doses in A-431 cells. Cultured A-431 cells at a density of 10,000 cells per well were treated using free uptake with 185 nM, 556 nM, 1667 nM, and 5000 nM of modified oligonucleotide as specified in the Table 3 below. After a treatment period of approximately 48 hours, total RNA was isolated from the cells and FUS RNA levels were measured by quantitative real-time PCR. Human FUS primer probe set RTS38562 was used to measure RNA levels as described above. FUS levels were adjusted according to total RNA content, as measured by RIBOGREENK® Results are presented in Tables 7-9 below as percent reduction of the amount of FUS RNA, relative to untreated control. The half maximal inhibitory concentration ($IC_{50}$) was calculated using a linear regression on a log/linear plot of the data in excel.

TABLE 7

Dose-dependent percent reduction of human FUS RNA by 5-10-5 MOE gapmers with mixed PO/PS linkages complementary to human FUS

| Compound | % UTC | | | | $IC_{50}$ |
|---|---|---|---|---|---|
| No. | 185 nM | 556 nM | 1667 nM | 5000 nM | (μM) |
| 1043279 | 96 | 75 | 56 | 42 | 2.8 |
| 1043327 | 85 | 67 | 52 | N.D. | N.C. |
| 1043334 | 87 | 81 | 63 | 47 | 4.6 |
| 1043352 | 95 | 76 | 56 | 46 | 3.2 |
| 1043397 | 64 | 26 | 11 | 5 | 0.3 |
| 1043400 | 92 | 72 | 52 | 45 | 2.7 |
| 1043401 | 36 | 22 | 17 | 12 | <0.2 |
| 1043610 | 75 | 73 | 50 | 40 | 2.2 |
| 1043634 | 48 | 19 | 11 | 8 | <0.2 |
| 1043640 | 80 | 61 | 37 | 24 | 1.0 |
| 1043641 | 61 | 23 | 11 | 6 | 0.2 |
| 1043646 | 96 | 55 | 31 | 19 | 1.0 |
| 1043647 | 77 | 51 | 30 | 18 | 0.7 |
| 1043653 | 52 | 29 | 13 | 7 | <0.2 |
| 1043670 | 82 | 62 | 43 | 28 | 1.2 |
| 1043671 | 76 | 59 | 36 | 19 | 0.8 |
| 1043683 | 64 | 28 | 12 | 8 | 0.3 |
| 1043684 | 58 | 26 | 10 | 6 | 0.2 |
| 1043719 | 79 | 71 | 62 | 49 | >5.0 |

TABLE 8

Dose-dependent percent reduction of human FUS RNA by 5-10-5 MOE gapmers with mixed PO/PS linkages complementary to human FUS

| Compound | % UTC | | | | $IC_{50}$ |
|---|---|---|---|---|---|
| No. | 185 nM | 556 nM | 1667 nM | 5000 nM | (μM) |
| 1043323 | 119 | 95 | 97 | 76 | >5.0 |
| 1043341 | 70 | 65 | 45 | 32 | 1.2 |
| 1043390 | 55 | 16 | 7 | 4 | <0.2 |
| 1043395 | 81 | 47 | 20 | 9 | 0.6 |
| 1043396 | 96 | 59 | 39 | 22 | 1.2 |
| 1043397 | 63 | 28 | 9 | 4 | 0.3 |
| 1043445 | 88 | 67 | 37 | 21 | 1.1 |
| 1043462 | 98 | 109 | 111 | 108 | >5.0 |
| 1043613 | 55 | 33 | 15 | 7 | 0.2 |
| 1043636 | 61 | 40 | 17 | 11 | 0.3 |
| 1043637 | 57 | 24 | 8 | 3 | <0.2 |
| 1043642 | 82 | 60 | 46 | 30 | 1.3 |
| 1043643 | 29 | 8 | 4 | 2 | <0.2 |
| 1043655 | 71 | 43 | 16 | 8 | 0.4 |
| 1043661 | 61 | 39 | 30 | 17 | 0.3 |

TABLE 8-continued

Dose-dependent percent reduction of human FUS RNA by 5-10-5 MOE gapmers with mixed PO/PS linkages complementary to human FUS

| Compound | % UTC | | | | $IC_{50}$ |
|---|---|---|---|---|---|
| No. | 185 nM | 556 nM | 1667 nM | 5000 nM | (μM) |
| 1043672 | 62 | 44 | 28 | 21 | 0.4 |
| 1043673 | 67 | 46 | 34 | 23 | 0.5 |
| 1043678 | 83 | 58 | 36 | 29 | 1.1 |
| 1043685 | 82 | 38 | 13 | 5 | 0.5 |

TABLE 9

Dose-dependent percent reduction of human FUS RNA by 5-10-5 MOE gapmers with mixed PO/PS linkages complementary to human FUS

| Compound | % UTC | | | | $IC_{50}$ |
|---|---|---|---|---|---|
| No. | 185 nM | 556 nM | 1667 nM | 5000 nM | (μM) |
| 1043320 | 106 | 90 | 58 | 48 | 3.8 |
| 1043391 | 70 | 25 | 7 | 5 | 0.3 |
| 1043397 | 68 | 28 | 11 | 5 | 0.3 |
| 1043398 | 42 | 15 | 9 | 4 | <0.2 |
| 1043399 | 34 | 13 | 5 | 3 | <0.2 |
| 1043608 | 97 | 72 | 51 | 39 | 2.2 |
| 1043609 | 83 | 62 | 38 | 25 | 1.1 |
| 1043633 | 54 | 21 | 8 | 6 | <0.2 |
| 1043644 | 67 | 19 | 4 | 2 | 0.2 |
| 1043649 | 84 | 59 | 40 | 26 | 1.1 |
| 1043650 | 73 | 32 | 18 | 12 | 0.4 |
| 1043662 | 89 | 58 | 47 | 28 | 1.3 |
| 1043669 | 65 | 38 | 22 | 10 | 0.4 |
| 1043674 | 59 | 39 | 22 | 14 | 0.3 |
| 1043675 | 89 | 67 | 46 | 29 | 1.5 |
| 1043680 | 46 | 17 | 6 | 3 | <0.2 |
| 1043681 | 69 | 39 | 18 | 8 | 0.4 |
| 1043698 | 95 | 85 | 59 | 35 | 2.6 |
| 1043728 | 99 | 84 | 64 | 51 | >5.0 |

Example 3: Design of Modified Oligonucleotides Complementary to a Human FUS Nucleic Acid Additional modified oligonucleotides were designed as indicated in Table 10 below.

The modified oligonucleotides Table 10 below are 5-10-5 MOE gapmers. The gapmers are 20 nucleosides in length, wherein the central gap segment consists of ten 2'-β-D-deoxynucleosides, the 5' wing segment consists of five 2'-MOE nucleosides, and the 3' wing segment consists of five 2'-MOE nucleosides. The sugar motif of the gapmers is (from 5' to 3'): eeeeeddddddddddeeeee; wherein ‘d’ represents a 2'-β-D-deoxyribosyl sugar moiety, and ‘e’ represents a 2'-MOE sugar moiety. The gapmers have an internucleoside linkage motif of (from 5' to 3'): sooosssssssssssooss; wherein “s” represents a phosphorothioate internucleoside linkage and “o” represents a phosphodiester internucleoside linkage. All cytosine residues are 5-methylcytosines.

“Start site” indicates the 5'-most nucleoside to which the modified oligonucleotide is complementary in the human gene sequence. “Stop site” indicates the 3'-most nucleoside to which the modified oligonucleotide is complementary in the human gene sequence. Each modified oligonucleotide listed in Table 10 is 100% complementary to SEQ ID NO: 2 (GENBANK Accession No. NC_000016.10 truncated from nucleotides 31176001 to 31198000). ‘N/A’ indicates that the modified oligonucleotide is not 100% complementary to that particular gene sequence.

TABLE 10

| 5-10-5 MOE gapmers with a mixed PO/PS internucleoside linkages complementary to human FUS | | | | | | |
|---|---|---|---|---|---|---|
| Compound Number | SEQUENCE | SEQ ID No: 1 Start Site | SEQ ID No: 1 Stop Site | SEQ ID No: 2 Start Site | SEQ ID No: 2 Stop Site | SEQ ID No. |
| 1044028 | GGCACATAAAATGCAGAGCA | N/A | N/A | 10159 | 10178 | 476 |
| 1044030 | GCAATGTCACCTTTCATACC | N/A | N/A | 10182 | 10201 | 13 |
| 1044031 | GAGTATTTTGCAATGTCACC | N/A | N/A | 10191 | 10210 | 477 |
| 1044032 | GGAGTATTTTGCAATGTCAC | N/A | N/A | 10192 | 10211 | 478 |
| 1044033 | GCGGAGTATTTTGCAATGTC | N/A | N/A | 10194 | 10213 | 479 |
| 1044075 | GTGCATCCATCCAGTTTCTC | N/A | N/A | 11908 | 11927 | 480 |

Example 4: Effects of Modified Oligonucleotides on Human FUS mRNA In Vitro, Multiple Doses Modified oligonucleotides selected from the examples above were tested at various doses in A-431 cells. Cultured A-431 cells at a density of 10,000 cells per well were treated using free uptake with various concentrations of modified oligonucleotide as specified in the Table 11 below. After a treatment period of approximately 48 hours, total RNA was isolated from the cells and FUS RNA levels were measured by quantitative real-time RTPCR. Human FUS primer probe set RTS38562 was used to measure RNA levels as described above. FUS levels were adjusted according to total RNA content, as measured by RIBOGREEN®. Results are presented in the Table 11 below as percent reduction of the amount of FUS RNA, relative to untreated control. The half maximal inhibitory concentrations ($IC_{50}$) were calculated using a linear regression on a log/linear plot of the data in excel.

TABLE 11

| Dose-dependent percent reduction of human FUS RNA by 5-10-5 MOE gapmers with mixed PO/PS linkages complementary to human FUS | | | | | | | |
|---|---|---|---|---|---|---|---|
| | % UTC | | | | | | |
| Compound No. | 5 nM | 20 nM | 78 nM | 313 nM | 1250 nM | 5000 nM | $IC_{50}$ (μM) |
| 1043643 | 87 | 75 | 56 | 29 | 18 | 12 | 0.1 |
| 1043644 | 77 | 73 | 57 | 38 | 19 | 9 | 0.1 |
| 1043678 | 118 | 133 | 105 | 95 | 76 | 53 | >5.0 |
| 1044028 | 78 | 76 | 71 | 56 | 39 | 35 | 0.6 |
| 1044030 | 70 | 73 | 48 | 31 | 16 | 9 | 0.1 |
| 1044031 | 75 | 82 | 58 | 42 | 26 | 17 | 0.2 |
| 1044032 | 95 | 92 | 92 | 56 | 35 | 18 | 0.5 |
| 1044033 | 118 | 105 | 102 | 83 | 54 | 40 | 2.8 |
| 1044075 | 108 | 95 | 80 | 59 | 40 | 29 | 0.7 |

Example 5: Tolerability of Modified Oligonucleotides in Wild-Type Mice

Modified oligonucleotides described above were tested in wild-type female C57/B16 mice to assess the tolerability of the oligonucleotides. Additionally, Comparator Compound No. 441522 was tested in wild-type female C57/B16 mice to assess the tolerability of the oligonucleotides. Wild-type female C57/B16 mice each received a single ICV dose of 700 μg or 500 μg of modified oligonucleotide in separate experiments as listed in Tables 12-15 below. Each treatment group consisted of 4 mice. A group of 4 mice received PBS as a negative control for each experiment (identified in separate tables below). At 3 hours post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse and averaged within each treatment group.

TABLE 12

Tolerability scores in mice at 700 μg dose

| Compound Number | 3 hour FOB |
|---|---|
| PBS | 0.00 |
| 1043341 | 1.00 |
| 1043390 | 3.00 |
| 1043391 | 5.75 |
| 1043397 | 2.00 |
| 1043398 | 4.50 |
| 1043399 | 4.00 |
| 1043401 | 4.75 |
| 1043613 | 1.00 |
| 1043633 | 2.25 |
| 1043634 | 5.50 |
| 1043636 | 2.50 |
| 1043637 | 1.00 |
| 1043641 | 1.00 |
| 1043650 | 1.00 |
| 1043653 | 5.00 |
| 1043655 | 1.00 |
| 1043661 | 4.00 |
| 1043669 | 1.00 |
| 1043672 | 0.00 |
| 1043674 | 4.00 |
| 1043680 | 5.25 |
| 1043681 | 3.00 |
| 1043683 | 1.00 |
| 1043684 | 1.00 |

TABLE 13

Tolerability scores in mice at 500 μg dose

| Compound Number | 3 hour FOB |
|---|---|
| PBS | 0.00 |
| 1043678 | 1.00 |
| 1044022 | 0.00 |
| 1044023 | 0.00 |
| 1044024 | 2.00 |
| 1044025 | 0.00 |
| 1044030 | 0.00 |
| 1044049 | 1.00 |
| 1044053 | 0.00 |

TABLE 14

Tolerability scores in mice at 700 μg dose

| Compound Number | 3 hour FOB |
|---|---|
| PBS | 0.00 |
| 441522 | 6.00 |

TABLE 15

Tolerability scores in mice at 700 μg dose

| Compound Number | 3 hour FOB |
|---|---|
| PBS | 0.00 |
| 1044030 | 0.00 |

Example 6: Activity of Modified Oligonucleotides Complementary to Human FUS in Transgenic Mice Transgenic mice lines (mice expressing the human FUS wildtype gene hgFUS$^{WT}$, or mice containing human FUS mutations R521C or R521H, hgFUS$^{R521C}$ and hgFUS$^{R521H}$), previously described in Lopez-Erauskin., et al., *ALS/FTD-Linked Mutation in FUS Suppresses Intra-axonal Protein Synthesis and Drives Disease Without Nuclear Loss-of-Function of FUS*, Neuron 2018, 100:816-830, were used to test activity of modified oligonucleotides described above. The FUS transgenic mice were divided into groups of 3 mice each. Each mouse received a single ICV bolus of 500 g of modified oligonucleotide. A group of 4 mice received PBS as a negative control.

Four weeks post treatment, mice were sacrificed, and RNA was extracted from cortical brain tissue and spinal cord for real-time qPCR analysis of RNA expression of FUS using primer probe set RTS38562 as described above. Results are presented as percent change of RNA, relative to PBS control, normalized to mouse GAPDH. Mouse GAPDH was amplified using primer probe set RTS108 (forward sequence GGCAAATTCAACGGCACAGT, designated herein as SEQ ID NO: 9; reverse sequence GGGTCTCGCTCCTGGAAGAT, designated herein as SEQ ID NO: 10; probe sequence AAGGCCGAGAATGG-GAAGCTTGTCATC, designated herein as SEQ ID NO: 11). Two separate experiments were carried out under similar conditions. The results for each experiment are presented in Tables 16 and 17 below.

TABLE 16

| Reduction of human FUS RNA in transgenic mice | | | |
|---|---|---|---|
| Mouse | Compound | FUS RNA (% control) | |
| Line | ID | SPINAL CORD | CORTEX |
| WT | PBS | 100 | 100 |
| | 1043341 | 55 | 78 |
| | 1043390 | 62 | 81 |
| | 1043398 | 57 | 89 |
| | 1043399 | 64 | 94 |
| | 1043613 | 44 | 60 |
| | 1043636 | 60 | 106 |
| R521H | PBS | 100 | 100 |
| | 1043397 | 42 | 56 |
| | 1043637 | 33 | 103 |
| | 1043672 | 32 | 78 |
| | 1043674 | 49 | 88 |
| | 1043680 | 14 | 19 |
| | 1043681 | 35 | 52 |

TABLE 17

| Reduction of human FUS RNA in transgenic mice | | | |
|---|---|---|---|
| Mouse | Compound | FUS RNA (% control) | |
| Line | ID | SPINAL CORD | CORTEX |
| R521H | PBS | 100 | 100 |
| | 1043643 | 51 | 96 |
| | 1043678 | 48 | 112 |
| | 1044028 | 83 | 159 |
| | 1044030 | 23 | 57 |
| | 1044033 | 59 | 84 |
| | 1043644 | 67 | 133 |
| R521C | PBS | 100 | 100 |
| | 1044032 | 48 | 96 |
| WT | PBS | 100 | 100 |
| | 1044031 | 28 | 66 |

Example 7: Tolerability of Modified Oligonucleotides in Rats, 3 mg Dose

Modified oligonucleotides described above were tested in rats to assess the tolerability of the oligonucleotides. Sprague Dawley rats each received a single intrathecal (IT) dose of 3 mg of oligonucleotide listed in Table 9 below. Each treatment group consisted of 3-4 rats. A group of 3-4 rats received PBS as a negative control. At 3 hours post-injection, movement in 7 different parts of the body were evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; (7) the rat's head. For each of the 7 different body parts, each rat was given a sub-score of 0 if the body part was moving or 1 if the body part was paralyzed. After each of the 7 body parts were evaluated, the sub-scores were summed for each rat and then averaged for each group (the functional observational battery score or FOB). For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Results are presented in Table 18 as the average score for each treatment group. All compounds listed in Table 18 were found to be more tolerable in rats as compared to Comparator Compound No. 441522.

TABLE 18

| Tolerability scores in rats at 3 mg dose | |
|---|---|
| Compound Number | 3 hour FOB |
| PBS | 0.00 |
| 1043613 | 1.00 |
| 1043680 | 2.33 |
| 1044030 | 0.67 |

Example 8. Human Clinical Trial with Compound No. 1044030

Patients displaying one or more symptoms of ALS and/or identified as having a gain of function mutation in FUS are administered Compound No. 1044030 intrathecally. Symptomatic, pre-symptomatic, and prodromal patients receive 50 mg to 200 mg of Compound No. 1044030 about every 4 weeks, about every 8 weeks, or about every 12 weeks.

Pharmacodynamics and efficacy are assessed at multiple time points. Efficacy of Compound No. 1044030 is assessed by monitoring function in daily activities, muscle strength and respiratory function. In some instance, the assessment takes the form of a questionnaire, patient-reported outcome, or ALS Functional Rating Scale. Patient safety is monitored closely during the study. Safety and tolerability evaluations may include, e.g., physical examination, vital signs, adverse events, concomitant medications, and plasma laboratory tests.

What is claimed is:

1. A modified oligonucleotide according to the following chemical structure:

(SEQ ID NO. 13)

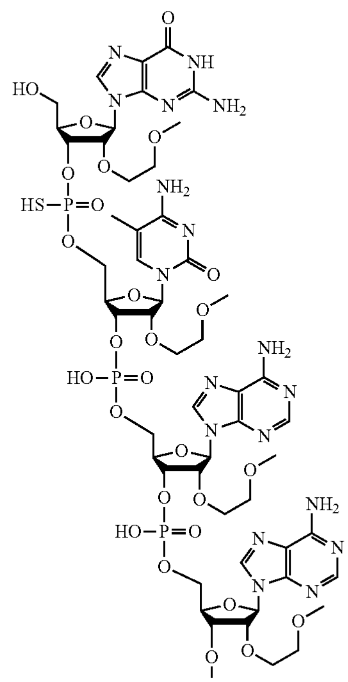

-continued

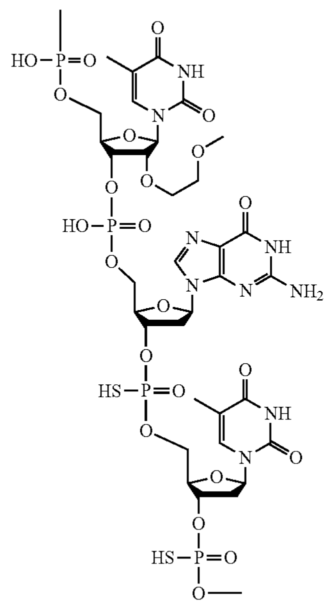

-continued
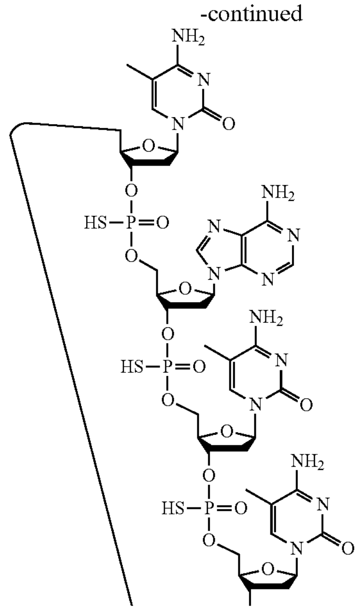
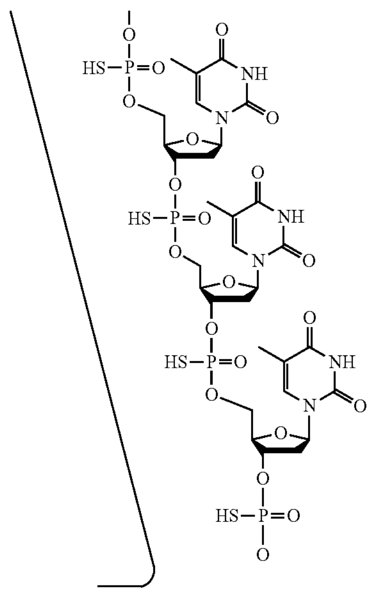
-continued
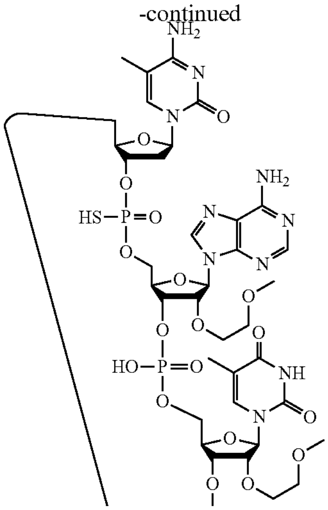
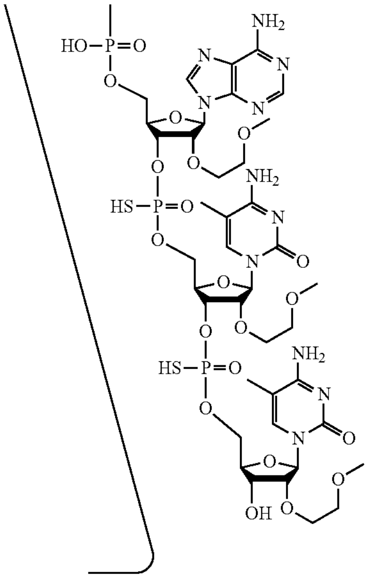
or a salt thereof.
2. A sodium salt or a potassium salt of the modified oligonucleotide of claim 1.

3. A modified oligonucleotide according to the following chemical structure:

(SEQ ID NO: 13)

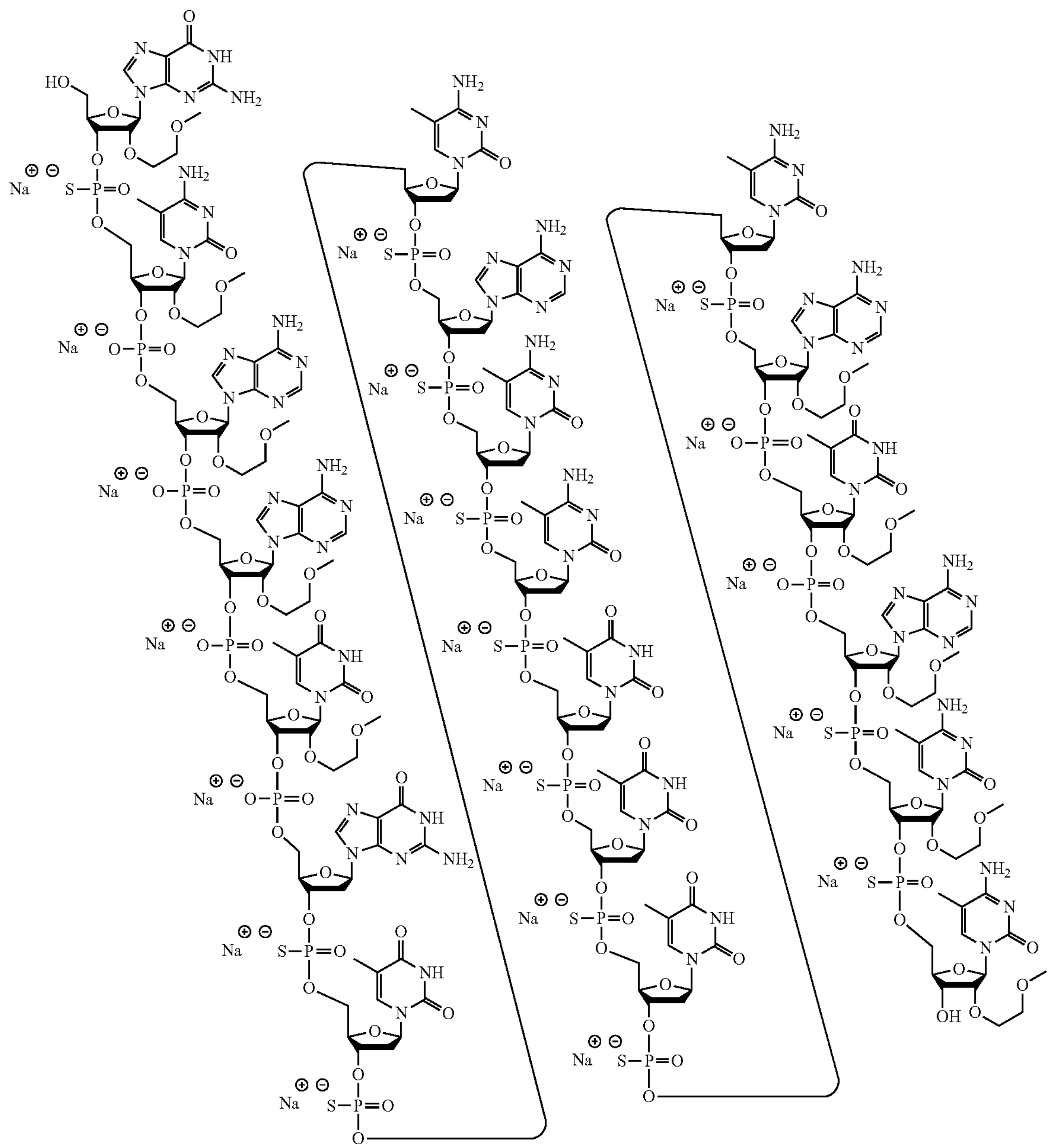

4. An oligomeric compound comprising a modified oligonucleotide according to the following formula:

Ges Ceo Aeo Aeo Teo Gds Tds $^{m}$Cds Ads $^{m}$Cds $^{m}$Cds Tds Tds Tds $^{m}$Cds Aeo Teo Aes $^{m}$Ces $^{m}$Ce (SEQ ID NO: 13); wherein, A=an adenine, $^{m}$c=a 5-methyl cytosine G=a guanine, T=a thymine, e=a 2'-O-methoxyethylribose modified sugar d=a 2'-deoxyribose sugar, s=a phosphorothioate internucleoside linkage, and o=a phosphodiester internucleoside linkage.

5. A population of modified oligonucleotides of claim 1, wherein all phosphorothioate internucleoside linkages of the modified oligonucleotide are stereorandom.

6. A population of modified oligonucleotides of claim 3, wherein all phosphorothioate internucleoside linkages of the modified oligonucleotide are stereorandom.

7. A population of oligomeric compounds of claim 4, wherein all phosphorothioate internucleoside linkages of the modified oligonucleotide are stereorandom.

8. A pharmaceutical composition comprising the modified oligonucleotide of claim 1 and a pharmaceutically acceptable diluent.

9. The pharmaceutical composition of claim 8, wherein the pharmaceutically acceptable diluent is artificial cerebrospinal fluid (aCSF) or phosphate buffered saline (PBS).

10. The pharmaceutical composition of claim 9, wherein the pharmaceutical composition consists essentially of the modified oligonucleotide and aCSF.

11. A pharmaceutical composition comprising the modified oligonucleotide of claim 3 and a pharmaceutically acceptable diluent.

12. The pharmaceutical composition of claim 11, wherein the pharmaceutically acceptable diluent is artificial cerebrospinal fluid (aCSF) or phosphate buffered saline (PBS).

13. The pharmaceutical composition of claim 12, wherein the pharmaceutical composition consists essentially of the modified oligonucleotide and aCSF.

14. A pharmaceutical composition comprising the oligomeric compound of claim 4 and a pharmaceutically acceptable diluent.

15. The pharmaceutical composition of claim 14, wherein the pharmaceutically acceptable diluent is artificial cerebrospinal fluid (aCSF) or phosphate buffered saline (PBS).

16. The pharmaceutical composition of claim 15, wherein the pharmaceutical composition consists essentially of the oligomeric compound and aCSF.

17. A pharmaceutical composition comprising the population of modified oligonucleotides of claim 5 and a pharmaceutically acceptable diluent.

18. The pharmaceutical composition of claim 17, wherein the pharmaceutically acceptable diluent is artificial cerebrospinal fluid (aCSF) or phosphate buffered saline (PBS).

19. The pharmaceutical composition of claim 18, wherein the pharmaceutical composition consists essentially of the population of modified oligonucleotides and aCSF.

20. A pharmaceutical composition comprising the population of modified oligonucleotides of claim 6 and a pharmaceutically acceptable diluent.

21. The pharmaceutical composition of claim 20, wherein the pharmaceutically acceptable diluent is artificial cerebrospinal fluid (aCSF) or phosphate buffered saline (PBS).

22. The pharmaceutical composition of claim 21, wherein the pharmaceutical composition consists essentially of the population of modified oligonucleotides and aCSF.

23. A pharmaceutical composition comprising the population of oligomeric compounds of claim 7 and a pharmaceutically acceptable diluent.

24. The pharmaceutical composition of claim 23, wherein the pharmaceutically acceptable diluent is artificial cerebrospinal fluid (aCSF) or phosphate buffered saline (PBS).

25. The pharmaceutical composition of claim 24, wherein the pharmaceutical composition consists essentially of the population of oligomeric compounds and aCSF.

* * * * *

SEQUENCE LISTING

```
<160> NUMBER OF SEQ ID NOS: 481

<210> SEQ ID NO 1
<211> LENGTH: 5119
<212> TYPE: DNA
<213> ORGANISM: Homo sapiens

<400> SEQUENCE: 1

acttaagctt cgacgcagga ggcggggctg ctcagtcctc caggcgtcgg tactcagcgg      60

tgttggaact tcgttgcttg cttgcctgtg cgcgcgtgcg cggacatggc ctcaaacgat     120

tatacccaac aagcaaccca aagctatggg gcctacccca cccagcccgg gcagggctat     180

tcccagcaga gcagtcagcc ctacggacag cagagttaca gtggttatag ccagtccacg     240
```

```
gacacttcag gctatggcca gagcagctat tcttcttatg gccagagcca gaacacaggc    300
tatggaactc agtcaactcc ccagggatat ggctcgactg gcggctatgg cagtagccag    360
agctcccaat cgtcttacgg gcagcagtcc tcctaccctg gctatggcca gcagccagct    420
cccagcagca cctcgggaag ttacggtagc agttctcaga gcagcagcta tgggcagccc    480
cagagtggga gctacagcca gcagcctagc tatggtggac agcagcaaag ctatggacag    540
cagcaaagct ataatccccc tcagggctat ggacagcaga accagtacaa cagcagcagt    600
ggtggtggag gtggaggtgg aggtggaggt aactatggcc aagatcaatc ctccatgagt    660
agtggtggtg gcagtggtgg cggttatggc aatcaagacc agagtggtgg aggtggcagc    720
ggtggctatg gacagcagga ccgtggaggc cgcggcaggg gtggcagtgg tggcggcggc    780
ggcggcggcg gtggtggtta caaccgcagc agtggtggct atgaacccag aggtcgtgga    840
ggtggccgtg gaggcagagg tggcatgggc ggaagtgacc gtggtggctt caataaattt    900
ggtggccctc gggaccaagg atcacgtcat gactccgaac aggataattc agacaacaac    960
accatctttg tgcaaggcct gggtgagaat gttacaattg agtctgtggc tgattacttc   1020
aagcagattg gtattattaa gacaaacaag aaaacgggac agcccatgat taatttgtac   1080
acagacaggg aaactggcaa gctgaaggga gaggcaacgg tctcttttga tgacccacct   1140
tcagctaaag cagctattga ctggtttgat ggtaaagaat tctccggaaa tcctatcaag   1200
gtctcatttg ctactcgccg ggcagacttt aatcggggtg gtggcaatgg tcgtggaggc   1260
cgagggcgag gaggacccat gggccgtgga ggctatggag gtggtggcag tggtggtggt   1320
ggccgaggag gatttcccag tggaggtggt ggcggtggag gacagcagcg agctggtgac   1380
tggaagtgtc ctaatcccac ctgtgagaat atgaacttct cttggaggaa tgaatgcaac   1440
cagtgtaagg cccctaaacc agatggccca ggagggggac caggtggctc tcacatgggg   1500
ggtaactacg gggatgatcg tcgtggtggc agaggaggct atgatcgagg cggctaccgg   1560
ggccgcggcg gggaccgtgg aggcttccga gggggccggg gtggtgggga cagaggtggc   1620
tttggccctg gcaagatgga ttccaggggt gagcacagac aggatcgcag ggagaggccg   1680
tattaattag cctggctccc caggttctgg aacagctttt tgtcctgtac ccagtgttac   1740
cctcgttatt ttgtaacctt ccaattcctg atcacccaag ggtttttttg tgtcggacta   1800
tgtaattgta actataccte tggttcccat taaaagtgac cattttagtt aaattttgtt   1860
cctcttcccc cttttcactt tcctggaaga tcgatgtccc gatcaggaag gtagagagtt   1920
ttcctgttca gattaccctg cccagcagga actggaatac agtgttcggg gagaaggcca   1980
aatgatatcc ttgagagcag agattaaact tttctgtcat ggggaaagtt ggtgtataaa   2040
tgagaaatga agaacatggg atgtcatgag tgttggccta aatttgccca gctatgggga   2100
atttttcctt taccacattt atttgcatac tggtcttagt ttatttgcag cagtttatcc   2160
ctttttaaga actctttgat cttttggccc ttttaatggt gaggctcaaa caaactacat   2220
ttaaatgggg cagtattcag atttgaccat ggtggagagc gcttagccac tctgggtctt   2280
tcacaggaag gagagtaact gagtgctgca ggagtttgtg gagtggagtc aggatctagg   2340
aggtgagtga ctcccttcct agctgccctg gtgaacagcg cttgggtaga tacctgctat   2400
aaggagactg gtctggctgg gttactttca catcctgcct gtactcagag ggcttgaggt   2460
cattgacatt atgagatttt aggcttgatc cctttttgat tggagggtgg aaggccctcc   2520
taagggaatg ataagtgata agagggggaa ggggttgcag ccaatgagtt aaaaccttag   2580
agcagtgctc ctcagcctct taccatgtgg ttgtaaactt gcacgtacct gccaaccagt   2640
```

```
tatttagcat gctttttatt ttagttacac agagcgtaac attaacccaa gagcagaaag   2700
gttttattta cagggttttc gaacttggtt tgtaagacag ctgccatcac aagcatagct   2760
tacaaatgtg ctggggaccc ctaattggga agtgctttcc tctcaaattt ttattttta    2820
tttttagaga cagagtcttg ctctgtcatc caggctggag tgcagtggcg tgatctcggc   2880
tcactgtagc ctctgcctcc tgagtttaag cgattctcct gcctcaggag aatcccagct   2940
tctgagtagc tgagactaca ggcgtgggcc accatgccca cctagttttt gcatttttag   3000
tggaggtgtg gtttcactgt gttggccagg ctggtctctt aactcctgac ctcaggtgat   3060
ccacctgcct tggcctccca aagtgctgga attacaggca tgagccgctg catctggcca   3120
tcctctcaaa ttttcaagtg ttccacaagt atgttctcta ctgaagagtt gctgcatcct   3180
tgaatcttgg gtgatttgag gcacagaaac tatgacttta ttttttgaga tggagttttg   3240
ctcttgttgc ccaggctgga gtgcaatggc acgtttttcg gcttaccgca actgccgcct   3300
cctgggttca agcgatagct gggattacag gcatgcgcca ccatgcccag ctaatttatt   3360
tgtattttta gtagagacgg ggtttctcca tgttggtcag gctggtctcg aactcccgac   3420
ctcaggtgat gtgcacacct cagcctccca ataaaccatg acttttaaga ggaatagcag   3480
gtttacttcc cctgccagca ttggggtgct ctctaagcaa cagtaggcgg agagtggtct   3540
ggcgtattaa aaacaaagga tcgtcaagtg ggccttccca ggcattgctt tgacttagta   3600
catgtagagg atgtggcagt tctctccgtc cctgccactg ctggtttctt tgttaaatgt   3660
ttagttgaaa tggcctgata cgatatttga gtagttcact gttggtgctt tgcctagcag   3720
gattctaatc ttgctttggt tgtggtcccc tgatgccctc ctgttaggag tggaggaggt   3780
cgaagctcct tgtaagatat gattactggg accattagtg tcaagttcct gtgtccttca   3840
aatggcatat gtgattggcc ttgaccttaa aaggaaatag ggtcccaggt gactgtttag   3900
tgggtaggtc cagtttgggg ggatcttcca ggagaatgga tagagacacc tagcagcaga   3960
gagaacattg gtgcctctca agccaacctc ccacctcagc ctcccaagta gctgggacta   4020
caggtgcttc ctcgctacca cacctgggta attttttttt taattacttt ttttttttta   4080
agaaacaggg tttcactggg ttgcccaggc tggtcttgaa ctggcctcaa gtgacctgcc   4140
tgcctcagcc tcccaaagtg ctgggatcac aggtgtgacc cactgcgttt ggccagaata   4200
ctctattctt actgaatgat tgaaatctgt cttgaagcat taggtgtccc atttttgtga   4260
gttggaattg ggacaggcta agtaggaagt gaggagggtg gggagagctg tgctgtaggt   4320
ctgtttgtcc cttccttgat gtagccttca gttagccctt tcagcttttt tccccatctt   4380
gtgccgggcc ttcctgggtt tcagtacttg gatgtagggc tgcagttatg tcagtggtgg   4440
gtagattgac caggaattaa ggtctagggt ccagcccatg tgagacttga ctcactgatc   4500
tacctttagg catgtcttcc ttccagtctc atccttttta aatttttttt ttttttttga   4560
gacggtctca ctctcaccca ggctggattg cagtggtgtg atctcgacca actgcaacct   4620
ctgcctccca cccgcaagct atctgcccac ctcagcctct ggagtagctg ggacgggact   4680
acaggcacct gccaccatga ctggctaatt tttttttgta ttttttgtgg agatggggtc   4740
ttgccatgtt gctcaggctg gtctggtctc aaaactgctc tgggctcaag tgattgtccc   4800
actttggcct cccagagtgc tgggattaag gtgtgagata ctgtgtccgg ctatgaaaat   4860
tttattttta attaacttgt atatatttat ggggtacaat gtcctatttc tgtacatgta   4920
cacattgtgg aatcaaatca ggctaatata tccatcactt catatcatta gcatgaatga   4980
```

gaacatacaa agccactctt agaaaatttt gaaatttatg ttatttcagc ccttttatgc 5040
tggaggttgc aaatgttttg tgaataatca gaccaaaaat aaaaacaaaa aatgattgac 5100
ttcagtcatt cagtaagaa 5119

<210> SEQ ID NO 2
<211> LENGTH: 22000
<212> TYPE: DNA
<213> ORGANISM: Homo sapiens

<400> SEQUENCE: 2
ccagcctggg tgacagagtg agactctgtc tcaaaaaaaa atcaatatct gatatacgtg 60
tttatttttt tattgagatg gagtcttgct ctgtcgccca ggctggagtg caatggcaca 120
atctctgctc accgcaacct ctgcctccct ggctcaagca attctcctgc ctcaacctcc 180
cgagtagctg ggactacaga tgcgcgccac catgcccggc caatttctgt atctctagta 240
gagatggggt ttcaccaggt cggtcaggct ggtctcgaac tcctgacctc atgatctgcc 300
cacctcagcc tcccaaagtg ctgggattac aggtgtgagc gaacgcatct ggcccaatat 360
ctgatataca tgttaattga aactgggtgt ggtggtcaca cctttaatca cagcactttg 420
ggaggattcc cttgagccta ggagttcaag accagcctgg gcaacatagc aagaccctgt 480
ctcaaaaaag aaaaatttaa cattgacttt cctgtcagag ataggaagta aataagacat 540
ttatggtgaa cttaaagcac atatggcagc taaaggtgac agtgtctcac tccagctgac 600
ccttgcccta tggaagtggg cctggaatgg cccactattt ttagtgttgg caactagtta 660
aaaaaattaa aacattcgag gcaggtggat cacttgagat caggagttcg agaacagcct 720
gggcaatatg gtgaaacccc gtctctacta aaaataggaa aattagctgg acatggtgat 780
gcatgcctgt aatctcagct actcgggagg ctgcagcaca agaattgctt gaacccggga 840
ggcagaggtt gcagtgagct gagatcacgt cactgcactc cagcctgggt gacagagtga 900
gactccatct caaaaaaaaa aaaaaaagaa agaaagaaat ggccatttga tttagtcttt 960
cagagtcaca tatttttttt tttttgaggc cgagtctcat ctgccaccat gcccagccca 1020
gagtcacagc tggagcctga actctgcctc agtgtcttcc ccacttgtgc ctttgtcttc 1080
gcggttctgc ctattatagc ctttcctccc ttgctgcttg gcaaacttct acttatccag 1140
taagccttgg cttcagggtt accatctctc tttagtgttc tgtggttgtc cacctgatgg 1200
atgacttact ctgctggcag ggtttccagt ctttgattcc atgtgatggc acttactaca 1260
ctcaagtaca ctttgtggtc tgtgtgtctc acccacattc acccactggc tggtcctgtg 1320
gtttaggaac tgagcttttt tttatccata tccatccagt cggccccatg attggaacat 1380
actatgcagt gctcaggcaa tgtttgctga agcgcagggg ttaagagcag gctacctggc 1440
ttgggaaccc agctttgcca cttcctgtgt agcttcagca taactttccg tctttctttt 1500
tttttagaga cagagtcttg ctctactcta tcatccaggc tgcagtgcag tggcgcgatc 1560
tcggctcact gcaacctctg cctccggggt tcaagcaatt ctcctgcctc agcctcctga 1620
gtagctggga ctacaggtgc gcgccactat gcctggctaa tgtttgtatt tttagtagag 1680
acggggtttc accatgttgg tcaggctggt ctcgaactcc tgacgttgtg atctgccctc 1740
cttggcctcc caaagtgctg ggattacagg cgtgagccac cgtgcccggt caactgcctg 1800
tctttctatg cttatttcct catctgtaaa atgtcatcct tagcagggcg tggtggctca 1860
cacctgtaat tccagcaatt tgggaggcca aggcagatgg atcatctgag gccaggagtt 1920
cgagaccagc ctggccaaca tggtgaaacc ccgtctctac taagaataca aacattagct 1980

```
gggtgtggtg gcgcacacct gtactcccag ctacttggga ggttgaagtt gtagaatcac   2040
ttgaacgcgg gaggcacatg ttgcagtgag ccgagacggc gcccctgcac tccagcctgg   2100
gtgacagagt gagacagtgt ccccccaaaa aaaaaaaaga taaaatgtca tcctcacatc   2160
agccttttgt tgtgaaaaat aaaatcaaga gtttactcag tcagaacagg gcctgacagt   2220
aagtcttgtt aaagtgttag ctattacata ttatagatga gcacaatgta tatcattatt   2280
aaatgtcagc tttattatta ttatttgttt tgagacagtc ttgctctgtt gcccaggctg   2340
gagtgcagtg gcacgtcttg gctcactgca acttccgcct cctgggttca agcgattctc   2400
ccatctcagc ttcctgagta gctgggatta cagatgcgcg gacgacgcct ggctaatttt   2460
tgtattttta gtagagacgg ggtttcacca tgttggccag gctggtctcg aactcctgac   2520
ctcgtgatcc acacgcctcg gcctcccaaa gtgctggtat tacaggcgtg agccaccgca   2580
cccggtcagc tttattatta aatgttaact tcatctgctt tgtacacgaa tgcataccca   2640
gtgcccagaa cagtgcctgg aacatactag gtgctaaata aatatttgtg acttaatgca   2700
tgaataaggg tggacttcct ttcttttgct ctcactggag agttgaactc tccttccaaa   2760
ggcggtgggg tggatattgg catattcagg gcctttaggg ctgaagtcaa gggcttagtg   2820
gggcttaatt tgtgggcggg cccagggcat ggccctcatt gtttctctag aaagacgtgt   2880
ccaaccctca aaggaccttc tgaaatcccg ctgaaaggtt aagttgggaa ggaaaacctg   2940
catgcctatg tatcaggaat taacgtcttt tgtcttgttt tattcagtag tttcaaattg   3000
ccttctccag gcaaggctga tgaaagtgca agttgcaagt taatttgaat gtttcttttt   3060
gcttttgctc tcacaggaag tgaaaaggcg accaaacact ctagcattca tgccaccaaa   3120
aagaggagtg ttttgcagtt acaagacctg gattcgaatc acgactcctc ttagctgccc   3180
tgtaatcagg cacaattact tgggtctctg agtctcactt tccttatcta gaaaacggag   3240
gtatctttac ttccttcgta agactgatga caaggaaatt atctgtgcat tttgaaacca   3300
cttaagcctt gtacacgttt tatttctggg atcgccctgg tagggcttca gaaaaataaa   3360
aaggaggtcc ctgagaaaag gctgggtacc gtacatctga ggtcaaccct ctctggtccc   3420
aaggatggcc tgggctgttc cgccccgtgg ctccccaggg gcaaagccat gaggatccgg   3480
gtgagagccc agtgctggac gagcccgggg cccaggggtc ccggccgaaa tccctgctgt   3540
ctttcaggtc aaacgtcata atccccgaac cccagaaagg ccgaaaggca aggcaaccct   3600
gaaagacgac gaagtcaacc tcagggcgca ggagagggag ggccagtgtg ctgccgacga   3660
gggaggctgg agccgcgggg acgaggcgcc ccatacagcg gcaagagggt ggagggcagg   3720
agctcgccat cctgggtgaa agcggggccc agcgaagggg cccggccaca ggaatctcgg   3780
ttccaccccg ctactcccgg ctgtgactcc agtttcgtcc ccagccgccg ggaccgcccc   3840
ctcgccccgc ccccagcggg cactcaggcc gtaccactgt gccttcatgg gggtggagat   3900
agatcgtggg ctagtcctgc cgaggagaga ggggttcttc ctcaaaaaat atgattatgt   3960
atagtattcg catgattcta gttaacttgt ttcccttctg cctgctcgga ccctctacct   4020
gccctacgaa gggggcggag tgcgttcctg cctccccctg ctcttccgcg tttggtgcgc   4080
gcctgcgcgg tgcgtaggcg gcggagcgta cttaagcttc gacgcaggag gcggggctgc   4140
tcagtcctcc aggcgtcggt actcagcggt gttggaactt cgttgcttgc ttgcctgtgc   4200
gcgcgtgcgc ggacatggcc tcaaacggta ggtaagggcg cgaggcgacg gcggcggcgc   4260
acccggccga ggcctcccag ctgggctttt cgttttcagt gggaccgggg cggcgatccc   4320
```

-continued

```
gtgtgggatt ttttggcgcc cctgtggcgg gaagccgcgg agaagagtaa ctggaggagg   4380
ctggtgtcgc cattttgttt cgctcctctg gccctcgcgc gcggggcggg aagtcttttc   4440
tttgcagtcc gtttgcttgg ggtgggcgtt gggagggacg cttcttaggg gtttgaagcg   4500
tcaggtgagg gtggaaaacg cccattctcc gtggcctcgc ctcccccaac tcccggcccc   4560
gcgctcgagc ccgctttgtc gcagtgctgc atccgggcac tcgcggcgcg cacgcgctct   4620
gcgggcccct ccccccttcgc ggcgcgggta ccccttcccc gcctcgtgtt ggttcagctt   4680
tctgtcgcga gacccttcgc ggaagactcg gcggcgcgcg tccggtgtga gccttgtccc   4740
tcagtggtcc ttcgcgaatg ggcgggatcg ctccgttccc gcctgggttg ccacgcggct   4800
gggggcggag gctcgggatc ggggccgccc tctagcttaa cggtttggcg gcggtggtca   4860
gggttcgacc aacggacttg ggacggcccc gagagttttt cccgcctaaa tttctttctt   4920
tttttttttg gagacacggt cttcctctgt cgcccaggct ggagtgcagt ggtgcgatct   4980
cagatcactg caacgtccac ctcctgggtt caagtgattc ttctgcctca gcctcctgag   5040
tagttgggat tataggcgcc cgccaccaca gcccggctaa tttttgtgtt tcttagtagg   5100
ggcggggttt caccatgttg gtcaggctgg tctcgaactg ctgacctcag gtgatccgcc   5160
cgcctgggcc tcccgaagtg tcgggattac agacgtaagc caaccacgcc tggtctaaat   5220
ttcttttttc tgagataggg acggagaaga acggccgccc gaggccacac cctctcctgg   5280
tcctctttcc cttttcctgc gggggaagcg ccgcgtttcc tgtgctggga ggatgagttg   5340
atcttgttcg tgtatcttaa gtggggcttt tcaaaagcgc ttttgttgct ttttgttcgc   5400
tgggggaagg cagggtaggt gagaaaacgg aaccatctgg agtcccaggg ctggggactc   5460
gagtacctgt tgactttcgc ctcctaaggc gagcagttgc atgatctctg tcatttgggg   5520
tccaagggct cttttgattc tctggctttg cactaaaaag cccacttcat ctccgggatt   5580
ggtcaaagag tgaagaatgg cctttttttga gactttctta ttctgtgggt ctgggctgag   5640
agagcagagg ccacaatctg aacactgttc gaattcaaac ctgtgccact ttggtagttc   5700
tgcgacgttg ggagagttag tctcttgact cctggcgata atggctttct catagagtgg   5760
atgaaacgaa tgcgcgatgt tttagagcaa tcactgacat gaattgggct tgcagaaaat   5820
tgtggatgtc caccaagacc ttggtttttc caatggttaa ggcttctggg actctgtaga   5880
aacttgcatt ttcttcactt tttctttatt gtaagaacac ttggctgata acgccagttt   5940
gttcctcttc tcaaccagtg tctcatggag gaattttatg ccctttgttg caacatggtc   6000
ctatttttat tttttttttt gagatggagt cttgctctgt tgccaggctg gagtgcaatg   6060
gctcactgca acctctgcct cccgggttca agcgattctc ctgcttcacc tcccgagtag   6120
ctgggattac aggcgtgcgc caccatgccc ggctaatttt ttgtattttt attagagatg   6180
gggcttcacc atgttggtca ggccagtctc gaattcctga cctcaagtga tccacccacc   6240
tcggcctccc aaactgctgg gattacaggc atgatccacc gtgcctggcc tacgtggtcc   6300
tttttattca tcagtgcttg agttaaggaa tttagcttta attcaactct ttcagagtgg   6360
cagctgaaga taatgtgatt gtatttttct tttgcagatt atacccaaca agcaacccaa   6420
aggtgagtgc tatttttggg cttccagagt ttgtagaggg caagggtggt cacgccatgt   6480
tttctgatca cgctggtttt ccttttattt agctatgggg cctaccccac ccagcccggg   6540
cagggctatt cccagcagag cagtcagccc tacggacagc agagttacag tggttatagc   6600
cagtccacgg acacttcagg ctatggccag agcagctatt cttcttatgg ccagagccag   6660
aacagtgagt ctttctcagc gggtcacctc ttcctactct ttctgaatat tgcttttctt   6720
```

-continued

```
tttcttgttt tttggagacg gagtctggtc ctgttgccca ggctggagtg cagtggtgct   6780
gtctcagctc actgcaacat cagcctaccg ggttcaaacg attctcctgc ctcagcctcc   6840
tgagtagctg ggattacagg tacctgctac cacgcctggc taattttgtg tttttagtag   6900
agatggggtt tcaccgtgtt ggacaggctg gtctggaact cctgacctcc tgcctgcctt   6960
gacctgccaa agtgctggga ttacaggcgt cagccacaat gccctgaatg ttgcttttct   7020
taaacctgag cagcactgag atgttgaaac tgttccatat ttcttttccg tgaaacagtg   7080
tataagtctt aaaacttttt gggatctgag tcctttacag ggcattgtgg cacacctgta   7140
gtcccagcta ctgaggaggc tgaggcggga ggatcccttg aattcaggag tttggggctg   7200
cagtgagcta tgatggtgcc tgtgaacagc cactgcattc cagcctgggc agtgtgttga   7260
ggccccatct caaaaacata aaaaaaaaaa caaaaaacaa aaatgtttat tggtttgtga   7320
ttctgtttcc atttatttc tttggctttt aattttttg actcttctta ttttccatca   7380
gcatgaaaga gagcatattt tctaaaggaa gaaccagttt taggccaatt ctgaaatgga   7440
gaaaatggtt ttgtttgaaa atgtatgaaa tcatgtgata cataaggagg tgggatttgc   7500
cccaaggtcc tgaagtgtaa ctaagaaagg tggttgtcct gtagatactg cacgcacagc   7560
tgcatattac agtgctgtta acagggatcc ttgggcctgg gtttagaggg tggtgctgga   7620
gatggtgttg ggattggcgg ggtgaaattg gaactgtact aaagagttgg tagaagttga   7680
agcattaaat ttaggctttg aaaggagggt aactatcttt gcctatgagt tgcaacatca   7740
ctaacagctt ctgagaggct ggctttatga gtataggtat tatgttttct ttaacccatt   7800
ccttacattt tctctttcct ggtggctttt gtgactccct ttttcttatc ctggtagcag   7860
gctatggaac tcagtcaact ccccagggat atggctcgac tggcggctat ggcagtagcc   7920
agagctccca atcgtcttac gggcagcagt cctcctaccc tggctatggc cagcagccag   7980
ctcccagcag cacctcggga aggtacggtg gtgttgatgt cggggaaggc ttgaaaagag   8040
gggtgaattg atgaggaatg ataaagggac cagcagtagg agcagttcag aggtgtaatt   8100
ggggtagggg agcctgtgtt gggtacagag aatggactcc actaaaagtg aaaggaaatt   8160
gggggctatg ctgggattgt gattgtgttt tttgtttgtt ttccctagtt acggtagcag   8220
ttctcagagc agcagctatg ggcagcccca gagtgggagc tacagccagc agcctagcta   8280
tggtggacag cagcaaagct atggacagca gcaaagctat aatcccccctc agggctatgg   8340
acagcagaac cagtacaaca gcagcagtgg tggtggaggt ggaggtggag gtggaggtga   8400
gatgtcttca gctttgtctg cagcccattt tctttttctt tttttttttt tttttgagac   8460
ggagtcttgc tctgtctctg ttgctgaggc tggagtgcag tggcacaatc tcggctcact   8520
gcaagctccg ccttccgggt tcgcgccagt ctcctgcctc agcctcccga gtagctggga   8580
ctacaggcat ccgccaccac gcccggctaa tttttgtat ttttagtaga gacggggttt   8640
caccatgtta gccaggatgg tttcgatctc ctgaccttgt gatccgcccg ccttggcctc   8700
ccaaagtgct gggattacag gcgtgagcca ctgtgcctgg tgtctgcagc ccattttcta   8760
taaggatttg tattctcctg ttttagctta aaagagggtt cctgtcttgt ttcctagctg   8820
tctttttact ttcttttgtc cttcattgcc tggcacttgt caaacctttt caaacctttt   8880
agtgctactt tacaatcttt ttgtttttttt tttttaatca ttctttcttt tctcacaggt   8940
aactatggcc aagatcaatc ctccatgagt agtggtggtg gcagtggtgg cggttatggc   9000
aatcaagacc agagtggtgg aggtggcagc ggtggctatg gacagcagga ccgtggaggc   9060
```

-continued

```
cgcggcaggg gtggcagtgg tggcggcggc ggcggcggcg gtggtggtta caaccgcagc   9120
agtggtggct atgaacccag aggtcgtgga ggtggccgtg gaggcagagg tggcatgggg   9180
taggtgtctc atgagccagg gagtatcttt ggtggggagt gtggaggatt gcatgaatct   9240
ccctgaagcc agtccctagt gcatggttta gtattcttgt tgtctaggga tctgtgaggg   9300
ctttgatttg ggggcagtga ctttcttttt acatccccat tttatttttg tgagaacttg   9360
ggagcctgaa ctcccatcca taccactgaa tagagatttt gagtaatgat acttgtttcc   9420
aaaaaaaaag aaaccataca tagatacgta tggattggag tcattaatat cctaggcaag   9480
aaacatggaa gtgaagactt ctttctctgc aagggaaacc gatgatccca ctcctgggaa   9540
atagtaggga aacttggtat gtgtattccc atgtgtcctc tagggagttg gtaatggtta   9600
acctgacttc agcttccagg aattggctac tcttcccgtt ttctatagtc atttgaatcc   9660
acgagcttga tttgcactaa tttgaccgac attgattttg tgtgtgactt ggtttatggg   9720
gccagctgac tgaagtaagc agaccttttg ggcaaaaata tgctttgaca gtggtctccc   9780
acctatttgt tccactgtct gccttcccct ggttacttaa aattcatcag cttgtccaac   9840
tggaccttct ttccttcctg ctgaagttga tttgaagtaa aaccttagat ttgatgttaa   9900
aacagttgtc aaatctgttg gtaaataaga tttgaaggac cctactctgt ctcccttgaa   9960
aaaggggagg aatgtcagtg ttactgtttt tggaaaaagt agatttttaa accgagtttg  10020
gaaatggtaa gtatgcagag gtgggtgggg gcaatctcaa aaacgtgcaa aaatgaggaa  10080
aacaaaaatg aggaaatgtg tgcgtgtgtt taatgcaaaa ctttaaaaag aaaaacaact  10140
gttatgtgac tgttaacttg ctctgcattt tatgtgccac aggtatgaaa ggtgacattg  10200
caaaatactc cgctcttctc gcagtgtaga aggggtgacc ccgggggttg ggggagatca  10260
aaaacagctc agtagttagg acagagctta gctaagtttg tcttgcttta aggggaagtt  10320
gcctttggtt ttgacttttt atggaatggg gttgggtctg cttgctgctt tcaaagcaaa  10380
aaccacaaaa atgtgttcaa ggctacccca gcctggtgtg aaatgtcttc tgggtaaatt  10440
ggggtagggt ttttaaacca actacttggt tgtcaaccac ttgcgacaag aggaaaaaaa  10500
aacatctgct ccatcggaag aacgaccaag gaaaatgggt tatttttttt ccagaggaaa  10560
tagataacgt aacctttttaa agcaaaatct ttataaactg tgtctgagaa attgcacacg  10620
tgtgtgtgac atgctcaaag gtcagacaag ggtggtcag gaagggatgt attttagtag  10680
ccacttgtat ctttttccaa aaacacctac ccatgtttgg ggaatgttaa acaaaatcaa  10740
aaaacaacct tttgtagccg ttggaagctt catgtccttt cttctaactt gtcttctcca  10800
gcggaagtga ccgtggtggc ttcaataaat ttggtggtaa gtgaacagag tttccaaaat  10860
tcccaactcc cagcaatgct ttgtctgatt gttcatttgc agatgtctta gcgtgttaat  10920
ttaaatgtca aaggttttga ggtgtccaga accacctcca gaaaggggta gggtagaatg  10980
ccacctgttg cctggtgtgt gctaacctgg agcaggtagg ggtaagactc aatagtcatc  11040
ttttaccaaa tgggtttgcc ccaggttaat aagaggggtc tagtaggcct tggactgggc  11100
cgttgccaca cctggcactt agtgaccatc atcatgagaa actggagagt gcgtgctgga  11160
acacgtggtg ccatcttggc tttaggatcc ttttgatcgt tgtgtccaag gcttgtgtgt  11220
gtgtgagtgt gtgggagaca actccgaatg tttaattctg gaagagggat gtaacattgc  11280
cctgaggatg gtgaagttgg tatacattta taaagtacgg aatggtgtca atgaatgcaa  11340
ttctatgtat atggacttaa ctgagatggg caaatagaaa ctagctctgg gaaggaacat  11400
gtgcactact tcaagaaaga ttggaagcat gtgtggctca tgggaaataa ccaggtctta  11460
```

```
aacagcacaa actgaattcg tggaccagga aggtcttaaa cagcacaaac tgaattcatg  11520
gaaaaatgac aaatttgaga agtctcccag taagctggaa cttttctggt ttggttaaca  11580
aaaggtttct tgatttgttt caagatttaa agccaaaggt gtgggttcat gacttaggtg  11640
tcattgcgtg tgggtacaat atttatatat ggcgaattca gataaacatt ggtcaaagat  11700
ggtctctgga aaaacaaaat agaggctgca ttacggaaat aagatttctg gtctgttccc  11760
tgggacatgc ttaaaaaata caatagctat tatgtatggt ttttattttc atgtggtttc  11820
ggggaaacaa cacggtttta aggatggttt ctaaagatga aattaaaaat tgttccacaa  11880
gggttaagtg tctggtggta aagttgggag aaactggatg gatgcacatc gcatggctgg  11940
tggcgagccc atctctcttc tctcgggtga gagaaccggg ccaagctgag ttggtttgtt  12000
cactttaatg ggtctccgtt tcccctgcca cctgtgctga ggacatttcc cagcctgagc  12060
tgggggaggc agcatttgct gaagtgtgga gttgtctctg tggagactca agttacagat  12120
cttaaggggc ctgcctagaa ttttctcctc tgggcaggcg acccaggaaa gggtttggag  12180
tgaggctgtg agcacttact tgatatttta caagtttgga tttggtgtta atttttttcc  12240
ttgtccgttt tttcctgttg actaacggct catcttttcc ttgtttttgt tttttttttg  12300
ttcttttttt ccatgtcact aaaggccctc gggaccaagg atcacgtcat gactccggtg  12360
agttcacacg tggtggcatg aaaagagtgg ctaaagtggt atcaagactg cctggatgtt  12420
ctttgaaact attataaaaa ggaaactgaa aaaaatgggg atagagaagg aagggagtta  12480
ggtgtgtcct tagttagcag tgagaagtat ttgttacgaa gtatttctca gaaatacctg  12540
gcttgtgggt tccacccccca gtgatttagg tctgagagga ccctgaaaat ctacctttct  12600
aacaagtccc cagtgatgct gatgcgtctg gaccacactc agatggttta cagcagtggt  12660
tctttcaaaa tgtggatcat gtccaagttg gtgaacaaaa ctagtgaaag acctgaccac  12720
atgaagtaaa gcattgaact cctgtttagg ttgtattgat gtttgtgtac tagatttgaa  12780
tgtaaaatgg gtttcttatt taattcgggg accttcaact gaaagttgat aaatactgat  12840
ggacttttct gtgtggtctt gttgggcatt tcactcctga gccctggttt ccatactgta  12900
tactgggtgt taacatgttt caaaggataa ttgtcaaact gaatctgaaa tttatcagca  12960
tggctggcat atagggactc aaaagggatg tggatttctt tttagttgtc ttccataaac  13020
caaatgatac cagttgcttg atggatacta ggtgctttag gttttttcct gtgtttttta  13080
ttttaccttt tcacatttgc attttctctg ttcaacaagc agaacaggat aattcagaca  13140
acaacaccat ctttgtgcaa ggcctgggtg agaatgttac aattgagtct gtggctgatt  13200
acttcaagca gattggtatt attaaggtac ttgtggagag gagtgggagc tttctgtcag  13260
tgttgtaggc ttgtggattt cacacattag taaaagcaag tctttaatgg ttgccagcag  13320
taaaaacaag tcttagtggt tgttgccagc ttaatttgtt gaggaaagag ccttagttac  13380
tgttttctaa aagagaagtt ctatcttaac acaaaaagta taacttatca gagtacccta  13440
aactcttgag atttgtactc tatagtaact tttagtttta tctttcaata ttggagtgag  13500
agacagtttt ctttaatgga ggtttacatg tgaggtagga agaagtaact gggaagaggg  13560
gagctgaagt ttgggaatta taaacctcat gttctagagg aagaagatgg aaagggagta  13620
ctgtagcctt taaaattgat gttacctcat tttgctttct tcagacaaac aagaaaacgg  13680
gacagcccat gattaatttg tacacagaca gggaaactgg caagctgaag ggagaggcaa  13740
cggtctcttt tgatgaccca ccttcagcta aagcagctat tgactggttt gatggtatgt  13800
```

-continued

```
atgagaaggc tggcagaggt ggggctgggg atatagggca gcaagcctta ggaaacaagc  13860
catagtttga gggttctttt gagtcttcca acacttactt tagctgcggt ttcaggtagt  13920
ctcatttttg cttatgtgtc agcagattat aaaccatttg agaaaggcac gcttctcttg  13980
tattttcgga ttaatgtgtc ttgcatttaa agtctgttga tgattttttg tttctctagg  14040
taaagaattc tccggaaatc ctatcaaggt ctcatttgct actcgccggg cagactttaa  14100
tcggggtggt ggcaatggtc gtggaggccg agggcgagga ggtgaggagc tacctgctag  14160
tggtgcagag gggtaatggg gagagtgcag aagatggtaa aggcttgcat ggaatgggtt  14220
agatttacca aacttggaga gggagcagac ccatacttgg tctatctgca ttaggaccca  14280
tgggccgtgg aggctatgga ggtggtggca gtggtggtgg tggccgagga ggatttccca  14340
gtggaggtgg tggcggtgga ggacagcagc gagctggtga ctggaagtgt cctaatccgt  14400
gagtgaaact taattttttt cttagttctc ttgcatgcgt gctctttgat atattggtac  14460
tgaggtatgt gcgtgttttc caaagaagta aatgtcaagg ccacactgtt ggggtcagat  14520
ttagccaaaa gcttacctag gtaaggttga tgtaatggga aaggtaatgg attgggttca  14580
gtaatactga tttttgttcc tgactctgag aagcaagccg ttttgtcttt ctgaagcttc  14640
agtttcctca ctgtatctct aaagtcaccg tagtttcttc ctagttctag gtcttgccta  14700
ttccccatcg ctccagactg attgtcttcc tttctcctta gcacctgtga gaatatgaac  14760
ttctcttgga ggaatgaatg caaccagtgt aaggccccta aaccagatgg cccaggaggg  14820
ggaccaggtg gctctcacat gggtaagaaa ggcagacctg gtgctaggga gctgggacca  14880
aagaatcctt aatttttcag cggggaggct cggggaacat aggggaatgg gaatatgata  14940
gatcttgttt cttttgtcct agggggtaac tacggggatg atcgtcgtgg tggcagagga  15000
ggctatgatc gaggcggcta ccggggccgc ggcggggacc gtggaggctt ccgagggggc  15060
cggggtggtg gggacagagg tggctttggc cctggcaaga tggattccag gtaagacttt  15120
aaatcagaat aaaaaagtag agcagttgaa cagaggccat aggataacag ggttttgttg  15180
agaaagtggt ttcattttga gggctaggtg gaaagacctg aggttgtaac cagtagtgga  15240
gagggaagga aaattaactc agggggagtg aatctgtaga cccacttgag ataagatact  15300
cgctgggtta ggtaggaggg gcagatagga tatctaggct tggagaggct ggtaactcaa  15360
atataatgga tacttaattt tttttttttt ttttgcaggg gtgagcacag acaggatcgc  15420
agggagaggc cgtattaatt agcctggctc cccaggttct ggaacagctt tttgtcctgt  15480
acccagtgtt accctcgtta ttttgtaacc ttccaattcc tgatcaccca agggtttttt  15540
tgtgtcggac tatgtaattg taactatacc tctggttccc attaaaagtg accattttag  15600
ttaaatttgg ttcctcttcc cccttttcac tttcctggaa gatcgatgtc ccgatcagga  15660
aggtagagag ttttcctgtt cagattaccc tgcccagcag gaactggaat acagtgttcg  15720
gggagaaggc caaatgatat ccttgagagc agagattaaa cttttctgtc atggggaaag  15780
ttggtgtata aatgagaaat gaagaacatg ggatgtcatg agtgttggcc taaatttgcc  15840
cagctatggg gaatttttcc tttaccacat ttatttgcat actggtctta gtttatttgc  15900
agcagtttat cccttttttaa gaactctttg atcttttggc ccttttaatg gtgaggctca  15960
aacaaactac atttaaatgg ggcagtattc agatttgacc atggtggaga gcgcttagcc  16020
actctgggtc tttcacagga aggagagtaa ctgagtgctg caggagtttg tggagtggag  16080
tcaggatcta ggaggtgagt gactcccttc ctagctgccc tggtgaacag cgcttgggta  16140
gatacctgct ataaggagac tggtctggct gggttacttt cacatcctgc ctgtactcag  16200
```

agggcttgag gtcattgaca ttatgagatt ttaggcttga tcccttttttg attggagggt 16260
ggaaggccct cctaagggaa tgataagtga taagaggggg aaggggttgc agccaatgag 16320
ttaaaacctt agagcagtgc tcctcagcct cttaccatgt ggttgtaaac ttgcacgtac 16380
ctgccaacca gttatttagc atgcttttta ttttagttac acagagcgta acattaaccc 16440
aagagcagaa aggttttatt tacagggttt tcgaacttgg tttgtaagac agctgccatc 16500
acaagcatag cttacaaatg tgctggggac ccctaattgg gaagtgcttt cctctcaaat 16560
ttttattttt tatttttaga gacagagtct tgctctgtca tccaggctgg agtgcagtgg 16620
cgtgatctcg gctcactgta gcctctgcct cctgagttta agcgattctc ctgcctcagg 16680
agaatcccag cttctgagta gctgagacta caggcgtggg ccaccatgcc cacctagttt 16740
ttgcattttt agtggaggtg tggtttcact gtgttggcca ggctggtctc ttaactcctg 16800
acctcaggtg atccacctgc cttggcctcc caaagtgctg gaattacagg catgagccgc 16860
tgcatctggc catcctctca aattttcaag tgttccacaa gtatgttctc tactgaagag 16920
ttgctgcatc cttgaatctt gggtgatttg aggcacagaa actatgactt tattttttga 16980
gatggagttt tgctcttgtt gcccaggctg gagtgcaatg gcacgttttt cggcttaccg 17040
caactgccgc ctcctgggtt caagcgatag ctgggattac aggcatgcgc caccatgccc 17100
agctaattta tttgtatttt tagtagagac ggggtttctc catgttggtc aggctggtct 17160
cgaactcccg acctcaggtg atgtgcacac ctcagcctcc caataaacca tgacttttaa 17220
gaggaatagc aggtttactt cccctgccag cattggggtg ctctctaagc aacagtaggc 17280
ggagagtggt ctggcgtatt aaaaacaaag gatcgtcaag tgggccttcc caggcattgc 17340
tttgacttag tacatgtaga ggatgtggca gttctctccg tccctgccac tgctggtttc 17400
tttgttaaat gtttagttga aatggcctga tacgatattt gagtagttca ctgttggtgc 17460
tttgcctagc aggattctaa tcttgctttg gttgtggtcc cctgatgccc tcctgttagg 17520
agtggaggag gtcgaagctc cttgtaagat atgattactg ggaccattag tgtcaagttc 17580
ctgtgtcctt caaatggcat atgtgattgg ccttgacctt aaaaggaaat agggtcccag 17640
gtgactgttt agtgggtagg tccagtttgg ggggatcttc caggagaatg gatagagaca 17700
cctagcagca gagagaacat tggtgcctct caagccaacc tcccacctca gcctcccaag 17760
tagctgggac tacaggtgct tcctcgctac cacacctggg taattttttt tttaattact 17820
tttttttttt taagaaacag ggtttcactg ggttgcccag gctggtcttg aactggcctc 17880
aagtgacctg cctgcctcag cctcccaaag tgctgggatc acaggtgtga cccactgcgt 17940
ttggccagaa tactctattc ttactgaatg attgaaatct gtcttgaagc attaggtgtc 18000
ccatttttgt gagttggaat tgggacaggc taagtaggaa gtgaggaggg tggggagagc 18060
tgtgctgtag gtctgtttgt cccttccttg atgtagcctt cagttagccc tttcagcttt 18120
tttccccatc ttgtgccggg ccttcctggg tttcagtact tggatgtagg gctgcagtta 18180
tgtcagtggt gggtagattg accaggaatt aaggtctagg gtccagccca tgtgagactt 18240
gactcactga tctaccttta ggcatgtctt ccttccagtc tcatcctttt taaatttttt 18300
tttttttttt gagacggtct cactctcacc caggctggat tgcagtggtg tgatctcgac 18360
caactgcaac ctctgcctcc cacccgcaag ctatctgccc acctcagcct ctggagtagc 18420
tgggacggga ctacaggcac ctgccaccat gactggctaa tttttttttg tatttttttgt 18480
ggagatgggg tcttgccatg ttgctcaggc tggtctggtc tcaaaactgc tctgggctca 18540

-continued

```
agtgattgtc ccactttggc ctcccagagt gctgggatta aggtgtgaga tactgtgtcc  18600
ggctatgaaa attttatttt taattaactt gtatatattt atggggtaca atgtcctatt  18660
tctgtacatg tacacattgt ggaatcaaat caggctaata tatccatcac ttcatatcat  18720
tagcatgaat gagaacatac aaagccactc ttagaaaatt ttgaaattta tgttatttca  18780
gcccttttat gctggaggtt gcaaatgttt tgtgaataat cagaccaaaa ataaaaacaa  18840
aaaatgattg acttcagtca ttcagtaaga atagtgtgtt ctggccgagt gtggtgggtc  18900
acacctgtaa tggagcacta ggcgtaaatg ggttgaaacg ggtctcccta tgttgctcag  18960
gctggacttg aactcctggg cttaagtgat cttcttgccc ttagcctctc agctgggact  19020
atggatgcat gccactgtgt ctcacgtttt tatgaactgt agtcaccatg ctgtgcagtg  19080
gcttaccaga actcatttct tgcatctgaa gtgttgtacc ctttgtctcc ctgcttaccc  19140
atacctccaa gcctctggta acccccattc tactttcagt ttccgagttt gactttctag  19200
attccgtgta taagttcatg cagtctttct gtggcttatt ttagcataat gtcttctaga  19260
tttatcgatt cacccatgtt acaaataacg gtttcctttt aaaaagctga atagcattct  19320
gttgtgtcta cataccacat ttaaaaatcc atccgttaat tgggcacttg ggttgcttgc  19380
atatcttggc tagtgtgaat aacgctgcat tgggtgggag tgcagacatc tctgacgtac  19440
agatttcttt tttcttttt ggagacagag tcttgccctg ccacccaggc tggagtgcag  19500
tggtaggatc ttggctcact gcaacctctg ccttccagat tcaagtgatt ctcctgcctt  19560
agcctcccag gtagctggga ttacaggtgt gcaccaccat gcccagctaa ctcttgtatt  19620
tttagtagag atggggtttc tccatgttgg ccaggctggt ctcagtgggc cccagcgatc  19680
cttccgcctc gggctcctga atgactggga ctacaggtgt gctactgcac ctggctattt  19740
tgaaataatt tgacttagaa gaatatttct acaattgtgt tcaccttctt atgcaaatac  19800
aatcttcagt ggcgctggca tatacaagct gagaaagtat tgtcaagtgg gttgtgccag  19860
cacatctgac caggattttt tgttgtagaa atattggatc ctcacctgag gccaggagtt  19920
tgagaccagc ctggctaaca tggtgaaact ccgactctac taaaaataca aaaattagct  19980
gggcgtggtg gcaggtgcct gcagtcccag ctgctcggga ggttgaggca ggagaatcgc  20040
ttgaacccag gaggcggagg ttgcggtgag ccgagatcgc gccgctgcac tctagcctgg  20100
gcaatgaagt gagactctgt ctcaaaaaac gaagtattag atcctcaatc tcaaggtatt  20160
ctaagaaatt ttggagacca ttgagtctaa aattcccagt atctttgagg caggaacaga  20220
cttggagaat gtagtttatg agcaggagtt tggagctgga agaaatactg ctttctgttg  20280
gtggttaatg ctgtcagctc cttggattgt ggctttagcc ctaaatattg gggcagtaga  20340
gactcttacc tggaaaacaa ttgagggcca cccatgttag cggcaagagg cagaggaaag  20400
cttggatggt tgggctgaag atggtggatg tgctgtccct gtgagagtgc tgatgctgga  20460
ctctggagcc aacgacaaag tgtttgagca agcagggtcc aagcaagggc agtcgagggc  20520
cggatgaagt gggcaggaac cgagtttccc aggtgacatc ctgcctgtgc tcatcacgcc  20580
gaggggtgtt gcacaatcac accgattctt tgtcactact gagtgcagtg ttcttaagaa  20640
tggggacctg gcagctgggt gcgatggctt gtgcctgtaa tcccaacact ttgggaggct  20700
gaagtaggca gatcacgagg tcaggagttt gagaccagcc tggccaacat agtgaaccct  20760
gtctctacta aaaatacaaa aaattagcca ggcctggtgg caggcacctg taattccagc  20820
tactcgagag gctgaggcag gagaatcgct tgaaaccggg aggtggaggt tgcagtgacc  20880
caagatcgtg ccattgcccc ctggcctggg cgacagtgcg agactctcaa aaaaataagt  20940
```

```
aaataaataa aaggagacct aggcttgttg tgcttgtttt ttggttttga ttttccagag  21000

tttgagggaa agttgaccca tcctgtttat tgtgcccttg aggaggaaac aaggcaaatc  21060

cctactcttg tgggcagggg tgcgcaaacc tgtcagtctg agatggctag aaccacatcc  21120

tctataactt gagggggata atctatctat ctatctatct atacctatat atatacacac  21180

acacacacag attaaaaaaa atatatatat atacagagga atcctccctt acctatggtt  21240

tcatcttaca cagtttcagt acagtataat aatctcctgt gcttaattta taaattgaac  21300

tttataattt gtcaacatat ggattctagc tcagtaggtc caggtggggc tcaagatacg  21360

catttcaggc caggtgcggt ggctcattcc tgtaatccca gcactttggg aggccgaggt  21420

gggaggatca cttgagccca ggagttgaga ctaacctggg taacagcaac attttgtcta  21480

ccagaatttt aaaaaattgg gcgcggtggc tcacacctgt aatcccagca cttcgggagg  21540

ccaaggtggg cagcttggcc aacatggtga aagcccacct ctactaaaag tacaaaattt  21600

aggcaggtgt ggtggcatgc acctgtaatc ccagctactt gggaggctga ggcaggagaa  21660

ttgcttgaac ctgggaggtg gaggttgcag tgagctgaga tcatgcaact gcactcaagc  21720

ctgggtgaca gaatgagact ccatctcaaa aaaaaaaaag tgtggtggca tgtacctgtg  21780

gtcccagctg gagaggttga ggctgcagtg agctgtgttc ccaccactgc actccagccc  21840

gcaggcctgg gaaacagaac aagactgtcc ccctgccctc cccgcaaagc atttctgaca  21900

ggctttctgg tgataatgat gctgttggtt caacacctct cagagtaacg ttctagagtt  21960

tggcagagtc aaattatttc tgaaggggaa ctttgtacaa                        22000
```

<210> SEQ ID NO 3
<211> LENGTH: 526
<212> TYPE: PRT
<213> ORGANISM: Homo sapiens

<400> SEQUENCE: 3

```
Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
            20                  25                  30

Tyr Gly Gln Gln Ser Tyr Ser Gly Tyr Ser Gln Ser Thr Asp Thr Ser
        35                  40                  45

Gly Tyr Gly Gln Ser Ser Tyr Ser Ser Tyr Gly Gln Ser Gln Asn Thr
    50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
                85                  90                  95

Tyr Pro Gly Tyr Gly Gln Gln Pro Ala Pro Ser Ser Thr Ser Gly Ser
            100                 105                 110

Tyr Gly Ser Ser Ser Gln Ser Ser Ser Tyr Gly Gln Pro Gln Ser Gly
        115                 120                 125

Ser Tyr Ser Gln Gln Pro Ser Tyr Gly Gly Gln Gln Gln Ser Tyr Gly
    130                 135                 140

Gln Gln Gln Ser Tyr Asn Pro Pro Gln Gly Tyr Gly Gln Gln Asn Gln
145                 150                 155                 160

Tyr Asn Ser Ser Ser Gly Gly Gly Gly Gly Gly Gly Gly Gly Gly Asn
                165                 170                 175

Tyr Gly Gln Asp Gln Ser Ser Met Ser Ser Gly Gly Gly Ser Gly Gly
```

-continued

```
            180                 185                 190

Gly Tyr Gly Asn Gln Asp Gln Ser Gly Gly Gly Gly Ser Gly Gly Tyr
        195                 200                 205

Gly Gln Gln Asp Arg Gly Gly Arg Gly Arg Gly Gly Ser Gly Gly Gly
    210                 215                 220

Gly Gly Gly Gly Gly Gly Gly Tyr Asn Arg Ser Ser Gly Gly Tyr Glu
225                 230                 235                 240

Pro Arg Gly Arg Gly Gly Gly Arg Gly Gly Arg Gly Gly Met Gly Gly
                245                 250                 255

Ser Asp Arg Gly Gly Phe Asn Lys Phe Gly Gly Pro Arg Asp Gln Gly
            260                 265                 270

Ser Arg His Asp Ser Glu Gln Asp Asn Ser Asp Asn Asn Thr Ile Phe
        275                 280                 285

Val Gln Gly Leu Gly Glu Asn Val Thr Ile Glu Ser Val Ala Asp Tyr
    290                 295                 300

Phe Lys Gln Ile Gly Ile Ile Lys Thr Asn Lys Lys Thr Gly Gln Pro
305                 310                 315                 320

Met Ile Asn Leu Tyr Thr Asp Arg Glu Thr Gly Lys Leu Lys Gly Glu
                325                 330                 335

Ala Thr Val Ser Phe Asp Asp Pro Pro Ser Ala Lys Ala Ala Ile Asp
            340                 345                 350

Trp Phe Asp Gly Lys Glu Phe Ser Gly Asn Pro Ile Lys Val Ser Phe
        355                 360                 365

Ala Thr Arg Arg Ala Asp Phe Asn Arg Gly Gly Gly Asn Gly Arg Gly
    370                 375                 380

Gly Arg Gly Arg Gly Gly Pro Met Gly Arg Gly Gly Tyr Gly Gly Gly
385                 390                 395                 400

Gly Ser Gly Gly Gly Gly Arg Gly Gly Phe Pro Ser Gly Gly Gly Gly
                405                 410                 415

Gly Gly Gly Gln Gln Arg Ala Gly Asp Trp Lys Cys Pro Asn Pro Thr
            420                 425                 430

Cys Glu Asn Met Asn Phe Ser Trp Arg Asn Glu Cys Asn Gln Cys Lys
        435                 440                 445

Ala Pro Lys Pro Asp Gly Pro Gly Gly Gly Pro Gly Gly Ser His Met
    450                 455                 460

Gly Gly Asn Tyr Gly Asp Asp Arg Arg Gly Gly Arg Gly Gly Tyr Asp
465                 470                 475                 480

Arg Gly Gly Tyr Arg Gly Arg Gly Gly Asp Arg Gly Gly Phe Arg Gly
                485                 490                 495

Gly Arg Gly Gly Gly Asp Arg Gly Gly Phe Gly Pro Gly Lys Met Asp
            500                 505                 510

Ser Arg Gly Glu His Arg Gln Asp Arg Arg Glu Arg Pro Tyr
        515                 520                 525
```

<210> SEQ ID NO 4

<400> SEQUENCE: 4

000

<210> SEQ ID NO 5

<400> SEQUENCE: 5

000

<210> SEQ ID NO 6
<211> LENGTH: 17
<212> TYPE: DNA
<213> ORGANISM: Artificial sequence
<220> FEATURE:
<223> OTHER INFORMATION: Primer

<400> SEQUENCE: 6
tgcttgcttg cctgtgc 17

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
actgtaactc tgctgtccgt 20

<210> SEQ ID NO 8
<211> LENGTH: 18
<212> TYPE: DNA
<213> ORGANISM: Artificial sequence
<220> FEATURE:
<223> OTHER INFORMATION: Probe

<400> SEQUENCE: 8
ttgaggccat gtccgcgc 18

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
ggcaaattca acggcacagt 20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
gggtctcgct cctggaagat 20

<210> SEQ ID NO 11
<211> LENGTH: 27
<212> TYPE: DNA
<213> ORGANISM: Artificial sequence
<220> FEATURE:
<223> OTHER INFORMATION: Probe

<400> SEQUENCE: 11
aaggccgaga atgggaagct tgtcatc 27

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
gtttatctga attcgccata 20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
gcaatgtcac ctttcatacc 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
agttccaaca ccgctgagta 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
gccatgtccg cgcacgcgcg 20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ggactggcta taaccactgt 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ctggccataa gaagaatagc 20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
catagccgcc agtcgagcca 20

<210> SEQ ID NO 19

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cccgtaagac gattgggagc 20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
tgagaactgc taccgtaact 20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
tgctgtccac catagctagg 20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
caccactact catggaggat 20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
ctgctgtcca tagccaccgc 20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gcggttgtaa ccaccaccgc 20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cgagtagcaa atgagacctt 20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
ccaccacccc gattaaagtc 20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
tgggaaatcc tcctcggcca 20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
acgacgatca tccccgtagt 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
ccgcctcgat catagcctcc 20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
gccccggtag ccgcctcgat 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
ttaatacggc ctctccctgc 20

<210> SEQ ID NO 32
<211> LENGTH: 20
<212> TYPE: DNA

-continued

<213> ORGANISM: Artificial sequence
<220> FEATURE:
<223> OTHER INFORMATION: Synthetic oligonucleotide

<400> SEQUENCE: 32
ccaggctaat taatacggcc 20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
tagtccgaca caaaaaaacc 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
ttacaattac atagtccgac 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
ggaaccagag gtatagttac 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
tcgggacatc gatcttccag 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gcagggtaat ctgaacagga 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
atttggcctt ctccccgaac 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
taggccaaca ctcatgacat 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
gagtcactca cctcctagat 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
gtcaatgacc tcaagccctc 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
cgtgcaagtt tacaaccaca 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tcttacaaac caagttcgaa 20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ggaagtaaac ctgctattcc 20

<210> SEQ ID NO 45
<211> LENGTH: 20
<212> TYPE: DNA
<213> ORGANISM: Artificial sequence
<220> FEATURE:

-continued

<223> OTHER INFORMATION: Synthetic oligonucleotide

<400> SEQUENCE: 45
accactctcc gcctactgtt 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
ttaatacgcc agaccactct 20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
cccacttgac gatcctttgt 20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
agtgaactac tcaaatatcg 20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggtcccagta atcatatctt 20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
ggccaatcac atatgccatt 20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
actggaccta cccactaaac 20

-continued

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tgggacacct aatgcttcaa 20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
gcagccctac atccaagtac 20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
ctggtcaatc tacccaccac 20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
ccctagacct taattcctgg 20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
attttcatag ccggacacag 20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
tggccgggcc ccttcgctgg 20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
cgatctatct ccacccccat 20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
gcaggactag cccacgatct 20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
gtcgaagctt aagtacgctc 20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
ctcgcgccct tacctaccgt 20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
cccggtccca ctgaaaacga 20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
agacttcccg ccccgcgcgc 20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
ggagcgatcc cgcccattcg 20

<210> SEQ ID NO 65
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 65
ccaccgccgc caaaccgtta 20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
gggccgtccc caagtccgtt 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
cggccgttct tctccgtccc 20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
ggctttttag tgcaaagcca 20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
gtgattgctc taaaacatcg 20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
agttccaatt tcaccccgcc 20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
ccgtaccttc ccgaggtgct 20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
atcaacacca ccgtaccttc 20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
ggccatagtt acctgtgaga 20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
atcatcggtt tcccttgcag 20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
gcttacttca gtcagctggc 20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
gtcacccctt ctacactgcg 20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
gttggtttaa aaaccctacc 20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
tacctgctcc aggttagcac 20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
tccaaggcct actagacccc 20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
tcattgacac cattccgtac 20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
ggtccacgaa ttcagtttgt 20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
gttgtttccc cgaaaccaca 20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
tgggctcgcc accagccatg 20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
ccaaaccctt tcctgggtcg 20

-continued

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
gggtcctctc agacctaaat 20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
ggtactctga taagttatac 20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
ggcttgtttc ctaaggcttg 20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
cgcacatacc tcagtaccaa 20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
gttccccgag cctccccgct 20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
accctgttat cctatggcct 20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
ccctcctacc taacccagcg 20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
cgaagttcca acaccgctga 20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
gtttgaggcc atgtccgcgc 20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
gcctgaagtg tccgtggact 20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
cagtcgagcc atatccctgg 20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
tgccatagcc gccagtcgag 20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
gcccgtaaga cgattgggag 20

<210> SEQ ID NO 98

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
atagctaggc tgctggctgt 20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
ctgctgtcca ccatagctag 20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
cttgattgcc ataaccgcca 20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
cctgctgtcc atagccaccg 20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
tgcggttgta accaccaccg 20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
gcgagtagca aatgagacct 20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
gccaccaccc cgattaaagt 20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
actgggaaat cctcctcggc 20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
cacgacgatc atccccgtag 20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
gccgcctcga tcatagcctc 20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
aagcctccac ggtccccgcc 20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
attaatacgg cctctccctg 20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
gccaggctaa ttaatacggc 20

<210> SEQ ID NO 111
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 111
ttacatagtc cgacacaaaa 20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
ggtcactttt aatgggaacc 20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
gatcgggaca tcgatcttcc 20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
ccttctcccc gaacactgta 20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
catttggcct tctccccgaa 20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
ttaggccaac actcatgaca 20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
ggagtcactc acctcctaga 20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
cctccaatca aaaagggatc 20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
gttacgctct gtgtaactaa 20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
gtcttacaaa ccaagttcga 20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
gagagcaccc caatgctggc 20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
gaccactctc cgcctactgt 20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
ttttaatacg ccagaccact 20

<210> SEQ ID NO 124
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 124
gcccacttga cgatcctttg 20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
gcaccaacag tgaactactc 20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
atggtcccag taatcatatc 20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
gtcaaggcca atcacatatg 20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
aactggacct acccactaaa 20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
atgggacacc taatgcttca 20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
tgcagcccta catccaagta 20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
accttaattc ctggtcaatc 20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
gaccctagac cttaattcct 20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
cccggatcct catggctttg 20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
gtggccgggc cccttcgctg 20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
gcccacgatc tatctccacc 20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
ggaacgcact ccgcccoctt 20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
gcccttacct accgtttgag 20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
cctcgcgccc ttacctaccg 20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
cacgggatcg ccgccccggt 20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
ctcgcgacag aaagctgaac 20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
cggagcgatc ccgcccattc 20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
accaccgccg ccaaaccgtt 20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
tcgggccgtc cccaagtccg 20

<210> SEQ ID NO 144
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 144
gcggccgttc ttctccgtcc 20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
actctttgac caatcccgga 20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
ggtggacatc cacaattttc 20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
cagttccaat ttcaccccgc 20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
accgtacctt cccgaggtgc 20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
ccgacatcaa caccaccgta 20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
ttggccatag ttacctgtga 20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
tcaggttaac cattaccaac 20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
gtagggtcct tcaaatctta 20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
ggtcacccct tctacactgc 20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
ggttgacaac caagtagttg 20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
attgagtctt acccctacct 20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
gtccaaggcc tactagaccc 20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
ttcattgaca ccattccgta 20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
cacctaagtc atgaacccac 20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
ccgtgttgtt tccccgaaac 20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
agatgggctc gccaccagcc 20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
gggcctttag tgacatggaa 20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
ggtccccgaa ttaaataaga 20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
gctacagtac tccctttcca 20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164
gcaagacaca ttaatccgaa 20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
acgcacatac ctcagtacca 20

<210> SEQ ID NO 166
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 166
ccattcccct atgttccccg 20

<210> SEQ ID NO 167
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 167
aaccctgtta tcctatggcc 20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
ctagatatcc tatctgcccc 20

<210> SEQ ID NO 169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 169
acgaagttcc aacaccgctg 20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
ctgggaatag ccctgcccgg 20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
atagcctgaa gtgtccgtgg 20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
ccagtcgagc catatccctg 20

<210> SEQ ID NO 173
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 173
actgccatag ccgccagtcg 20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 174
tgcccgtaag acgattggga 20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 175
ccatagctag gctgctggct 20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
gctgctgtcc accatagcta 20

<210> SEQ ID NO 177

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
tcttgattgc cataaccgcc 20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 178
cggtcctgct gtccatagcc 20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179
gccacagact caattgtaac 20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 180
gattaaagtc tgcccggcga 20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
tgccaccacc ccgattaaag 20

<210> SEQ ID NO 182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 182
cactgggaaa tcctcctcgg 20

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
ccacgacgat catccccgta 20

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
agccgcctcg atcatagcct 20

<210> SEQ ID NO 185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 185
ctcggaagcc tccacggtcc 20

<210> SEQ ID NO 186
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 186
taattaatac ggcctctccc 20

<210> SEQ ID NO 187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 187
agccaggcta attaatacgg 20

<210> SEQ ID NO 188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 188
aattacatag tccgacacaa 20

<210> SEQ ID NO 189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 189
atcgatcttc caggaaagtg 20

<210> SEQ ID NO 190
<211> LENGTH: 20
<212> TYPE: DNA

-continued

<213> ORGANISM: Artificial sequence
<220> FEATURE:
<223> OTHER INFORMATION: Synthetic oligonucleotide

<400> SEQUENCE: 190
tctaccttcc tgatcgggac 20

<210> SEQ ID NO 191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 191
gccttctccc cgaacactgt 20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 192
tcatttggcc ttctccccga 20

<210> SEQ ID NO 193
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 193
gcctcaccat taaaagggcc 20

<210> SEQ ID NO 194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 194
gggagtcact cacctcctag 20

<210> SEQ ID NO 195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 195
taggagggcc ttccaccctc 20

<210> SEQ ID NO 196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 196
ttaatgttac gctctgtgta 20

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
tgtcttacaa accaagttcg 20

<210> SEQ ID NO 198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 198
tctccgccta ctgttgctta 20

<210> SEQ ID NO 199
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 199
cgccagacca ctctccgcct 20

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
tttttaatac gccagaccac 20

<210> SEQ ID NO 201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 201
aaggcccact tgacgatcct 20

<210> SEQ ID NO 202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 202
gattagaatc ctgctaggca 20

<210> SEQ ID NO 203
<211> LENGTH: 20
<212> TYPE: DNA
<213> ORGANISM: Artificial sequence
<220> FEATURE:

-continued

<223> OTHER INFORMATION: Synthetic oligonucleotide

<400> SEQUENCE: 203
acttgacact aatggtccca 20

<210> SEQ ID NO 204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 204
gacctaccca ctaaacagtc 20

<210> SEQ ID NO 205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 205
caaactggac ctacccacta 20

<210> SEQ ID NO 206
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 206
cttagcctgt cccaattcca 20

<210> SEQ ID NO 207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207
ctgcagccct acatccaagt 20

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
gaccttaatt cctggtcaat 20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209
ggaccctaga ccttaattcc 20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
acccggatcc tcatggcttt 20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
accgagattc ctgtggccgg 20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 212
agcccacgat ctatctccac 20

<210> SEQ ID NO 213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 213
ctccgccgcc tacgcaccgc 20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
cgcccttacc taccgtttga 20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
gcctcgcgcc cttacctacc 20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
cgcggcttcc cgccacaggg 20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
cacaccggac gcgcgccgcc 20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
ggaacggagc gatcccgccc 20

<210> SEQ ID NO 219
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 219
cgaaccctga ccaccgccgc 20

<210> SEQ ID NO 220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 220
actctcgggc cgtccccaag 20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
agccccactt aagatacacg 20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
caggtttgaa ttcgaacagt 20

<210> SEQ ID NO 223
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 223
cgttatcagc caagtgttct 20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
ctaccaactc tttagtacag 20

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
caccgtacct tcccgaggtg 20

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 226
cccgacatca acaccaccgt 20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
ggctcatgag acacctaccc 20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 228
gtcaggttaa ccattaccaa 20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
cttaccattt ccaaactcgg 20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
gggtcacccc ttctacactg 20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
taccctaccc ctttctggag 20

<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232
acccctctta ttaacctggg 20

<210> SEQ ID NO 233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 233
gcaacggccc agtccaaggc 20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
gagctagttt ctatttgccc 20

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
gacacctaag tcatgaaccc 20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
accatcctta aaaccgtgtt 20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
cccggttctc tcacccgaga 20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 238
cccgagggcc tttagtgaca 20

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
cctagtatcc atcaagcaac 20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
gccttctcat acataccatc 20

<210> SEQ ID NO 241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 241
tgcaagacac attaatccga 20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
acatcaacct tacctaggta 20

-continued

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
cccgtagtta ccccctagga 20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
gcgagtatct tatctcaagt 20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 245
cctagatatc ctatctgccc 20

<210> SEQ ID NO 246
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 246
aacgaagttc caacaccgct 20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
actctgctgt ccgtagggct 20

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
ggccatagcc tgaagtgtcc 20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
gccagtcgag ccatatccct 20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
ggctactgcc atagccgcca 20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
gactgctgcc cgtaagacga 20

<210> SEQ ID NO 252
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 252
accatagcta ggctgctggc 20

<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
gatcttggcc atagttacct 20

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
gtcttgattg ccataaccgc 20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
ccacggtcct gctgtccata 20

<210> SEQ ID NO 256

-continued

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
ggctgtcccg ttttcttgtt 20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
caccccgatt aaagtctgcc 20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258
cggcctccac gaccattgcc 20

<210> SEQ ID NO 259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 259
gattaggaca cttccagtca 20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260
accacgacga tcatccccgt 20

<210> SEQ ID NO 261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 261
tagccgcctc gatcatagcc 20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
cctcggaagc ctccacggtc 20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
ctaattaata cggcctctcc 20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
ggttacaaaa taacgagggt 20

<210> SEQ ID NO 265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 265
caattacata gtccgacaca 20

<210> SEQ ID NO 266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 266
gacatcgatc ttccaggaaa 20

<210> SEQ ID NO 267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 267
ctctaccttc ctgatcggga 20

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
ggccttctcc ccgaacactg 20

<210> SEQ ID NO 269
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 269
ctcaaggata tcatttggcc 20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
cgctctccac catggtcaaa 20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 271
cagaccagtc tccttatagc 20

<210> SEQ ID NO 272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 272
ttaggagggc cttccaccct 20

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
ggttaatgtt acgctctgtg 20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
gcaactcttc agtagagaac 20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
actctccgcc tactgttgct 20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
acgccagacc actctccgcc 20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
gtttttaata cgccagacca 20

<210> SEQ ID NO 278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 278
gggaaggccc acttgacgat 20

<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
agattagaat cctgctaggc 20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
aacttgacac taatggtccc 20

<210> SEQ ID NO 281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
ggacctaccc actaaacagt 20

<210> SEQ ID NO 282
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 282
agatcccccc aaactggacc 20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
cctacttagc ctgtcccaat 20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
gtcaatctac ccaccactga 20

<210> SEQ ID NO 285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 285
agaccttaat tcctggtcaa 20

<210> SEQ ID NO 286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
gggctggacc ctagacctta 20

<210> SEQ ID NO 287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 287
cacccggatc ctcatggctt 20

<210> SEQ ID NO 288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 288
aaccgagatt cctgtggccg 20

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
tagcccacga tctatctcca 20

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
gctccgccgc ctacgcaccg 20

<210> SEQ ID NO 291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 291
gcgcccttac ctaccgtttg 20

<210> SEQ ID NO 292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 292
tcgcctcgcg cccttaccta 20

<210> SEQ ID NO 293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 293
ccgcggcttc ccgccacagg 20

<210> SEQ ID NO 294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 294
aaggctcaca ccggacgcgc 20

<210> SEQ ID NO 295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 295
cgatcccgag cctccgcccc 20

<210> SEQ ID NO 296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 296
ggtcgaaccc tgaccaccgc 20

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
cgttcttctc cgtccctatc 20

<210> SEQ ID NO 298
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 298
tgggactcca gatggttccg 20

<210> SEQ ID NO 299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 299
agccattatc gccaggagtc 20

<210> SEQ ID NO 300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 300
cgtgatcaga aaacatggcg 20

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
gcaaagatag ttaccctcct 20

<210> SEQ ID NO 302
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 302
ccaccgtacc ttcccgaggt 20

<210> SEQ ID NO 303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 303
gccttccccg acatcaacac 20

<210> SEQ ID NO 304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 304
gccctcacag atccctagac 20

<210> SEQ ID NO 305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 305
agtcaggtta accattacca 20

<210> SEQ ID NO 306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 306
gtcacctttc atacctgtgg 20

<210> SEQ ID NO 307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 307
gtcctaacta ctgagctgtt 20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308

-continued ggcattctac cctaccctt 20

<210> SEQ ID NO 309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 309
gacccctctt attaacctgg 20

<210> SEQ ID NO 310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 310
tggcaacggc ccagtccaag 20

<210> SEQ ID NO 311
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 311
gacctggtta tttcccatga 20

<210> SEQ ID NO 312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 312
gcaatgacac ctaagtcatg 20

<210> SEQ ID NO 313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 313
aaccatcctt aaaaccgtgt 20

<210> SEQ ID NO 314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 314
gcccggttct ctcacccgag 20

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
atccttggtc ccgagggcct 20

<210> SEQ ID NO 316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 316
gcacctagta tccatcaagc 20

<210> SEQ ID NO 317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 317
gccagccttc tcatacatac 20

<210> SEQ ID NO 318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 318
ttccggagaa ttctttacct 20

<210> SEQ ID NO 319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 319
tacatcaacc ttacctaggt 20

<210> SEQ ID NO 320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 320
ccccgtagtt accccctagg 20

<210> SEQ ID NO 321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 321
agcgagtatc ttatctcaag 20

<210> SEQ ID NO 322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 322
gcctagatat cctatctgcc 20

<210> SEQ ID NO 323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 323
caacgaagtt ccaacaccgc 20

<210> SEQ ID NO 324
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 324
ggctataacc actgtaactc 20

<210> SEQ ID NO 325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 325
tggccatagc ctgaagtgtc 20

<210> SEQ ID NO 326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 326
tagccgccag tcgagccata 20

<210> SEQ ID NO 327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 327
tggctactgc catagccgcc 20

<210> SEQ ID NO 328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 328
ggactgctgc ccgtaagacg 20

<210> SEQ ID NO 329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 329
gtccaccata gctaggctgc 20

<210> SEQ ID NO 330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 330
catggaggat tgatcttggc 20

<210> SEQ ID NO 331
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 331
tggtcttgat tgccataacc 20

<210> SEQ ID NO 332
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 332
gccgcggcct ccacggtcct 20

<210> SEQ ID NO 333
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 333
gggctgtccc gttttcttgt 20

<210> SEQ ID NO 334
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 334
accaccccga ttaaagtctg 20

<210> SEQ ID NO 335

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 335
tcggcctcca cgaccattgc 20

<210> SEQ ID NO 336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 336
acgatcatcc ccgtagttac 20

<210> SEQ ID NO 337
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 337
caccacgacg atcatccccg 20

<210> SEQ ID NO 338
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 338
ggtagccgcc tcgatcatag 20

<210> SEQ ID NO 339
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 339
accaccccgg ccccctcgga 20

<210> SEQ ID NO 340
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 340
ggctaattaa tacggcctct 20

<210> SEQ ID NO 341
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 341
aggttacaaa ataacgaggg 20

<210> SEQ ID NO 342
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 342
gttacaatta catagtccga 20

<210> SEQ ID NO 343
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 343
gggacatcga tcttccagga 20

<210> SEQ ID NO 344
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 344
tctctacctt cctgatcggg 20

<210> SEQ ID NO 345
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 345
ttggccttct ccccgaacac 20

<210> SEQ ID NO 346
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 346
gccaacactc atgacatccc 20

<210> SEQ ID NO 347
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 347
gcgctctcca ccatggtcaa 20

<210> SEQ ID NO 348
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 348
gccagaccag tctccttata 20

<210> SEQ ID NO 349
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 349
ggttttaact cattggctgc 20

<210> SEQ ID NO 350
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 350
tcttgggtta atgttacgct 20

<210> SEQ ID NO 351
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 351
tcccagctat cgcttgaacc 20

<210> SEQ ID NO 352
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 352
cactctccgc ctactgttgc 20

<210> SEQ ID NO 353
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 353
atacgccaga ccactctccg 20

<210> SEQ ID NO 354
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 354
tgtttttaat acgccagacc 20

<210> SEQ ID NO 355
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 355
tgggaaggcc cacttgacga 20

<210> SEQ ID NO 356
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 356
cactcctaac aggagggcat 20

<210> SEQ ID NO 357
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 357
gaacttgaca ctaatggtcc 20

<210> SEQ ID NO 358
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 358
tggacctacc cactaaacag 20

<210> SEQ ID NO 359
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 359
gctaggtgtc tctatccatt 20

<210> SEQ ID NO 360
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 360
tcctacttag cctgtcccaa 20

<210> SEQ ID NO 361
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 361
ggtcaatcta cccaccactg 20

<210> SEQ ID NO 362
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 362
tagaccttaa ttcctggtca 20

<210> SEQ ID NO 363
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 363
gtcaagtctc acatgggctg 20

<210> SEQ ID NO 364
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 364
tcacccggat cctcatggct 20

<210> SEQ ID NO 365
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 365
ggaaccgaga ttcctgtggc 20

<210> SEQ ID NO 366
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 366
actagcccac gatctatctc 20

<210> SEQ ID NO 367
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 367
gtacgctccg ccgcctacgc 20

<210> SEQ ID NO 368
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 368
cgcgccctta cctaccgttt 20

<210> SEQ ID NO 369
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 369
ccgtcgcctc gcgcccttac 20

<210> SEQ ID NO 370
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 370
tccgcggctt cccgccacag 20

<210> SEQ ID NO 371
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 371
ccgcccattc gcgaaggacc 20

<210> SEQ ID NO 372
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 372
gagggcggcc ccgatcccga 20

<210> SEQ ID NO 373
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 373
tggtcgaacc ctgaccaccg 20

<210> SEQ ID NO 374
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 374
ccgttcttct ccgtccctat 20

<210> SEQ ID NO 375
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 375
aactgctcgc cttaggaggc 20

<210> SEQ ID NO 376
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 376
gattgctcta aaacatcgcg 20

<210> SEQ ID NO 377
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 377
cgtgcagtat ctacaggaca 20

<210> SEQ ID NO 378
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 378
gctgttagtg atgttgcaac 20

<210> SEQ ID NO 379
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 379
accaccgtac cttcccgagg 20

<210> SEQ ID NO 380
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 380
tcaagccttc cccgacatca 20

<210> SEQ ID NO 381
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 381
gcctaggata ttaatgactc 20

<210> SEQ ID NO 382
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 382
ggccccataa accaagtcac 20

<210> SEQ ID NO 383
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 383
cggagtattt tgcaatgtca 20

<210> SEQ ID NO 384
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 384
aggcaacttc cccttaaagc 20

<210> SEQ ID NO 385
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 385
aggtggcatt ctaccctacc 20

<210> SEQ ID NO 386
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 386
tagacccctc ttattaacct 20

<210> SEQ ID NO 387
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 387
acaacgatca aaaggatcct 20

<210> SEQ ID NO 388
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 388
tccacgaatt cagtttgtgc 20

<210> SEQ ID NO 389
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 389
cgccaccagc catgcgatgt 20

<210> SEQ ID NO 390
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 390
ggcccggttc tctcacccga 20

<210> SEQ ID NO 391
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 391
gtcttgatac cactttagcc 20

<210> SEQ ID NO 392
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 392
ggcaaccatt aaagacttgc 20

<210> SEQ ID NO 393
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 393
gcttgctgcc ctatatcccc 20

<210> SEQ ID NO 394
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 394
ccatgcaagc ctttaccatc 20

<210> SEQ ID NO 395
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 395
cccattacat caaccttacc 20

<210> SEQ ID NO 396
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 396
atccccgtag ttacccccta 20

<210> SEQ ID NO 397
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 397
acctaaccca gcgagtatct 20

<210> SEQ ID NO 398
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 398
agcctagata tcctatctgc 20

<210> SEQ ID NO 399
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 399
acgcgcgcac aggcaagcaa 20

<210> SEQ ID NO 400
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 400
ctggctataa ccactgtaac 20

<210> SEQ ID NO 401
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 401
ctggccatag cctgaagtgt 20

<210> SEQ ID NO 402
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 402
atagccgcca gtcgagccat 20

<210> SEQ ID NO 403
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 403
ctggctactg ccatagccgc 20

<210> SEQ ID NO 404
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 404
aggactgctg cccgtaagac 20

<210> SEQ ID NO 405
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 405
gctgtccacc atagctaggc 20

<210> SEQ ID NO 406
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 406
accactactc atggaggatt 20

<210> SEQ ID NO 407
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 407
gctgtccata gccaccgctg 20

<210> SEQ ID NO 408
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 408
tgccgcggcc tccacggtcc 20

<210> SEQ ID NO 409
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 409
aagagaccgt tgcctctccc 20

<210> SEQ ID NO 410
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 410
caccaccccg attaaagtct 20

<210> SEQ ID NO 411
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 411
ctcggcctcc acgaccattg 20

<210> SEQ ID NO 412
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 412
gacgatcatc cccgtagtta 20

<210> SEQ ID NO 413
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 413
tcgatcatag cctcctctgc 20

<210> SEQ ID NO 414

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 414
cggtagccgc ctcgatcata 20

<210> SEQ ID NO 415
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 415
atacggcctc tccctgcgat 20

<210> SEQ ID NO 416
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 416
caggctaatt aatacggcct 20

<210> SEQ ID NO 417
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 417
cccttgggtg atcaggaatt 20

<210> SEQ ID NO 418
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 418
agttacaatt acatagtccg 20

<210> SEQ ID NO 419
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 419
cgggacatcg atcttccagg 20

<210> SEQ ID NO 420
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 420
ctctctacct tcctgatcgg 20

<210> SEQ ID NO 421
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 421
tttggccttc tccccgaaca 20

<210> SEQ ID NO 422
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 422
ggccaacact catgacatcc 20

<210> SEQ ID NO 423
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 423
actcacctcc tagatcctga 20

<210> SEQ ID NO 424
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 424
gtaacccagc cagaccagtc 20

<210> SEQ ID NO 425
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 425
aggttttaac tcattggctg 20

<210> SEQ ID NO 426
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 426
ctcttgggtt aatgttacgc 20

<210> SEQ ID NO 427
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 427

atcccagcta tcgcttgaac                                                  20


<210> SEQ ID NO 428
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 428

ccactctccg cctactgttg                                                  20


<210> SEQ ID NO 429
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 429

aatacgccag accactctcc                                                  20


<210> SEQ ID NO 430
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 430

cacttgacga tcctttgttt                                                  20


<210> SEQ ID NO 431
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 431

gtatcaggcc atttcaacta                                                  20


<210> SEQ ID NO 432
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 432

caaggagctt cgacctcctc                                                  20


<210> SEQ ID NO 433
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 433

ggaacttgac actaatggtc                                                  20
```

<210> SEQ ID NO 434
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 434
ctggacctac ccactaaaca 20

<210> SEQ ID NO 435
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 435
ctgctaggtg tctctatcca 20

<210> SEQ ID NO 436
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 436
gccctacatc caagtactga 20

<210> SEQ ID NO 437
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 437
tggtcaatct acccaccact 20

<210> SEQ ID NO 438
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 438
ctagacctta attcctggtc 20

<210> SEQ ID NO 439
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 439
gagtcaagtc tcacatgggc 20

<210> SEQ ID NO 440
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 440
gttgccttgc ctttcggcct 20

<210> SEQ ID NO 441
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 441
gtggtacggc ctgagtgccc 20

<210> SEQ ID NO 442
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 442
aggactagcc cacgatctat 20

<210> SEQ ID NO 443
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 443
gcttaagtac gctccgccgc 20

<210> SEQ ID NO 444
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 444
tcgcgccctt acctaccgtt 20

<210> SEQ ID NO 445
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 445
cgccgtcgcc tcgcgccctt 20

<210> SEQ ID NO 446
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 446
acttcccgcc ccgcgcgcga 20

<210> SEQ ID NO 447
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 447
gcgatcccgc ccattcgcga 20

<210> SEQ ID NO 448
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 448
agagggcggc cccgatcccg 20

<210> SEQ ID NO 449
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 449
tccgttggtc gaaccctgac 20

<210> SEQ ID NO 450
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 450
gccgttcttc tccgtcccta 20

<210> SEQ ID NO 451
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 451
gcaactgctc gccttaggag 20

<210> SEQ ID NO 452
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 452
tgattgctct aaaacatcgc 20

<210> SEQ ID NO 453
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 453
gttccaattt caccccgcca 20

<210> SEQ ID NO 454
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 454
gactgagttc catagcctgc 20

<210> SEQ ID NO 455
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 455
caccaccgta ccttcccgag 20

<210> SEQ ID NO 456
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 456
aggctcccct accccaatta 20

<210> SEQ ID NO 457
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 457
tcatcggttt cccttgcaga 20

<210> SEQ ID NO 458
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 458
tcagctggcc ccataaacca 20

<210> SEQ ID NO 459
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 459 cacccc ttct acactgcgag 20

<210> SEQ ID NO 460
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 460
aaccctaccc caatttaccc 20

<210> SEQ ID NO 461
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 461
acaggtggca ttctacccta 20

<210> SEQ ID NO 462
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 462
gcctactaga cccctcttat 20

<210> SEQ ID NO 463
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 463
gtataccaac ttcaccatcc 20

<210> SEQ ID NO 464
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 464
gtccacgaat tcagtttgtg 20

<210> SEQ ID NO 465
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 465
tgtttatctg aattcgccat 20

<210> SEQ ID NO 466
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 466

```
ctcgccacca gccatgcgat                                                20


<210> SEQ ID NO 467
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 467

gcaggcccct taagatctgt                                                20


<210> SEQ ID NO 468
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 468

agtcttgata ccactttagc                                                20


<210> SEQ ID NO 469
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 469

gcaacaacca ctaagacttg                                                20


<210> SEQ ID NO 470
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 470

gcttgtttcc taaggcttgc                                                20


<210> SEQ ID NO 471
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 471

agtttcactc acggattagg                                                20


<210> SEQ ID NO 472
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 472

ccccgctgaa aaattaagga                                                20


<210> SEQ ID NO 473
<211> LENGTH: 20
<212> TYPE: DNA
<213> ORGANISM: Artificial sequence
```

<220> FEATURE:
<223> OTHER INFORMATION: Synthetic oligonucleotide

<400> SEQUENCE: 473
ccctgttatc ctatggcctc 20

<210> SEQ ID NO 474
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 474
tcctacctaa cccagcgagt 20

<210> SEQ ID NO 475
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 475
ccaagcctag atatcctatc 20

<210> SEQ ID NO 476
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 476
ggcacataaa atgcagagca 20

<210> SEQ ID NO 477
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 477
gagtattttg caatgtcacc 20

<210> SEQ ID NO 478
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 478
ggagtatttt gcaatgtcac 20

<210> SEQ ID NO 479
<211> LENGTH: 20
<212> TYPE: DNA
<213> ORGANISM: Artificial sequence -continued

```
<220> FEATURE:
<223> OTHER INFORMATION: Synthetic oligonucleotide

<400> SEQUENCE: 479

gcggagtatt ttgcaatgtc                                              20


<210> SEQ ID NO 480
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 480

gtgcatccat ccagtttctc                                              20


<210> SEQ ID NO 481
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 481

cctggttatt tcccatgagc                                              20
```